US007507808B2

(12) United States Patent
Dobie

(10) Patent No.: US 7,507,808 B2
(45) Date of Patent: Mar. 24, 2009

(54) MODULATION OF ENDOTHELIAL LIPASE EXPRESSION

(75) Inventor: Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 349 days.

(21) Appl. No.: 10/319,915

(22) Filed: Dec. 12, 2002

(65) Prior Publication Data

US 2004/0115653 A1 Jun. 17, 2004

(51) Int. Cl.
*C07H 21/04* (2006.01)
*C07H 21/02* (2006.01)
*A61K 48/00* (2006.01)

(52) U.S. Cl. .................... 536/24.5; 536/23.1; 536/24.3; 514/44

(58) Field of Classification Search ................ 536/24.5, 536/23.1; 514/44; 435/6, 325, 375
See application file for complete search history.

(56) References Cited

U.S. PATENT DOCUMENTS

| | | | | |
|---|---|---|---|---|
| 5,801,154 A * | 9/1998 | Baracchini et al. | ............ | 514/44 |
| 5,856,461 A | 1/1999 | Colote et al. | | |
| 5,998,148 A * | 12/1999 | Bennett et al. | ................. | 435/6 |
| 6,395,530 B1 | 5/2002 | Jaye et al. | ................... | 435/198 |
| 6,582,908 B2 | 6/2003 | Fodor et al. | | |
| 6,821,724 B1 * | 11/2004 | Mittman et al. | ................ | 435/6 |

FOREIGN PATENT DOCUMENTS

| | | |
|---|---|---|
| WO | WO 00/57837 | * 10/2000 |
| WO | WO 00/73452 | 12/2000 |
| WO | WO 01/16312 | 3/2001 |
| WO | WO 01 16312 | * 3/2001 |
| WO | WO 01/40466 | 6/2001 |
| WO | WO 01/96388 | 12/2001 |
| WO | WO 2004/009541 | * 1/2004 |

OTHER PUBLICATIONS

Taylor et al. Drug Disc. Today, 1999. 4(12)562-567.*

New England Biolabs 1998/99 Catalog, (cover page and pp. 121 & 284).*

Mahato et al., Modulation of gene expression by antisense and antigene oligodeoxynucleotides and small interfering RNA, Jan. 2005, Expert Opinion on Drug Delivery, vol. 2, No. 1, pp. 3-28.*

Scherer et al., Approaches for the sequence-specific knockdown of mRNA, 2003, Nat. Biotechnol., 21(12), pp. 1457-1465.*

Elbashir et al., Functional anatomy of siRNAs for mediating efficient RNAi in Drosophila melanogaster embryo lysate, 2001, The EMBO Journal, vol. 20, No. 23, pp. 6877-6888.*

Hirata et al., Cloning of a Unique Lipase from Endothelial Cells Extends the Lipase Gene Family, 1999, The Journal of Biological Chemistry, vol. 274, No. 20, pp. 14170-14175.*

Holen et al., Positional effects of short interfering RNAs targeting the human coagulation trigger Tissue Factor, 2002, Nucleic Acids Research, vol. 30, No. 8, pp. 1757-1766.*

Olie et al., Analysis of ribosyl-modified, mixed backbone analogs of a bcl-2/bcl-xL antisense oligonucleotide, 2002, Biochimica et Biophysica Acta, 1576, pp. 101-109.*

Tuschl et al., The siRNA user guide, Aug. 26, 2001 (on-line), retrieved Jan. 31, 2002, Max Planck Institute for Biophysical Chemistry, pp. 1, 3 and 5, http://www.mpibpc.gwdg.de/abteilungen/100/105/siRNAuserguide.pdf.*

Taylor et al., "Antisense Oligonucleotides: A Systematic High-Throughput Approach To Target Validation And Gene Function Determination," *Drug Discovery Today*, Dec. 1999, vol. 4, No. 12, pp. 562-567.

International Search Report for Application No: PCT/US03/39436 dated Jul. 27, 2004.

Bonne et al., Sequencing and chromosomal assignment of the rat endothelial-derived lipase gene (Lipg), DNA Seq., 2001, 12:285-287.

deLemos et al., Identification of genetic variants in endothelial lipase in persons with elevated high-density lipoprotein cholesterol, Circulation, 2002, 106:1321-1326.

Hirata et al., Cloning of a unique lipase from endothelial cells extends the lipase gene family, J. Biol. Chem., 1999, 274:14170-14175.

Hirata et al., Regulated expression of endothelial cell-derived lipase, Biochem. Biophys. Res. Commun., 2000, 272:90-93.

Jaye et al., A novel endothelial-derived lipase that modulates HDL metabolism, Nat. Genet., 1999, 21:424-428.

Jin et al., Lipases and HDL metabolism, Trends Endocrinol. Metab., 2002, 13:174-178.

Krieger, The "best" of cholesterols, the "worst" of cholesterols: a tale of two receptors, Proc. Natl. Acad. SCi. U. S. A., 1998, 95:4077-4080.

McCoy et al., Characterization of the lipolytic activity of endothelial lipase, J. Lipid Res., 2002, 43:921-929.

Strauss et al., Endothelial cell derived lipase mediates uptake and binding of HDL particles and the selective uptake of HDL associated cholesterol esters independent of catalytic activity, Biochem. J., 2002, 6.

Wong et al., The lipase gene family, J. Lipid Res., 2002, 43:993-999.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Elbashir et al., "Functional anatomy of siRNAs for mediating efficient RNAi in Drosophila melanogaster embryo lysate" The EMBO Journal (2001) 20(23):6877-6888.

Holen et al., "Positional effects of short interfering RNAs targeting the human coagulation trigger Tissue Factor" Nucleic Acids Research (2002) 30(8): 1757-1766.

(Continued)

*Primary Examiner*—Amy Bowman

(57) ABSTRACT

Compounds, compositions and methods are provided for modulating the expression of endothelial lipase. The compositions comprise oligonucleotides, targeted to nucleic acid encoding endothelial lipase. Methods of using these compounds for modulation of endothelial lipase expression and for diagnosis and treatment of disease associated with expression of endothelial lipase are provided.

21 Claims, No Drawings

OTHER PUBLICATIONS

Mahato et al., "Modulation of gene expression by antisense and antigene oligodeoxynucleotides and small interfering RNA" Expert Opinion on Drug Delivery (2005) 2(1):3-28.
New England Biolabs 1998/99 Catalog (cover page and pp. 121 and 284).
Olie et al., "Analysis of ribosyl-modified, mixed backbone analogs of a bcl-2/bcl-xL antisense oligonucleotide" Biochemica et Biophysica Acts (2002) 1576:101-109.
Scherer et al., "Approaches for the sequence-specific knockdown of mRNA" Nat. Biotechnol. (2003) 12(12):1457-1465.

* cited by examiner

MODULATION OF ENDOTHELIAL LIPASE EXPRESSION

FIELD OF THE INVENTION

The present invention provides compositions and methods for modulating the expression of endothelial lipase. In particular, this invention relates to compounds, particularly oligonucleotide compounds, which, in preferred embodiments, hybridize with nucleic acid molecules encoding endothelial lipase. Such compounds are shown herein to modulate the expression of endothelial lipase.

BACKGROUND OF THE INVENTION

Atherosclerosis is the major causative factor of heart disease and stroke, and the leading cause of death in Western countries is cardiovascular disease. Dyslipidaemia is a primary contributor to atherosclerosis. Because triglycerides are insoluble in the bloodstream, they are packaged for plasma transport into micelle-like lipoprotein particles composed of protein and phospholipid shells surrounding a non-polar core of acylglycerols, free cholesterol, and cholesterol esters. Lipoproteins have been classified into five broad categories on the basis of their functional and physical properties: chylomicrons (which transport dietary lipids from intestine to tissues); very low density lipoproteins (VLDL), intermediate density lipoproteins (IDL) and low density lipoproteins (LDL), (all of which transport triacylglycerols and cholesterol from the liver to tissues); and high density lipoproteins (HDL) (which transport endogenous cholesterol from tissues to the liver, as well as mediating selective cholesteryl ester delivery to steroidogenic tissues). All of these particles undergo continuous metabolic processing and have somewhat variable properties and compositions. Plasma concentrations of LDL and HDL are directly and inversely related, respectively, to the risk of atherosclerotic cardiovascular disease (Krieger, *Proc. Natl. Acad. Sci. U.S.A.*, 1998, 95, 4077-4080).

HDL protect the arterial wall from the development of atherosclerosis by promoting efflux of excess cholesterol from cells in the arterial wall and returning it to the liver for excretion into the bile, as well as by protecting LDL from oxidation, thereby reducing the inflammatory response of epithelial cells, inhibiting the coagulation pathway, and promoting the availability of nitric oxide. The metabolism of HDL is influenced by several members of the triacylglycerol (TG) lipase family of proteins, which hydrolyze triglycerides, phospholipids and cholesteryl esters, generating fatty acids to facilitate intestinal absorption, energy production or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and VLDL in muscle and adipose tissues. Hepatic lipase (HL) hydrolyzes HDL triglyceride and phospholipids, generating smaller, lipid-depleted HDL particles, and plays a role in the uptake of HDL cholesterol (Jin et al., *Trends Endocrinol. Metab.*, 2002, 13, 174-178; Wong and Schotz, *J. Lipid Res.*, 2002, 43, 993-999). Endothelial lipase (also known as EDL, EL, LIPG, endothelial-derived lipase and endothelial cell-derived lipase) was identified using differential display to isolate mRNAs which were differentially regulated in response to oxidized-LDL (Jaye et al., *Nat. Genet.*, 1999, 21, 424-428). Independently, the human endothelial lipase gene was identified in human umbilical vein endothelial cells (HUVECs) undergoing tube formation in a model of vascular formation (Hirata et al., *J. Biol. Chem.*, 1999, 274, 14170-14175).

In humans, the endothelial lipase gene has been assigned to chromosome 18, and the rat endothelial lipase gene was identified and mapped to rat chromosome 18 in the vicinity of a quantitative trait locus that affects serum HDL levels after a high fat diet (Bonne et al., *DNA Seq.*, 2001, 12, 285-287).

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, 6 of which potentially produce functional variants of the protein, and the frequencies of these variants were found to be associated with elevated levels of HDL cholesterol in human subjects (deLemos et al., *Circulation*, 2002, 106, 1321-1326).

Notably, the endothelial lipase-mediated binding and uptake of HDL particles and the selective uptake of HDL-derived cholesterol esters have been reported to be independent of its enzymatic lipolytic activity (Strauss et al., *Biochem. J.*, 2002).

Recombinant endothelial lipase protein has substantial phospholipase activity but has been reported to have less hydrolytic activity toward triglyceride lipids (Hirata et al., *J. Biol. Chem.*, 1999, 274, 14170-14175; Jaye et al., *Nat. Genet.*, 1999, 21, 424-428). However, endothelial lipase does exhibit triglyceride lipase activity ex vivo in addition to its HDL phospholipase activity, and endothelial lipase was found to hydrolyze HDL more efficiently than other lipoproteins (McCoy et al., *J. Lipid Res.*, 2002, 43, 921-929). Overexpression of the human endothelial lipase gene in the livers of mice markedly reduces plasma concentrations of HDL cholesterol and its major protein apolipoprotein A-I (apoA-I) (Jaye et al., *Nat. Genet.*, 1999, 21, 424-428).

On the basis of its amino acid sequence homology to other members of the TG lipase family, including the presence of a characteristic 19-amino acid "lid" domain predicted to form an amphipathic helix covering the catalytic pocket of the enzyme and confers substrate specificity to the enzymes of the TG lipase family, and its demonstrated phospholipase activity, the endothelial lipase protein is believed to be involved in lipoprotein metabolism and vascular biology (Hirata et al., *J. Biol. Chem.*, 1999, 274, 14170-14175; Jaye et al., *Nat. Genet.*, 1999, 21, 424-428).

Endothelial lipase was cloned from epithelial cells but has been demonstrated to be abundantly expressed in a variety of tissues including ovary, testis, thyroid gland, liver, lung, kidney and placenta, the latter suggesting the potential for a role in development (Hirata et al., *J. Biol. Chem.*, 1999, 274, 14170-14175; Jaye et al., *Nat. Genet.*, 1999, 21, 424-428). Interestingly, endothelial lipase mRNA levels were upregulated in HUVEC and coronary artery endothelial cells upon treatment with inflammatory cytokines implicated in vascular disease etiology and vascular remodeling, including TNF-alpha and IL-1beta. Thus, endothelial lipase is predicted to be intricately involved in modulating vessel wall lipid metabolism and to play a role in vascular diseases such as atherosclerosis (Hirata et al., *Biochem. Biophys. Res. Commun.*, 2000, 272, 90-93).

Disclosed and claimed in U.S. Pat. No. 6,395,530 is an isolated nucleic acid which hybridizes at high stringency to a nucleic acid having a sequence selected from a group of which endothelial lipase is a member or to a target consisting of nucleotides from 44-79 of the endothelial lipase gene wherein the complement of said isolated nucleic acid encodes a polypeptide having triacylglycerol lipase or phospholipase A activity. Further claimed are a vector, a composition, a recombinant cell and method for preparing a polypeptide. Antisense nucleic acids are generally disclosed (Jaye et al., 2002).

Disclosed and claimed in PCT Publications WO 01/40466 and WO 00/73452 is an isolated nucleic acid having at least 80% nucleic acid sequence identity to a nucleotide sequence that encodes the endothelial lipase protein or to a nucleotide sequence selected from a group of which the endothelial lipase gene is a member, a vector, a host cell, a process for producing a polypeptide, an isolated polypeptide, a chimeric molecule, and antibody, a method of detecting said polypeptide in a sample, a method of linking a bioactive molecule to a cell expressing said polypeptide, a method of modulating at least one biological activity of a cell expressing said polypeptide, methods for stimulating the release of TNF-alpha from human blood, for modulating the uptake of glucose or FFA by skeletal muscle or adipocyte cells, for stimulating the proliferation or differentiation of chondrocyte cells, for stimulating the proliferation of inner ear utricular supporting cells, endothelial cells or T-lymphocyte cells, for stimulating the proliferation of or gene expression in pericyte cells, for stimulating the release of proteoglycans from cartilage, for stimulating the release of a cytokine from PBMC cells, for inhibiting the binding of A-peptide to factor VIIA, for inhibiting the differentiation of adipocyte cells, for detecting the presence of tumor in an mammal, an oligonucleotide probe derived from any of several nucleotide sequences cited, a composition useful for the treatment of immune related diseases, use of a polypeptide to prepare said composition, a method of diagnosing an immune related disease in a mammal, an immune related disease diagnostic kit, a method for identifying an agonist or a compound capable of inhibiting the expression and/or activity of a polypeptide, a vector, and an ex vivo producer cell. Antisense oligonucleotide agonists or antagonists are generally disclosed (Ashkenazi et al., 2000; Baker et al., 2001).

Disclosed and claimed in PCT Publication WO 01/96388 is an isolated polynucleotide comprising a sequence selected from a group of nucleotide sequences, complements of said sequences, sequences consisting of at least 20 contiguous residues of one of said sequences, sequences that hybridize to said sequences, sequences having at least 75% identity to said sequence, and degenerate variants of said sequence, an isolated polypeptide, an expression vector, a host cell, an isolated antibody, a method for detecting the presence of a cancer in a patient, a fusion protein, an oligonucleotide that hybridizes to said sequence, a method for stimulating and/or expanding T cells specific for a tumor protein, an isolated T cell population, a composition comprising a first component selected from the group consisting of physiologically acceptable carriers and immunostimulants, and a second component selected from the group consisting of said polypeptides, polynucleotides, antibodies, fusion proteins, T cell populations and antigen presenting cells that express a polypeptide, a method for stimulating an immune response in a patient, a method for the treatment of a cancer in a patient, a method for determining the presence of a cancer in a patient, a diagnostic kit comprising at least one oligonucleotide or antibody, and a method for inhibiting the development of a cancer in a patient. Antisense oligonucleotides are generally disclosed (Jiang et al., 2001).

Currently, there are no known therapeutic agents which effectively inhibit the synthesis of endothelial lipase.

Consequently, there remains a long felt need for agents capable of effectively inhibiting endothelial lipase function.

Antisense technology is emerging as an effective means for reducing the expression of specific gene products and may therefore prove to be uniquely useful in a number of therapeutic, diagnostic, and research applications for the modulation of endothelial lipase expression.

The present invention provides compositions and methods for modulating endothelial lipase expression.

SUMMARY OF THE INVENTION

The present invention is directed to compounds, especially nucleic acid and nucleic acid-like oligomers, which are targeted to a nucleic acid encoding endothelial lipase, and which modulate the expression of endothelial lipase. Pharmaceutical and other compositions comprising the compounds of the invention are also provided. Further provided are methods of screening for modulators of endothelial lipase and methods of modulating the expression of endothelial lipase in cells, tissues or animals comprising contacting said cells, tissues or animals with one or more of the compounds or compositions of the invention. Methods of treating an animal, particularly a human, suspected of having or being prone to a disease or condition associated with expression of endothelial lipase are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding endothelial lipase. This is accomplished by providing oligonucleotides which specifically hybridize with one or more nucleic acid molecules encoding endothelial lipase. As used herein, the terms "target nucleic acid" and "nucleic acid molecule encoding endothelial lipase" have been used for convenience to encompass DNA encoding endothelial lipase, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

One preferred result of such interference with target nucleic acid function is modulation of the expression of endothelial lipase. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Sience*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes endothelial lipase.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding endothelial lipase, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of endothelial lipase. "Modulators" are those compounds that decrease or increase the expression of a nucleic acid molecule encoding endothelial lipase and which comprise at least an 8-nucleobase portion which is complementary to a preferred target segment. The screening method comprises the steps of contacting a preferred target segment of a nucleic acid molecule encoding endothelial lipase with one or more candidate modulators, and selecting for one or more candidate modulators which decrease or increase the expression of a nucleic acid molecule encoding endothelial lipase. Once it is shown that the candidate modulator or modulators are capable of modulating (e.g. either decreasing or increasing) the expression of a nucleic acid molecule encoding endothelial lipase, the modulator may then be employed in further investigative studies of the function of endothelial lipase, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Sience*, 1998, 282, 430-431; Montgomery et al., *Proc. Natl. Acad. Sci. USA*, 1998, 95, 15502-15507; Tuschl et al., *Genes Dev*., 1999, 13, 3191-3197; Elbashir et al., *Nature*, 2001, 411, 494-498; Elbashir et al., *Genes Dev*. 2001, 15, 188-200). For example, such double-stranded moieties have been shown to inhibit the target by the classical hybridization of antisense strand of the duplex to the target, thereby triggering enzymatic degradation of the target (Tijsterman et al., *Sience*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between endothelial lipase and a disease state, phenotype, or condition. These methods include detecting or modulating endothelial lipase comprising contacting a sample, tissue, cell, or organism with the compounds of the present invention, measuring the nucleic acid or protein level of endothelial lipase and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett*., 2000, 480, 17-24; Celis, et al., *FEBS Lett*., 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol*., 1999, 303, 258-72), TOGA (total gene expression analysis) (Sutcliffe, et al., *Proc. Natl. Acad. Sci U.S.A*., 2000, 97, 1976-81), protein arrays and proteomics (Celis, et al., *FEBS Lett*., 2000, 480, 2-16; Jungblut, et al., *Electrophoresis*, 1999, 20, 2100-10), expressed sequence tag (EST) sequencing (Celis, et al., *FEBS Lett*., 2000, 480, 2-16; Larsson, et al., *J. Biotechnol*., 2000, 80, 143-57), subtractive RNA fingerprinting (SuRF) (Fuchs, et al., *Anal. Biochem*., 2000, 286, 91-98; Larson, et al., *Cytometry*, 2000, 41, 203-208), subtractive cloning, differential display (DD) (Jurecic and Belmont, *Curr. Opin. Microbiol*., 2000, 3, 316-21), comparative genomic hybridization (Carulli, et al., *J. Cell Biochem. Suppl*., 1998, 31, 286-96), FISH (fluorescent in situ hybridization) techniques (Going and Gusterson, *Eur. J. Cancer*, 1999, 35, 1895-904) and mass spectrometry methods (*To, Comb. Chem. High Throughput Screen*, 2000, 3, 235-41).

The compounds of the invention are useful for research and diagnostics, because these compounds hybridize to nucleic acids encoding endothelial lipase. For example, oligonucleotides that are shown to hybridize with such efficiency and under such conditions as disclosed herein as to be effective endothelial lipase inhibitors will also be effective primers or probes under conditions favoring gene amplification or detection, respectively. These primers and probes are useful in methods requiring the specific detection of nucleic acid molecules encoding endothelial lipase and in the amplification of said nucleic acid molecules for detection or for use in further studies of endothelial lipase. Hybridization of the antisense oligonucleotides, particularly the primers and probes, of the invention with a nucleic acid encoding endothelial lipase can be detected by means known in the art. Such means may include conjugation of an enzyme to the oligonucleotide, radiolabelling of the oligonucleotide or any other suitable detection means. Kits using such detection means for detecting the level of endothelial lipase in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of endothelial lipase is treated by administering antisense compounds in accordance with this invention. For example, in one non-limiting embodiment, the methods comprise the step of administering to the animal in need of treatment, a therapeutically effective amount of a endothelial lipase inhibitor. The endothelial lipase inhibitors of the present invention effectively inhibit the activity of the endothelial lipase protein or inhibit the expression of the endothelial lipase protein. In one embodiment, the activity or expression of endothelial lipase in an animal is inhibited by about 10%. Preferably, the activity or expression of endothelial lipase in an animal is inhibited by about 30%. More preferably, the activity or expression of endothelial lipase in an animal is inhibited by 50% or more.

For example, the reduction of the expression of endothelial lipase may be measured in serum, adipose tissue, liver or any other body fluid, tissue or organ of the animal. Preferably, the cells contained within said fluids, tissues or organs being analyzed contain a nucleic acid molecule encoding endothelial lipase-protein and/or the endothelial lipase protein itself.

The compounds of the invention,can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Sience*, 1991, 254, 1497-1500.

Preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene $(—CH_2—)_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B. ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. applications Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teni-poside, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylamino-oxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2' -O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'- groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand*,. 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3, H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Endothelial Lipase In accordance with the present invention, a series of nucleic acid duplexes comprising the antisense compounds of the present invention and their complements can be designed to target endothelial lipase. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 280) and having a two-nucleobase overhang of deoxythymidine(dT) would have the following structure:

```
cgagaggcggacgggaccgTT    Antisense Strand (SEQ ID NO: 281)
||||||||||||||||||||
TTgctctccgcctgccctggc    Complement (SEQ ID NO: 282)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate endothelial lipase expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3, H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HuVEC Cells:

The human umbilical vein endothilial cell line HuVEC was obtained from the American Type Culture Collection (Manassas, Va.). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 96-well plates (Falcon-Primaria #3872) at a density of 10000 cells/ well for use in RT-PCR Analysis.

For Northern blotting or other analyses, cells may be seeded onto 100 mm or other standard tissue culture plates and treated similarly, using appropriate volumes of medium and oligonucleotide.

Primary Mouse Hepatocytes

Primary mouse hepatocytes were prepared from CD-1 mice purchased from Charles River Labs. Primary mouse hepatocytes were routinely cultured in Hepatoyte Attachment Media (Gibco) supplemented with 10% Fetal Bovine Serum (Gibco/Life Technologies, Gaithersburg, Md.), 250 nM dexamethasone (Sigma), 10 nM bovine insulin (Sigma). Cells were seeded into 96-well plates (Falcon-Primaria #3872) at a density of 10000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Endothelial Lipase Expression

Antisense modulation of endothelial lipase expression can be assayed in a variety of ways known in the art. For example, endothelial lipase mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of endothelial lipase can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to endothelial lipase can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and in vivo Studies for the Use of Endothelial Lipase Inhibitors Phenotypic Assays Once endothelial lipase inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of endothelial lipase in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with endothelial lipase inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the endothelial lipase inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or endothelial lipase inhibitor. Furthermore, to prevent the doctors from being biased in treatments, they are not informed as to whether the medication they are administering is a endothelial lipase inhibitor or a placebo. Using this randomization approach, each volunteer has the same chance of being given either the new treatment or the placebo.

Volunteers receive either the endothelial lipase inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding endothelial lipase or endothelial lipase protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and endothelial lipase inhibitor treatment. In general, the volunteers treated with placebo have little or no response to treatment, whereas the volunteers treated with the endothelial lipase inhibitor show positive trends in their disease state or condition index at the conclusion of the study.

Example 12

RNA Isolation

Poly(A)+ mRNA Isolation

Poly(A)+ mRNA was isolated according to Miura et al., (*Clin. Chem*., 1996, 42, 1758-1764). Other methods for poly (A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth, medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Endothelial Lipase mRNA Levels

Quantitation of endothelial lipase mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5× PCR buffer minus $MgCl_2$, 6.6 mM $MgCl_2$, 375 μM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human endothelial lipase were designed to hybridize to a human endothelial lipase sequence, using published sequence information (GenBank accession number NM_006033.1, incorporated herein as SEQ ID NO:4). For human endothelial lipase the PCR primers were:

forward primer: CCGGACGGGAGCTGAATAT (SEQ ID NO: 5) reverse primer: CAGTTTCCGCTGGGTTTCC (SEQ ID NO: 6) and the PCR probe was: FAM-AGGCGCATCCGGGTGAAGTC-TAMRA (SEQ ID NO: 7) where FAM is the fluorescent dye and TAMRA is the quencher dye. For human GAPDH the PCR primers were: forward primer: GAAGGTGAAGGTCGGAGTC(SEQ ID NO:8) reverse primer: GAAGATGGTGATGGGATTTC GGGTCTCGCTCCTGGAAGAT(SEQ ID NO:9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse endothelial lipase were designed to hybridize to a mouse endothelial lipase sequence, using published sequence information (GenBank accession number BC020991.1, incorporated herein as SEQ ID NO:11). For mouse endothelial lipase the PCR primers were:

forward primer: GCTGAATGCCACAAACACCTT (SEQ ID NO:12) reverse primer: CAGGTAAGTCGCATCTTCAAGAGA (SEQ ID NO: 13) and the PCR probe was: FAM-CTTGTCTACACTGAGGAGGACTTGGGCG-TAMRA (SEQ ID NO: 14) where FAM is the fluorescent reporter dye and TAMRA is the quencher dye. For mouse GAPDH the PCR primers were:

forward primer: GGCAAATTCAACGGCACAGT(SEQ ID NO:15) reverse primer: GGGTCTCGCTCCTGGAAGAT (SEQ ID NO:16) and the PCR probe was: 5' JOE-AAGGCCGAGAATGGGAAGCTTGTCATC-TAMRA 3' (SEQ ID NO: 17) where JOE is the fluorescent reporter dye and TAMRA is the quencher dye.

Example 14

Northern Blot Analysis of Endothelial Lipase mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human endothelial lipase, a human endothelial lipase specific probe was prepared by PCR using the forward primer CCGGACGGGAGCTGAATAT (SEQ ID NO: 5) and the reverse primer CAGTTTCCGCTGGGTTTCC (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse endothelial lipase, a mouse endothelial lipase specific probe was prepared by PCR using the forward primer GCTGAATGCCACAAACACCTT (SEQ ID NO: 12) and the reverse primer CAGGTAAGTCGCATCTTCAAGAGA (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Endothelial Lipase Expression by Chimeric Phosphorothioate Oligonucleotides Having 2'-MOE Wings and a Deoxy Gap In accordance with the present invention, a series of antisense compounds were designed to target different regions of the human endothelial lipase RNA, using published sequences (GenBank accession number NM_006033.1, incorporated herein as SEQ ID NO: 4, a genomic sequence of endothelial lipase represented by the complement of residues 3262-78294 of GenBank accession number NT_025012.8, incorporated herein as SEQ ID NO: 18, GenBank accession number AW450414.1, the complement of which is incorporated herein as SEQ ID NO: 19, and GenBank accession number AI676039.1, the complement of which is incorporated herein as SEQ ID NO: 20). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on human endothelial lipase mRNA levels by quantitative real-time PCR as described in other examples herein. Data are averages from three experiments in which HuVEC cells were treated with oligonucleotides 259869-259946 (SEQ ID NOs: 21-98) of the present invention. The positive control for each datapoint is identified in the table by sequence ID number. If present, "N.D." indicates "no data".

TABLE 1

Inhibition of human endothelial lipase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 259869 | 5'UTR | 4 | 48 | tcaacggcttgccccagaac | 61 | 21 | 1 |
| 259870 | 5'UTR | 4 | 103 | ggtggaaaatgaaaacttgg | 11 | 22 | 1 |
| 259871 | 5'UTR | 4 | 218 | cccctcccaagaaacagaag | 46 | 23 | 1 |
| 259872 | Start Codon | 4 | 245 | ggagttgctcatcctgcccc | 29 | 24 | 1 |
| 259873 | Coding | 4 | 317 | ctctggaccaaaaggtacgg | 19 | 25 | 1 |
| 259874 | Coding | 4 | 342 | tgtggagcttatcttccagc | 70 | 26 | 1 |
| 259875 | Coding | 4 | 382 | ctcacagatggtttgacctc | 68 | 27 | 1 |
| 259876 | Coding | 4 | 437 | gacggagaggtagcatcctt | 53 | 28 | 1 |
| 259877 | Coding | 4 | 560 | cagggctgacacgagtttgt | 56 | 29 | 1 |
| 259878 | Coding | 4 | 641 | attgaccgcatccgtgtaaa | 63 | 30 | 1 |
| 259879 | Coding | 4 | 700 | tccttctcctgcagccagtc | 62 | 31 | 1 |
| 259880 | Coding | 4 | 702 | cgtccttctcctgcagccag | 66 | 32 | 1 |
| 259881 | Coding | 4 | 725 | gtggacattcccgagagaaa | 66 | 33 | 1 |
| 259882 | Coding | 4 | 747 | ctccgaggctgtagccgatc | 82 | 34 | 1 |
| 259883 | Coding | 4 | 830 | aaacatgggcccggcaggat | 53 | 35 | 1 |
| 259884 | Coding | 4 | 988 | cagcctggctggaagtcacc | 60 | 36 | 1 |
| 259885 | Coding | 4 | 1099 | tcctgattcaccagagagtc | 79 | 37 | 1 |
| 259886 | Coding | 4 | 1104 | gcttgtcctgattcaccaga | 84 | 38 | 1 |
| 259887 | Coding | 4 | 1112 | aaaactcggcttgtcctgat | 75 | 39 | 1 |
| 259888 | Coding | 4 | 1124 | gcactggaaggcaaaactcg | 84 | 40 | 1 |
| 259889 | Coding | 4 | 1142 | gaagcgattggagtcagtgc | 67 | 41 | 1 |
| 259890 | Coding | 4 | 1266 | tgaaaggcatgcctgcccgg | 82 | 42 | 1 |
| 259891 | Coding | 4 | 1283 | ctgataatggtaaactctga | 67 | 43 | 1 |
| 259892 | Coding | 4 | 1312 | ttcttgtaactgaagacatg | 82 | 44 | 1 |
| 259893 | Coding | 4 | 1343 | gacgtaaaaggtgggctcaa | 73 | 45 | 1 |
| 259894 | Coding | 4 | 1398 | gctccactatttccagtggc | 60 | 46 | 1 |
| 259895 | Coding | 4 | 1427 | gaaggtgttggtggcattct | 53 | 47 | 1 |
| 259896 | Coding | 4 | 1459 | aggtctcccaagtcctcctc | 56 | 48 | 1 |
| 259897 | Coding | 4 | 1491 | aggccccctcccaggtgagc | 21 | 49 | 1 |
| 259898 | Coding | 4 | 1532 | gtagctgcgaaactccttc | 48 | 50 | 1 |

TABLE 1-continued

Inhibition of human endothelial lipase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 259899 | Coding | 4 | 1571 | gatattcagctcccgtccgg | 70 | 51 | 1 |
| 259900 | Coding | 4 | 1619 | aaatgtcagtttccgctggg | 79 | 52 | 1 |
| 259901 | Coding | 4 | 1641 | tgttctcagggtcttctgta | 55 | 53 | 1 |
| 259902 | Coding | 4 | 1724 | cacagtgggactggtttcgt | 66 | 54 | 1 |
| 259903 | Stop Codon | 4 | 1743 | ggcaccctcagggaagctcc | 83 | 55 | 1 |
| 259904 | 3'UTR | 4 | 1771 | ttgctgccttgctggcaaga | 51 | 56 | 1 |
| 259905 | 3'UTR | 4 | 1817 | gtcctcagcagtaactttcc | 58 | 57 | 1 |
| 259906 | 3'UTR | 4 | 1966 | acagaggtttggagttagag | 68 | 58 | 1 |
| 259907 | 3'UTR | 4 | 2044 | ccaatccagtgtgcacgaga | 83 | 59 | 1 |
| 259908 | 3'UTR | 4 | 2107 | gggcctcttcggagccagcg | 61 | 60 | 1 |
| 259909 | 3'UTR | 4 | 2241 | caacccatgagaaccccaac | 36 | 61 | 1 |
| 259910 | 3'UTR | 4 | 2279 | aggacggaatggctaagacg | 57 | 62 | 1 |
| 259911 | 3'UTR | 4 | 2361 | caatagacatttgctcaatt | 82 | 63 | 1 |
| 259912 | 3'UTR | 4 | 2438 | atcccaactccactgggttc | 12 | 64 | 1 |
| 259913 | 3'UTR | 4 | 2496 | aggtgcctttccccatgcat | 63 | 65 | 1 |
| 259914 | 3'UTR | 4 | 2527 | tgcttatatcctatagcctc | 70 | 66 | 1 |
| 259915 | 3'UTR | 4 | 2552 | ccacttaaagcctcagggtc | 55 | 67 | 1 |
| 259916 | 3'UTR | 4 | 2635 | tagtgatcaaacacgtcact | 85 | 68 | 1 |
| 259917 | 3'UTR | 4 | 2752 | acatatgtcataacttctat | 68 | 69 | 1 |
| 259918 | 3'UTR | 4 | 2873 | caacaagaaaaggcactggt | 78 | 70 | 1 |
| 259919 | 3'UTR | 4 | 2918 | ttaattcaaatcaagatcta | 34 | 71 | 1 |
| 259920 | 3'UTR | 4 | 2980 | ctaattaggcaatgcataca | 69 | 72 | 1 |
| 259921 | 3'UTR | 4 | 3039 | ctcactaagcctcagttttg | 69 | 73 | 1 |
| 259922 | 3'UTR | 4 | 3085 | tggctgcaccactaactagt | 62 | 74 | 1 |
| 259923 | 3'UTR | 4 | 3118 | gactttgcctccaggaaatc | 40 | 75 | 1 |
| 259924 | 3'UTR | 4 | 3151 | ggctgcaaaagtcttcatgg | 57 | 76 | 1 |
| 259925 | 3'UTR | 4 | 3218 | atggatggctctatataaaa | 38 | 77 | 1 |
| 259926 | 3'UTR | 4 | 3237 | taaaagggcttaggatttta | 68 | 78 | 1 |
| 259927 | 3'UTR | 4 | 3264 | acagatgttctcctggttat | 76 | 79 | 1 |
| 259928 | 3'UTR | 4 | 3285 | ataaaaagtccaaccgttgg | 64 | 80 | 1 |
| 259929 | 3'UTR | 4 | 3301 | ctcccgaatctcagccataa | 86 | 81 | 1 |
| 259930 | 3'UTR | 4 | 3325 | ctctcctgcttggtgtcaca | 61 | 82 | 1 |
| 259931 | 3'UTR | 4 | 3335 | atcattcttcctctcctgct | 80 | 83 | 1 |
| 259932 | 3'UTR | 4 | 3386 | ggcacgatacagattaaaac | 85 | 84 | 1 |
| 259933 | 3'UTR | 4 | 3410 | gaagtttaacagtgatacaa | 76 | 85 | 1 |

TABLE 1-continued

Inhibition of human endothelial lipase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 259934 | 3'UTR | 4 | 3441 | ttgaaataagactcaactgg | 74 | 86 | 1 |
| 259935 | 3'UTR | 4 | 3796 | ccaaaactttttgagcacca | 71 | 87 | 1 |
| 259936 | Intron | 18 | 12206 | agaccttttactttttgcaa | 22 | 88 | 1 |
| 259937 | Intron | 18 | 28424 | cctagcctgggaacccaaac | 19 | 89 | 1 |
| 259938 | Intron: exon junction | 18 | 37297 | ggatccaaacctgcagcaga | 8 | 90 | 1 |
| 259939 | Intron: exon junction | 18 | 47525 | tgaaggttacctctgaaagg | 5 | 91 | 1 |
| 259940 | Intron: exon junction | 18 | 48229 | taatggtaaactgcagtgac | 53 | 92 | 1 |
| 259941 | Intron: exon junction | 18 | 49641 | aggcacttacttccgctggg | 61 | 93 | 1 |
| 259942 | Intron | 18 | 50496 | gtcatagatgacgaatgtaa | 72 | 94 | 1 |
| 259943 | Intron | 18 | 55242 | gaattctgccagcagactgc | 12 | 95 | 1 |
| 259944 | Intron | 18 | 29605 | ttcttaagaagattgggttt | 44 | 96 | 1 |
| 259945 | 3'UTR | 20 | 105 | atatacaattaaggcttcaa | 19 | 97 | 1 |
| 259946 | 3'UTR | 20 | 114 | agtatcattatatacaatta | 0 | 98 | 1 |

As shown in Table 1, SEQ ID NOs 21, 26, 27, 28, 29, 30, 31, 32, 33, 34, 35, 36, 37, 38, 39, 40, 41, 42, 43, 44, 45, 46, 47, 48, 51, 52, 53, 54, 55, 56, 57, 58, 59, 60, 62, 63, 65, 66, 67, 68, 69, 70, 72, 73, 74, 76, 78, 79, 80, 81, 82, 83, 84, 85, 86, 87, 92, 93 and 94 demonstrated at least 50% inhibition of human endothelial lipase expression in this assay and are therefore preferred. More preferred are SEQ ID NOs: 38, 68 and 84. The target regions to which these prefered sequences are complementary are herein referred to as "preferred target segments" and are therefore preferred for targeting by compounds of the present invention. These preferred target segments are shown in Table 3. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Endothelial Lipase Expression by Chimeric Phosphorothioate Oligonucleotides Having 2'-MOE Wings and a Deoxy Gap In accordance with the present invention, a second series of antisense compounds were designed to target different regions of the mouse endothelial lipase RNA, using published sequences (GenBank accession number BC020991.1, incorporated herein as SEQ ID NO: 11, and GenBank accession number AF118768.1, incorporated herein as SEQ ID NO: 99). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse endothelial lipase mRNA levels by quantitative real-time PCR as described in other examples herein. Data are averages from three experiments in which mouse primary hepatocytes were treated with oligonucleotides 261160-261233 (SEQ ID NOs: 100-173) of the present invention. The positive control for each datapoint is identified in the table by sequence ID number. If present, "N.D." indicates "no data".

TABLE 2

Inhibition of mouse endothelial lipase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 261160 | 5'UTR | 99 | 9 | ttcccagagccgctgcgaag | 65 | 100 | 1 |
| 261161 | 5'UTR | 99 | 93 | gaacctggaaggttggtagc | 60 | 101 | 1 |
| 261162 | 5'UTR | 99 | 158 | cctccagagactagaagtgg | 39 | 102 | 1 |
| 261163 | 5'UTR | 99 | 165 | actaaaacctccagagacta | 61 | 103 | 1 |
| 261164 | Start Codon | 99 | 267 | cgtgtttcgcatccttcccc | 80 | 104 | 1 |
| 261165 | Coding | 99 | 328 | aggttgtgatacttcccgcc | 60 | 105 | 1 |
| 261166 | Coding | 99 | 356 | tcatctcgcagcgacccctg | 47 | 106 | 1 |
| 261167 | Coding | 99 | 381 | tggtactccagtgggtttat | 65 | 107 | 1 |
| 261168 | Coding | 99 | 418 | tgcggatgttaaaagccaca | 50 | 108 | 1 |
| 261169 | Coding | 99 | 465 | gtcaccaagggagagattac | 68 | 109 | 1 |
| 261170 | Coding | 99 | 489 | gccacagttttctaagagtt | 57 | 110 | 1 |
| 261171 | Coding | 99 | 666 | gttattgactgcatccgtgt | 57 | 111 | 1 |
| 261172 | Coding | 99 | 674 | accctggtgttattgactgc | 64 | 112 | 1 |
| 261173 | Coding | 99 | 708 | ccagtcaagcatcccagcta | 54 | 113 | 1 |
| 261174 | Coding | 99 | 741 | gttcccaagagagaactctt | 30 | 114 | 1 |
| 261175 | Coding | 99 | 777 | cacgtgtgctccaaggctgt | 50 | 115 | 1 |
| 261176 | Coding | 99 | 907 | catccacaaagtctgcatcg | 59 | 116 | 1 |
| 261177 | Coding | 99 | 912 | caggacatccacaaagtctg | 46 | 117 | 1 |
| 261178 | Coding | 99 | 917 | gtatgcaggacatccacaaa | 34 | 118 | 1 |
| 261179 | Coding | 99 | 922 | tgtaggtatgcaggacatcc | 45 | 119 | 1 |
| 261180 | Coding | 99 | 927 | cagcgtgtaggtatgcagga | 66 | 120 | 1 |
| 261181 | Coding | 99 | 932 | aaggacagcgtgtaggtatg | 9 | 121 | 1 |
| 261182 | Coding | 99 | 937 | agccaaaggacagcgtgtag | 50 | 122 | 1 |
| 261183 | Coding | 99 | 942 | gctcaagccaaaggacagcg | 60 | 123 | 1 |
| 261184 | Coding | 99 | 947 | ccaatgctcaagccaaagga | 63 | 124 | 1 |
| 261185 | Coding | 99 | 952 | gaatcccaatgctcaagcca | 49 | 125 | 1 |
| 261186 | Coding | 99 | 957 | catccgaatcccaatgctca | 48 | 126 | 1 |
| 261187 | Coding | 99 | 980 | tagatgtcaatgtgacccac | 43 | 127 | 1 |
| 261188 | Coding | 99 | 985 | tgggatagatgtcaatgtga | 35 | 128 | 1 |
| 261189 | Coding | 99 | 991 | cgccattgggatagatgtca | 0 | 129 | 1 |
| 261190 | Coding | 99 | 1068 | tttcaccatctctgagattg | 54 | 130 | 1 |
| 261191 | Coding | 99 | 1098 | aaagaggtgtacggctcgct | 51 | 131 | 1 |
| 261192 | Coding | 99 | 1103 | tcgacaaagaggtgtacggc | 73 | 132 | 1 |
| 261193 | Coding | 99 | 1108 | gagagtcgacaaagaggtgt | 46 | 133 | 1 |
| 261194 | Coding | 99 | 1113 | caccagagagtcgacaaaga | 56 | 134 | 1 |

TABLE 2-continued

Inhibition of mouse endothelial lipase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 261195 | Coding | 99 | 1178 | cagattccccttttgaagcg | 65 | 135 | 1 |
| 261196 | Coding | 99 | 1214 | ccaatgttattacaacggtt | 63 | 136 | 1 |
| 261197 | Coding | 99 | 1318 | tgtgaactttcagctggtaa | 71 | 137 | 1 |
| 261198 | Coding | 99 | 1328 | taagagaacatgtgaacttt | 57 | 138 | 1 |
| 261199 | Coding | 99 | 1341 | cccactgttattgtaagaga | 59 | 139 | 1 |
| 261200 | Coding | 99 | 1412 | atttccaagggcaggttctg | 72 | 140 | 1 |
| 261201 | Coding | 99 | 1460 | gtgtagacaaggaaggtgtt | 79 | 141 | 1 |
| 261202 | Coding | 99 | 1482 | gagatcgcccaagtcctcct | 85 | 142 | 1 |
| 261203 | Coding | 99 | 1499 | gtaagtcgcatcttcaagag | 82 | 143 | 1 |
| 261204 | Coding | 99 | 1512 | taccccctcccaggtaagtc | 30 | 144 | 1 |
| 261205 | Coding | 99 | 1521 | ggaatgggctaccccctccc | 38 | 145 | 1 |
| 261206 | Coding | 99 | 1542 | ctcattccacaggttgcacc | 28 | 146 | 1 |
| 261207 | Coding | 99 | 1624 | gggtttccccagatttgaca | 56 | 147 | 1 |
| 261208 | Coding | 99 | 1703 | cacttgtgaaaccacagctc | 62 | 148 | 1 |
| 261209 | Coding | 99 | 1743 | aaagggactggttttgtttt | 38 | 149 | 1 |
| 261210 | Stop Codon | 99 | 1766 | ttgggccctcaggccaagtt | 10 | 150 | 1 |
| 261211 | 3'UTR | 99 | 1885 | ccagcaagcaagctcctcgt | 28 | 151 | 1 |
| 261212 | 3'UTR | 99 | 1956 | tcagcaagaacttcagcagt | 56 | 152 | 1 |
| 261213 | 3'UTR | 99 | 1978 | caaaggtttacagctagaat | 43 | 153 | 1 |
| 261214 | 3'UTR | 99 | 1994 | cttcctgcggcggcaacaaa | 63 | 154 | 1 |
| 261215 | 3'UTR | 99 | 2017 | gctcacacacaagctggcct | 33 | 155 | 1 |
| 261216 | 3'UTR | 99 | 2036 | gggctctggacactccagtg | 33 | 156 | 1 |
| 261217 | 3'UTR | 99 | 2085 | gctcacctagcgacagggag | 74 | 157 | 1 |
| 261218 | 3'UTR | 99 | 2118 | gccttgtgttccctgatgtt | 60 | 158 | 1 |
| 261219 | 3'UTR | 99 | 2136 | acacagggccacttcagagc | 64 | 159 | 1 |
| 261220 | 3'UTR | 99 | 2141 | cttccacacagggccacttc | 7 | 160 | 1 |
| 261221 | 3'UTR | 99 | 2167 | ttcagtgaggccaggcagct | 65 | 161 | 1 |
| 261222 | 3'UTR | 99 | 2172 | taaggttcagtgaggccagg | 54 | 162 | 1 |
| 261223 | 3'UTR | 99 | 2182 | gacttgtcactaaggttcag | 66 | 163 | 1 |
| 261224 | 3'UTR | 11 | 2150 | aatagaaccaggatccatca | 37 | 164 | 1 |
| 261225 | 3'UTR | 11 | 2480 | tctgctagagatcaagggtg | 51 | 165 | 1 |
| 261226 | 3'UTR | 11 | 2583 | gcgcagcaggtatgtagaac | 68 | 166 | 1 |
| 261227 | 3'UTR | 11 | 2760 | tcaaactactaaagggtgtc | 65 | 167 | 1 |
| 261228 | 3'UTR | 11 | 2920 | ccaggaaaccttgctgggtc | 69 | 168 | 1 |
| 261229 | 3'UTR | 11 | 2955 | atggagttacagaaaggatt | 48 | 169 | 1 |

TABLE 2-continued

Inhibition of mouse endothelial lipase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 261230 | 3'UTR | 11 | 3184 | acagatgcaaagaatgtgcg | 57 | 170 | 1 |
| 261231 | 3'UTR | 11 | 3201 | tataaagctggtacaataca | 51 | 171 | 1 |
| 261232 | 3'UTR | 11 | 3530 | aaaactaaccatagatttgt | 43 | 172 | 1 |
| 261233 | 3'UTR | 11 | 3559 | aaatcttgaaatcggttaat | 49 | 173 | 1 |

As shown in Table 2, SEQ ID NOs 100, 101, 103, 104, 105, 107, 108, 109, 110, 111, 112, 113, 115, 116, 120, 122, 123, 124, 130, 131, 132, 134, 135, 136, 137, 138, 139, 140, 141, 142, 143, 147, 148, 152, 154, 157, 158, 159, 161, 162, 163, 165, 166, 167, 168, 170 and 171 demonstrated at least 50% inhibition of mouse endothelial lipase expression in this experiment and are therefore preferred. More preferred are SEQ ID NOs: 104, 132 and 157. The target regions to which these preferred sequences are complementary are herein referred to as "preferred target segments" and are therefore preferred for targeting by compounds of the present invention. These preferred target segments are shown in Table 3. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

TABLE 3

Sequence and position of preferred target segments identified in endothelial lipase.

| SITEID | TARGET SEQ ID NO | TARGET SITE | SEQUENCE | REV COMP OF SEQ ID | ACTIVE IN | SEQ ID NO |
|---|---|---|---|---|---|---|
| 176327 | 4 | 48 | gttctggggcaagccgttga | 21 | *H. sapiens* | 174 |
| 176332 | 4 | 342 | gctggaagataagctccaca | 26 | *H. sapiens* | 175 |
| 176333 | 4 | 382 | gaggtcaaaccatctgtgag | 27 | *H. sapiens* | 176 |
| 176334 | 4 | 437 | aaggatgctacctctccgtc | 28 | *H. sapiens* | 177 |
| 176335 | 4 | 560 | acaaactcgtgtcagccctg | 29 | *H. sapiens* | 178 |
| 176336 | 4 | 641 | tttacacggatgcggtcaat | 30 | *H. sapiens* | 179 |
| 176337 | 4 | 700 | gactggctgcaggagaagga | 31 | *H. sapiens* | 180 |
| 176338 | 4 | 702 | ctggctgcaggagaaggacg | 32 | *H. sapiens* | 181 |
| 176339 | 4 | 725 | tttctctcgggaatgtccac | 33 | *H. sapiens* | 182 |
| 176340 | 4 | 747 | gatcggctacagcctcggag | 34 | *H. sapiens* | 183 |
| 176341 | 4 | 830 | atcctgccgggcccatgttt | 35 | *H. sapiens* | 184 |
| 176342 | 4 | 988 | ggtgacttccagccaggctg | 36 | *H. sapiens* | 185 |
| 176343 | 4 | 1099 | gactctctggtgaatcagga | 37 | *H. sapiens* | 186 |
| 176344 | 4 | 1104 | tctggtgaatcaggacaagc | 38 | *H. sapiens* | 187 |
| 176345 | 4 | 1112 | atcaggacaagccgagtttt | 39 | *H. sapiens* | 188 |
| 176346 | 4 | 1124 | cgagttttgccttccagtgc | 40 | *H. sapiens* | 189 |
| 176347 | 4 | 1142 | gcactgactccaatcgcttc | 41 | *H. sapiens* | 190 |
| 176348 | 4 | 1266 | ccgggcaggcatgcctttca | 42 | *H. sapiens* | 191 |
| 176349 | 4 | 1283 | tcagagtttaccattatcag | 43 | *H. sapiens* | 192 |

TABLE 3-continued

Sequence and position of preferred target segments identified in endothelial lipase.

| SITEID | TARGET SEQ ID NO | TARGET SITE | SEQUENCE | REV COMP OF SEQ ID | ACTIVE IN | SEQ ID NO |
|---|---|---|---|---|---|---|
| 176350 | 4 | 1312 | catgtcttcagttacaagaa | 44 | *H. sapiens* | 193 |
| 176351 | 4 | 1343 | ttgagcccaccttttacgtc | 45 | *H. sapiens* | 194 |
| 176352 | 4 | 1398 | gccactggaaatagtggagc | 46 | *H. sapiens* | 195 |
| 176353 | 4 | 1427 | agaatgccaccaacaccttc | 47 | *H. sapiens* | 196 |
| 176354 | 4 | 1459 | gaggaggacttgggagacct | 48 | *H. sapiens* | 197 |
| 176357 | 4 | 1571 | ccggacgggagctgaatatc | 51 | *H. sapiens* | 198 |
| 176358 | 4 | 1619 | cccagcggaaactgacattt | 52 | *H. sapiens* | 199 |
| 176359 | 4 | 1641 | tacagaagaccctgagaaca | 53 | *H. sapiens* | 200 |
| 176360 | 4 | 1724 | acgaaaccagtcccactgtg | 54 | *H. sapiens* | 201 |
| 176361 | 4 | 1743 | ggagcttccctgagggtgcc | 55 | *H. sapiens* | 202 |
| 176362 | 4 | 1771 | tcttgccagcaaggcagcaa | 56 | *H. sapiens* | 203 |
| 176363 | 4 | 1817 | ggaaagttactgctgaggac | 57 | *H. sapiens* | 204 |
| 176364 | 4 | 1966 | ctctaactccaaacctctgt | 58 | *H. sapiens* | 205 |
| 176365 | 4 | 2044 | tctcgtgcacactggattgg | 59 | *H. sapiens* | 206 |
| 176366 | 4 | 2107 | cgctggctccgaagaggccc | 60 | *H. sapiens* | 207 |
| 176368 | 4 | 2279 | cgtcttagccattccgtcct | 62 | *H. sapiens* | 208 |
| 176369 | 4 | 2361 | aattgagcaaatgtctattg | 63 | *H. sapiens* | 209 |
| 176371 | 4 | 2496 | atgcatggggaaaggcacct | 65 | *H. sapiens* | 210 |
| 176372 | 4 | 2527 | gaggctataggatataagca | 66 | *H. sapiens* | 211 |
| 176373 | 4 | 2552 | gaccctgaggctttaagtgg | 67 | *H. sapiens* | 212 |
| 176374 | 4 | 2635 | agtgacgtgtttgatcacta | 68 | *H. sapiens* | 213 |
| 176375 | 4 | 2752 | atagaagttatgacatatgt | 69 | *H. sapiens* | 214 |
| 176376 | 4 | 2873 | accagtgccttttcttgttg | 70 | *H. sapiens* | 215 |
| 176378 | 4 | 2980 | tgtatgcattgcctaattag | 72 | *H. sapiens* | 216 |
| 176379 | 4 | 3039 | caaaactgaggcttagtgag | 73 | *H. sapiens* | 217 |
| 176380 | 4 | 3085 | actagttagtggtgcagcca | 74 | *H. sapiens* | 218 |
| 176382 | 4 | 3151 | ccatgaagacttttgcagcc | 76 | *H. sapiens* | 219 |
| 176384 | 4 | 3237 | taaaatcctaagccctttta | 78 | *H. sapiens* | 220 |
| 176385 | 4 | 3264 | ataaccaggagaacatctgt | 79 | *H. sapiens* | 221 |
| 176386 | 4 | 3285 | ccaacggttggactttttat | 80 | *H. sapiens* | 222 |
| 176387 | 4 | 3301 | ttatggctgagattcgggag | 81 | *H. sapiens* | 223 |
| 176388 | 4 | 3325 | tgtgacaccaagcaggagag | 82 | *H. sapiens* | 224 |
| 176389 | 4 | 3335 | agcaggagaggaagaatgat | 83 | *H. sapiens* | 225 |
| 176390 | 4 | 3386 | gttttaatctgtatcgtgcc | 84 | *H. sapiens* | 226 |
| 176391 | 4 | 3410 | ttgtatcactgttaaacttc | 85 | *H. sapiens* | 227 |
| 176392 | 4 | 3441 | ccagttgagtcttatttcaa | 86 | *H. sapiens* | 228 |

TABLE 3-continued

Sequence and position of preferred target segments identified in endothelial lipase.

| SITEID | TARGET SEQ ID NO | TARGET SITE | SEQUENCE | REV COMP OF SEQ ID | ACTIVE IN | SEQ ID NO |
|---|---|---|---|---|---|---|
| 176393 | 4 | 3796 | tggtgctcaaaaagttttgg | 87 | *H. sapiens* | 229 |
| 176398 | 18 | 48229 | gtcactgcagtttaccatta | 92 | *H. sapiens* | 230 |
| 176399 | 18 | 49641 | cccagcggaagtaagtgcct | 93 | *H. sapiens* | 231 |
| 176400 | 18 | 50496 | ttacattcgtcatctatgac | 94 | *H. sapiens* | 232 |
| 177667 | 99 | 9 | cttcgcagcggctctgggaa | 100 | *M. musculus* | 233 |
| 177668 | 99 | 93 | gctaccaaccttccaggttc | 101 | *M. musculus* | 234 |
| 177670 | 99 | 165 | tagtctctggaggttttagt | 103 | *M. musculus* | 235 |
| 177671 | 99 | 267 | ggggaaggatgcgaaacacg | 104 | *M. musculus* | 236 |
| 177672 | 99 | 328 | ggcgggaagtatcacaacct | 105 | *M. musculus* | 237 |
| 177674 | 99 | 381 | ataaacccactggagtacca | 107 | *M. musculus* | 238 |
| 177675 | 99 | 418 | tgtggcttttaacatccgca | 108 | *M. musculus* | 239 |
| 177676 | 99 | 465 | gtaatctctcccttggtgac | 109 | *M. musculus* | 240 |
| 177677 | 99 | 489 | aactcttagaaaactgtggc | 110 | *M. musculus* | 241 |
| 177678 | 99 | 666 | acacggatgcagtcaataac | 111 | *M. musculus* | 242 |
| 177679 | 99 | 674 | gcagtcaataacaccagggt | 112 | *M. musculus* | 243 |
| 177680 | 99 | 708 | tagctgggatgcttgactgg | 113 | *M. musculus* | 244 |
| 177682 | 99 | 777 | acagccttggagcacacgtg | 115 | *M. musculus* | 245 |
| 177683 | 99 | 907 | cgatgcagactttgtggatg | 116 | *M. musculus* | 246 |
| 177687 | 99 | 927 | tcctgcatacctacacgctg | 120 | *M. musculus* | 247 |
| 177689 | 99 | 937 | ctacacgctgtcctttggct | 122 | *M. musculus* | 248 |
| 177690 | 99 | 942 | cgctgtcctttggcttgagc | 123 | *M. musculus* | 249 |
| 177691 | 99 | 947 | tcctttggcttgagcattgg | 124 | *M. musculus* | 250 |
| 177696 | 99 | 1068 | caatctcagagatggtgaaa | 130 | *M. musculus* | 251 |
| 177697 | 99 | 1098 | agcgagccgtacacctcttt | 131 | *M. musculus* | 252 |
| 177698 | 99 | 1103 | gccgtacacctctttgtcga | 132 | *M. musculus* | 253 |
| 177700 | 99 | 1113 | tctttgtcgactctctggtg | 134 | *M. musculus* | 254 |
| 177701 | 99 | 1178 | cgcttcaaaaggggaatctg | 135 | *M. musculus* | 255 |
| 177702 | 99 | 1214 | aaccgttgtaataacattgg | 136 | *M. musculus* | 256 |
| 177703 | 99 | 1318 | ttaccagctgaaagttcaca | 137 | *M. musculus* | 257 |
| 177704 | 99 | 1328 | aaagttcacatgttctctta | 138 | *M. musculus* | 258 |
| 177705 | 99 | 1341 | tctcttacaataacagtggg | 139 | *M. musculus* | 259 |
| 177706 | 99 | 1412 | cagaacctgcccttggaaat | 140 | *M. musculus* | 260 |
| 177707 | 99 | 1460 | aacaccttccttgtctacac | 141 | *M. musculus* | 261 |
| 177708 | 99 | 1482 | aggaggacttgggcgatctc | 142 | *M. musculus* | 262 |
| 177709 | 99 | 1499 | ctcttgaagatgcgacttac | 143 | *M. musculus* | 263 |
| 177713 | 99 | 1624 | tgtcaaatctggggaaaccc | 147 | *M. musculus* | 264 |

TABLE 3-continued

Sequence and position of preferred target segments identified in endothelial lipase.

| SITEID | TARGET SEQ ID NO | TARGET SITE | SEQUENCE | REV COMP OF SEQ ID | ACTIVE IN | SEQ ID NO |
|---|---|---|---|---|---|---|
| 177714 | 99 | 1703 | gagctgtggtttcacaagtg | 148 | *M. musculus* | 265 |
| 177718 | 99 | 1956 | actgctgaagttcttgctga | 152 | *M. musculus* | 266 |
| 177720 | 99 | 1994 | tttgttgccgccgcaggaag | 154 | *M. musculus* | 267 |
| 177723 | 99 | 2085 | ctccctgtcgctaggtgagc | 157 | *M. musculus* | 268 |
| 177724 | 99 | 2118 | aacatcagggaacacaaggc | 158 | *M. musculus* | 269 |
| 177725 | 99 | 2136 | gctctgaagtggccctgtgt | 159 | *M. musculus* | 270 |
| 177727 | 99 | 2167 | agctgcctggcctcactgaa | 161 | *M. musculus* | 271 |
| 177728 | 99 | 2172 | cctggcctcactgaacctta | 162 | *M. musculus* | 272 |
| 177729 | 99 | 2182 | ctgaaccttagtgacaagtc | 163 | *M. musculus* | 273 |
| 177731 | 11 | 2480 | cacccttgatctctagcaga | 165 | *M. musculus* | 274 |
| 177732 | 11 | 2583 | gttctacatacctgctgcgc | 166 | *M. musculus* | 275 |
| 177733 | 11 | 2760 | gacaccctttagtagtttga | 167 | *M. musculus* | 276 |
| 177734 | 11 | 2920 | gacccagcaaggtttcctgg | 168 | *M. musculus* | 277 |
| 177736 | 11 | 3184 | cgcacattctttgcatctgt | 170 | *M. musculus* | 278 |
| 177737 | 11 | 3201 | tgtattgtaccagctttata | 171 | *M. musculus* | 279 |

As these “preferred target segments” have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of endothelial lipase.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 17

Western Blot Analysis of Endothelial Lipase Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to endothelial lipase is used, with a radiolabeled or fluorescently labeled secondary antibody directed against the primary antibody species. Bands are visualized using a PHOSPHORIMAGER™ (Molecular Dynamics, Sunnyvale Calif.).

What is claimed is:

1. A composition comprising a single-stranded antisense compound or a salt form thereof, wherein the single-stranded antisense compound is 15 to 30 nucleobases in length and is at least 90% complementary within nucleobases 1099 to 1143 of SEQ ID NO:4, and a pharmaceutically acceptable carrier or diluent.

2. The composition of claim 1, wherein the antisense compound comprises a DNA oligonucleotide.

3. The composition of claim 1, wherein the antisense compound comprises an RNA oligonucleotide.

4. The composition of claim 1, wherein the antisense compound comprises a chimeric antisense oligonucleotide.

5. The composition of claim 1, wherein the antisense compound comprises at least one modified internucleoside linkage, sugar moiety, or nucleobase.

6. The composition of claim 1, wherein the antisense compound comprises at least one 2'-O-methoxyethyl sugar moiety.

7. The composition of claim 1, wherein the antisense compound comprises at least one phosphorothioate internucleoside linkage.

8. The composition of claim 1, wherein the antisense compound comprises at least one 5-methylcytosine.

9. The composition of claim 4, wherein the chimeric antisense oligonucleotide comprises a plurality of 2'-deoxynucleotides flanked on each side by at least one 2'-O-methoxyethyl nucleotide.

10. A composition comprising a single-stranded antisense compound or a salt form thereof, wherein the single-stranded antisense compound is 15 to 30 nucleobases in length and is at least 90% complementary to at least 8 consecutive nucleobases within nucleobases 1104-1123 of SEQ ID NO:4, wherein the single-stranded antisense compound is a chimeric antisense oligonucleotide, and a pharmaceutically acceptable carrier or diluent.

11. The composition of claim 10, wherein the antisense compound comprises at least one modified internucleoside linkage, sugar moiety, or nucleobase.

12. The composition of claim 11, wherein the modified internucleoside linkage is a phosphorothioate linkage.

13. The composition of claim 11, wherein the modified sugar moiety is a 2'-O-methoxyethyl sugar moiety.

14. The composition of claim 11, wherein the modified nucleobase is a 5-methylcytidine.

15. The composition of claim 10, wherein the antisense compound comprises a plurality of 2'-deoxynucleotides flanked on each side by at least one 2'-O-methoxyethyl nucleotide.

16. The composition of claim 1, wherein the antisense compound is at least 95% complementary within nucleobases 1099 to 1143 of SEQ ID NO:4.

17. The composition of claim 1, wherein the antisense compound is fully complementary within nucleobases 1099 to 1143 of SEQ ID NO:4.

18. The composition of claim 10, wherein the antisense compound is at least 95% complementary to at least 8 consecutive nucleobases within nucleobases 1104-1123 of SEQ ID NO:4.

19. The composition of claim 10, wherein the antisense compound is fully complementary to at least 8 consecutive nucleobases within nucleobases 1104-1123 of SEQ ID NO:4.

20. The composition of claim 15, wherein the antisense compound comprises ten 2'-deoxynucleotides flanked on each side by five 2'-O-methoxyethyl nucleotides.

21. The composition of claim 20, wherein the antisense compound is 20 nucleobases in length.

* * * * *

SEQUENCE LISTING

```
<160> NUMBER OF SEQ ID NOS: 279

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
```

-continued

```
tccgtcatcg ctcctcaggg                                                    20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2

gtgcgcgcga gcccgaaatc                                                    20


<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3

atgcattctg cccccaagga                                                    20


<210> SEQ ID NO 4
<211> LENGTH: 3927
<212> TYPE: DNA
<213> ORGANISM: H. sapiens
<220> FEATURE:
<220> FEATURE:
<221> NAME/KEY: CDS
<222> LOCATION: (253)...(1755)

<400> SEQUENCE: 4

agcagcgagt ccttgcctcc cggcggctca ggacgagggc agatctcgtt ctggggcaag     60

ccgttgacac tcgctccctg ccaccgcccg ggctccgtgc cgccaagttt tcattttcca    120

ccttctctgc ctccagtccc ccagcccctg gccgagagaa gggtcttacc ggccgggatt    180

gctggaaaca ccaagaggtg gtttttgttt tttaaaactt ctgtttcttg ggagggggtg    240

tggcggggca gg atg agc aac tcc gtt cct ctg ctc tgt ttc tgg agc ctc    291
              Met Ser Asn Ser Val Pro Leu Leu Cys Phe Trp Ser Leu
                1               5                  10

tgc tat tgc ttt gct gcg ggg agc ccc gta cct ttt ggt cca gag gga      339
Cys Tyr Cys Phe Ala Ala Gly Ser Pro Val Pro Phe Gly Pro Glu Gly
     15                  20                  25

cgg ctg gaa gat aag ctc cac aaa ccc aaa gct aca cag act gag gtc      387
Arg Leu Glu Asp Lys Leu His Lys Pro Lys Ala Thr Gln Thr Glu Val
 30                  35                  40                  45

aaa cca tct gtg agg ttt aac ctc cgc acc tcc aag gac cca gag cat      435
Lys Pro Ser Val Arg Phe Asn Leu Arg Thr Ser Lys Asp Pro Glu His
                 50                  55                  60

gaa gga tgc tac ctc tcc gtc ggc cac agc cag ccc tta gaa gac tgc      483
Glu Gly Cys Tyr Leu Ser Val Gly His Ser Gln Pro Leu Glu Asp Cys
             65                  70                  75

agt ttc aac atg aca gct aaa acc ttt ttc atc att cac gga tgg acg      531
Ser Phe Asn Met Thr Ala Lys Thr Phe Phe Ile Ile His Gly Trp Thr
         80                  85                  90

atg agc ggt atc ttt gaa aac tgg ctg cac aaa ctc gtg tca gcc ctg      579
Met Ser Gly Ile Phe Glu Asn Trp Leu His Lys Leu Val Ser Ala Leu
     95                 100                 105

cac aca aga gag aaa gac gcc aat gta gtt gtg gtt gac tgg ctc ccc      627
His Thr Arg Glu Lys Asp Ala Asn Val Val Val Val Asp Trp Leu Pro
110                 115                 120                 125
```

-continued

```
ctg gcc cac cag ctt tac acg gat gcg gtc aat aat acc agg gtg gtg      675
Leu Ala His Gln Leu Tyr Thr Asp Ala Val Asn Asn Thr Arg Val Val
                130                 135                 140

gga cac agc att gcc agg atg ctc gac tgg ctg cag gag aag gac gat      723
Gly His Ser Ile Ala Arg Met Leu Asp Trp Leu Gln Glu Lys Asp Asp
            145                 150                 155

ttt tct ctc ggg aat gtc cac ttg atc ggc tac agc ctc gga gcg cac      771
Phe Ser Leu Gly Asn Val His Leu Ile Gly Tyr Ser Leu Gly Ala His
        160                 165                 170

gtg gcc ggg tat gca ggc aac ttc gtg aaa gga acg gtg ggc cga atc      819
Val Ala Gly Tyr Ala Gly Asn Phe Val Lys Gly Thr Val Gly Arg Ile
    175                 180                 185

aca ggt ttg gat cct gcc ggg ccc atg ttt gaa ggg gcc gac atc cac      867
Thr Gly Leu Asp Pro Ala Gly Pro Met Phe Glu Gly Ala Asp Ile His
190                 195                 200                 205

aag agg ctc tct ccg gac gat gca gat ttt gtg gat gtc ctc cac acc      915
Lys Arg Leu Ser Pro Asp Asp Ala Asp Phe Val Asp Val Leu His Thr
                210                 215                 220

tac acg cgt tcc ttc ggc ttg agc att ggt att cag atg cct gtg ggc      963
Tyr Thr Arg Ser Phe Gly Leu Ser Ile Gly Ile Gln Met Pro Val Gly
            225                 230                 235

cac att gac atc tac ccc aat ggg ggt gac ttc cag cca ggc tgt gga     1011
His Ile Asp Ile Tyr Pro Asn Gly Gly Asp Phe Gln Pro Gly Cys Gly
        240                 245                 250

ctc aac gat gtc ttg gga tca att gca tat gga aca atc aca gag gtg     1059
Leu Asn Asp Val Leu Gly Ser Ile Ala Tyr Gly Thr Ile Thr Glu Val
    255                 260                 265

gta aaa tgt gag cat gag cga gcc gtc cac ctc ttt gtt gac tct ctg     1107
Val Lys Cys Glu His Glu Arg Ala Val His Leu Phe Val Asp Ser Leu
270                 275                 280                 285

gtg aat cag gac aag ccg agt ttt gcc ttc cag tgc act gac tcc aat     1155
Val Asn Gln Asp Lys Pro Ser Phe Ala Phe Gln Cys Thr Asp Ser Asn
                290                 295                 300

cgc ttc aaa aag ggg atc tgt ctg agc tgc cgc aag aac cgt tgt aat     1203
Arg Phe Lys Lys Gly Ile Cys Leu Ser Cys Arg Lys Asn Arg Cys Asn
            305                 310                 315

agc att ggc tac aat gcc aag aaa atg agg aac aag agg aac agc aaa     1251
Ser Ile Gly Tyr Asn Ala Lys Lys Met Arg Asn Lys Arg Asn Ser Lys
        320                 325                 330

atg tac cta aaa acc cgg gca ggc atg cct ttc aga gtt tac cat tat     1299
Met Tyr Leu Lys Thr Arg Ala Gly Met Pro Phe Arg Val Tyr His Tyr
    335                 340                 345

cag atg aaa atc cat gtc ttc agt tac aag aac atg gga gaa att gag     1347
Gln Met Lys Ile His Val Phe Ser Tyr Lys Asn Met Gly Glu Ile Glu
350                 355                 360                 365

ccc acc ttt tac gtc acc ctt tat ggc act aat gca gat tcc cag act     1395
Pro Thr Phe Tyr Val Thr Leu Tyr Gly Thr Asn Ala Asp Ser Gln Thr
                370                 375                 380

ctg cca ctg gaa ata gtg gag cgg atc gag cag aat gcc acc aac acc     1443
Leu Pro Leu Glu Ile Val Glu Arg Ile Glu Gln Asn Ala Thr Asn Thr
            385                 390                 395

ttc ctg gtc tac acc gag gag gac ttg gga gac ctc ttg aag atc cag     1491
Phe Leu Val Tyr Thr Glu Glu Asp Leu Gly Asp Leu Leu Lys Ile Gln
        400                 405                 410

ctc acc tgg gag ggg gcc tct cag tct tgg tac aac ctg tgg aag gag     1539
Leu Thr Trp Glu Gly Ala Ser Gln Ser Trp Tyr Asn Leu Trp Lys Glu
    415                 420                 425

ttt cgc agc tac ctg tct caa ccc cgc aac ccc gga cgg gag ctg aat     1587
Phe Arg Ser Tyr Leu Ser Gln Pro Arg Asn Pro Gly Arg Glu Leu Asn
430                 435                 440                 445
```

-continued

```
atc agg cgc atc cgg gtg aag tct ggg gaa acc cag cgg aaa ctg aca     1635
Ile Arg Arg Ile Arg Val Lys Ser Gly Glu Thr Gln Arg Lys Leu Thr
            450                 455                 460

ttt tgt aca gaa gac cct gag aac acc agc ata tcc cca ggc cgg gag     1683
Phe Cys Thr Glu Asp Pro Glu Asn Thr Ser Ile Ser Pro Gly Arg Glu
        465                 470                 475

ctc tgg ttt cgc aag tgt cgg gat ggc tgg agg atg aaa aac gaa acc     1731
Leu Trp Phe Arg Lys Cys Arg Asp Gly Trp Arg Met Lys Asn Glu Thr
    480                 485                 490

agt ccc act gtg gag ctt ccc tga gggtgcccgg gcaagtcttg ccagcaaggc    1785
Ser Pro Thr Val Glu Leu Pro
495                 500

agcaagactt cctgctatcc aagcccatgg aggaaagtta ctgctgagga cccacccaat   1845

ggaaggattc ttctcagcct tgaccctgga gcactgggaa caactggtct cctgtgatgg   1905

ctgggactcc tcgcgggagg ggactgcgct gctatagctc ttgctgcctc tcttgaatag   1965

ctctaactcc aaacctctgt ccacacctcc agagcaccaa gtccagattt gtgtgtaagc   2025

agctgggtgc ctggggcctc tcgtgcacac tggattggtt tctcagttgc tgggcgagcc   2085

tgtactctgc ctgacgagga acgctggctc cgaagaggcc ctgtgtagaa ggctgtcagc   2145

tgctcagcct gctttgagcc tcagtgagaa gtccttccga caggagctga ctcatgtcag   2205

gatggcaggc ctggtatctt gctcgggccc tagctgttgg ggttctcatg ggttgcactg   2265

accatactgc ttacgtctta gccattccgt cctgctcccc agctcactct ctgaagcaca   2325

catcattggc tttcctattt ttctgttcat tttttaattg agcaaatgtc tattgaacac   2385

ttaaaattaa ttagaatgtg gtaatggaca tattactgag cctctccatt tggaacccag   2445

tggagttggg atttctagac cctctttctg tttggatggt gtatgtgtat atgcatgggg   2505

aaaggcacct ggggcctggg ggaggctata ggatataagc attagggacc ctgaggcttt   2565

aagtggtttc tatttcttct tagttattat gtgccacctt cttagttatt atgtgccacc   2625

tcccctatga gtgacgtgtt tgatcactag cagaatagca agcagagtat cattcatgct   2685

ggggccagaa tgatggccgg ttgccagata taactgcttt ggagcaaatc tcttctgttt   2745

agagagatag aagttatgac atatgtaata cacatctgtg tacacagaaa ccggcacctg   2805

ccagacagag ctggttctaa gatttaatac agtgcttttt ttcctctttg aaatatttta   2865

ctttaatacc agtgcctttt cttgttgaac ttcttggaaa agccaccaat tctagatctt   2925

gatttgaatt aatacacaca atatctgaga cacttacact tttcaaaaga tttgtgtatg   2985

cattgcctaa ttagagtagg gggagaaggg caactattat tatccctatt ttacaaaact   3045

gaggcttagt gaggttcagc cacatgccta gacttatata ctagttagtg gtgcagccag   3105

ggagaggact cagatttcct ggaggcaaag tctatctctg aaactccatg aagacttttg   3165

cagccagttc ccaccaatat gccccagacg tgagacaaac aaggactttt ttttttatat   3225

agagccatcc ataaaatcct aagccctttt attaatgtat aaccaggaga acatctgtgc   3285

caacggttgg actttttatg gctgagattc gggaggaagt gtgacaccaa gcaggagagg   3345

aagaatgatt ttctttgtac ttaggttttc taaggacatt gttttaatct gtatcgtgcc   3405

aaagttgtat cactgttaaa cttctgaaga cataaccagt tgagtcttat ttcaagatat   3465

gttctcaagc caattgtgtg cttctcttgt ttctgtgatt gctttctagc caaagcgaag   3525

cttgtacagg ttgagtatcc cttatccaaa atgcttggaa ccagaagtgt ttcaaatttt   3585

agattatttt cagattttgg aatgtttgca tatacataat gagatatttt gggaatagga   3645
```

-continued cccgagccta aacacaaaat tcattgatgt gtcagttaca ccttatccac atagcctgag 3705 ggtaatttta tacgatattt taaatagttg tgtacatgaa gcatggtttg tggtaactta 3765 tgtgaggggt tttcccattt tttgtcttgt tggtgctcaa aaagttttgg attttggagc 3825 atttcggatt ttggattttt ggattagggt tgctcaaccc atattattgg ctgtacatcc 3885 tggtcacttc tgacttctgt ttttactaat ggaagctttg ca 3927

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
ccggacggga gctgaatat 19

<210> SEQ ID NO 6
<211> LENGTH: 19
<212> TYPE: DNA
<213> ORGANISM: Artificial Sequence
<220> FEATURE:
<223> OTHER INFORMATION: PCR Primer

<400> SEQUENCE: 6
cagtttccgc tgggtttcc 19

<210> SEQ ID NO 7
<211> LENGTH: 20
<212> TYPE: DNA
<213> ORGANISM: Artificial Sequence
<220> FEATURE:
<223> OTHER INFORMATION: PCR Probe

<400> SEQUENCE: 7
aggcgcatcc gggtgaagtc 20

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc 19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc 20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10

-continued

```
caagcttccc gttctcagcc                                                  20


<210> SEQ ID NO 11
<211> LENGTH: 3610
<212> TYPE: DNA
<213> ORGANISM: Mus musculus
<220> FEATURE:
<221> NAME/KEY: CDS
<222> LOCATION: (144)...(1646)

<400> SEQUENCE: 11

ccacgcgtcc gcgacacccg gcctgtccac ttctagtctc tggaggtttt agtggtttca      60

aaccaaacca acccaaacca acccaacaac aaaaaagccc aaaccaaaaa cctgcttgag     120

aggagggggc gtggcgggga agg atg cga aac acg gtt ttc ctg ctc ggc ttt     173
                          Met Arg Asn Thr Val Phe Leu Leu Gly Phe
                           1               5                  10

tgg agc gtc tat tgt tac ttc ccg gcg gga agt atc aca acc ttg cgt       221
Trp Ser Val Tyr Cys Tyr Phe Pro Ala Gly Ser Ile Thr Thr Leu Arg
                15                  20                  25

ccc gag ggg tcg ctg cga gat gag cat cat aaa ccc act gga gta cca       269
Pro Glu Gly Ser Leu Arg Asp Glu His His Lys Pro Thr Gly Val Pro
            30                  35                  40

gct acc gcc aga ccc tct gtg gct ttt aac atc cgc act tct aag gac       317
Ala Thr Ala Arg Pro Ser Val Ala Phe Asn Ile Arg Thr Ser Lys Asp
        45                  50                  55

cca gag cag gaa ggg tgt aat ctc tcc ctt ggt gac agc aaa ctc tta       365
Pro Glu Gln Glu Gly Cys Asn Leu Ser Leu Gly Asp Ser Lys Leu Leu
    60                  65                  70

gaa aac tgt ggc ttc aac atg aca gcc aaa acc ttc ttc atc att cat       413
Glu Asn Cys Gly Phe Asn Met Thr Ala Lys Thr Phe Phe Ile Ile His
 75                  80                  85                  90

gga tgg acg atg agt ggc atg ttt gag agc tgg ctg cat aaa ctt gta       461
Gly Trp Thr Met Ser Gly Met Phe Glu Ser Trp Leu His Lys Leu Val
                95                 100                 105

tca gcc ctg cag atg aga gag aaa gat gct aac gtc gtg gtg gtt gac       509
Ser Ala Leu Gln Met Arg Glu Lys Asp Ala Asn Val Val Val Val Asp
            110                 115                 120

tgg ctg ccc ctg gct cat cag ctg tac acg gat gca gtc aat aac acc       557
Trp Leu Pro Leu Ala His Gln Leu Tyr Thr Asp Ala Val Asn Asn Thr
        125                 130                 135

agg gtg gtg gga cag aga gta gct ggg atg ctt gac tgg ctg cag gag       605
Arg Val Val Gly Gln Arg Val Ala Gly Met Leu Asp Trp Leu Gln Glu
    140                 145                 150

aag gaa gag ttc tct ctt ggg aac gtt cac ttg att ggc tac agc ctt       653
Lys Glu Glu Phe Ser Leu Gly Asn Val His Leu Ile Gly Tyr Ser Leu
155                 160                 165                 170

gga gca cac gtg gct gga tac gct ggc aac ttt gtg aaa gga aca gtg       701
Gly Ala His Val Ala Gly Tyr Ala Gly Asn Phe Val Lys Gly Thr Val
                175                 180                 185

ggc agg atc act ggt ctg gat ccc gcg ggt ccc atg ttt gaa ggg gtg       749
Gly Arg Ile Thr Gly Leu Asp Pro Ala Gly Pro Met Phe Glu Gly Val
            190                 195                 200

gac atc aac aga agg ctg tcc ccg gac gat gca gac ttt gtg gat gtc       797
Asp Ile Asn Arg Arg Leu Ser Pro Asp Asp Ala Asp Phe Val Asp Val
        205                 210                 215

ctg cat acc tac acg ctg tcc ttt ggc ttg agc att ggg att cgg atg       845
Leu His Thr Tyr Thr Leu Ser Phe Gly Leu Ser Ile Gly Ile Arg Met
    220                 225                 230

cct gtg ggt cac att gac atc tat ccc aat ggc ggt gac ttc cag cca       893
```

-continued

```
Pro Val Gly His Ile Asp Ile Tyr Pro Asn Gly Gly Asp Phe Gln Pro
235                 240                 245                 250

ggc tgt gga ttc aat gat gtc atc gga tct ttt gca tat gga aca atc      941
Gly Cys Gly Phe Asn Asp Val Ile Gly Ser Phe Ala Tyr Gly Thr Ile
                255                 260                 265

tca gag atg gtg aaa tgc gag cac gag cga gcc gta cac ctc ttt gtc      989
Ser Glu Met Val Lys Cys Glu His Glu Arg Ala Val His Leu Phe Val
            270                 275                 280

gac tct ctg gtg aat cag gac aag ccc agc ttt gcc ttc cag tgc aca     1037
Asp Ser Leu Val Asn Gln Asp Lys Pro Ser Phe Ala Phe Gln Cys Thr
        285                 290                 295

gac tcc agc cgc ttc aaa agg gga atc tgc ctc agc tgc cgg aag aac     1085
Asp Ser Ser Arg Phe Lys Arg Gly Ile Cys Leu Ser Cys Arg Lys Asn
    300                 305                 310

cgt tgt aat aac att ggc tac aac gcc aag aaa atg aga aag aag agg     1133
Arg Cys Asn Asn Ile Gly Tyr Asn Ala Lys Lys Met Arg Lys Lys Arg
315                 320                 325                 330

aat agc aaa atg tat tta aaa acc cgg gct ggc atg cct ttc aaa gtt     1181
Asn Ser Lys Met Tyr Leu Lys Thr Arg Ala Gly Met Pro Phe Lys Val
                335                 340                 345

tac cat tac cag ctg aaa gtt cac atg ttc tct tac aat aac agt ggg     1229
Tyr His Tyr Gln Leu Lys Val His Met Phe Ser Tyr Asn Asn Ser Gly
            350                 355                 360

gac acc cag ccc acc ctc tac att acc ctg tat ggt agc aac gca gac     1277
Asp Thr Gln Pro Thr Leu Tyr Ile Thr Leu Tyr Gly Ser Asn Ala Asp
        365                 370                 375

tcc cag aac ctg ccc ttg gaa ata gtg gag aag att gag ctg aat gcc     1325
Ser Gln Asn Leu Pro Leu Glu Ile Val Glu Lys Ile Glu Leu Asn Ala
    380                 385                 390

aca aac acc ttc ctt gtc tac act gag gag gac ttg ggc gat ctc ttg     1373
Thr Asn Thr Phe Leu Val Tyr Thr Glu Glu Asp Leu Gly Asp Leu Leu
395                 400                 405                 410

aag atg cga ctt acc tgg gag ggg gta gcc cat tcc tgg tac aac ctg     1421
Lys Met Arg Leu Thr Trp Glu Gly Val Ala His Ser Trp Tyr Asn Leu
                415                 420                 425

tgg aat gag ttt cgc aac tac ctg tct caa ccc agc aac ccc tcg agg     1469
Trp Asn Glu Phe Arg Asn Tyr Leu Ser Gln Pro Ser Asn Pro Ser Arg
            430                 435                 440

gag ctg tac atc cgg cga att cgt gtc aaa tct ggg gaa acc cag cgc     1517
Glu Leu Tyr Ile Arg Arg Ile Arg Val Lys Ser Gly Glu Thr Gln Arg
        445                 450                 455

aaa gtg aca ttt tgc act caa gac cca acg aag agt agc atc tcc cct     1565
Lys Val Thr Phe Cys Thr Gln Asp Pro Thr Lys Ser Ser Ile Ser Pro
    460                 465                 470

ggc cag gag ctg tgg ttt cac aag tgt cag gat ggc tgg aaa atg aaa     1613
Gly Gln Glu Leu Trp Phe His Lys Cys Gln Asp Gly Trp Lys Met Lys
475                 480                 485                 490

aac aaa acc agt ccc ttt gtg aac ttg gcc tga gggcccaaga agtcctggcg   1666
Asn Lys Thr Ser Pro Phe Val Asn Leu Ala  *
                495                 500

tccacaccca caccccactg tccacgcaca tggaggaaaa gttactgctg aagacccact   1726

cgatggacga tctcagcctt gagccccacg aggagcttgc ttgctgggct catcctgtct   1786

cccctgacaa ctgtgacttc tcctggagag gcctgtgcac tgctgaagtt cttgctgatg   1846

attctagctg taaacctttg ttgccgccgc aggaagctga ggccagcttg tgtgtgagca   1906

ctggagtgtc cagagccctg cacactcggg gtgggggcgg gggtactctc cctgtcgcta   1966

ggtgagcact ggctttgtcc aacatcaggg aacacaaggc tctgaagtgg ccctgtgtgg   2026
```

-continued

```
aaggttggca gctgcctggc ctcactgaac cttagtgaca agtctttgcc tcaggagctg   2086

actcatgcca tagagagggg actgtagacc aggctggggc tgctgccctc ccacacgagg   2146

tactgatgga tcctggttct attctgggta tttcatcctg ccttccagag caccttctga   2206

agttcacatc gttggcattt cctttttatg ttatgcatac tttggctgaa caaacattta   2266

ttgggcactt cagctcatta gcaccaggca tgtatagaca catgactcaa cttcagcatt   2326

tggagccagc gagaccagga tccctggaat ctctcaagtt cactggcccc tgagaatgcc   2386

tgtgttagtt aaagacagat gggatcaagg cgagggctac aggctgagag agcttgagct   2446

cagaggcttt tatgaaccgt ttcctctgag ggccaccctt gatctctagc agaacagcaa   2506

gcagaacacc gtgcatgctg gccacagcag tggagccaag tctctgctgg ttacggagct   2566

atacggtact gcaggagttc tacatacctg ctgcgcagag accagccccg tggacagagc   2626

tggcatgatg gttgctacag tgctctttct cccatgaagt ctttgctttt atatcagtgc   2686

cttatctgtt aagctcctgg aggaaagccc cctattctag atctttatgt gaatggataa   2746

atgtgacacc cgagacaccc tttagtagtt tgacagcttg cgtgtgtgcc gcctaattag   2806

agcacaggga gcagggcagc tgttattcct gttttaccaa gtcaaggctt agggaagttc   2866

agccacctgc ttagatgata tatcaaggtg gcagtggaag gggtgagct aaggacccag    2926

caaggtttcc tggaggcaaa gtttatgaaa tcctttctgt aactccataa agatgtctgc   2986

agctatttcc tacccagatg ttcctgatgt gataagcagg ggactttttt tttttccctt   3046

cagatgctat ccataaaatc caagcccttt cttaagatac aagcagaaga acggttgcgt   3106

ttttgtgggt gtgctgtcag cctgggggt gggggtggg gggtgggaga gcgattactc     3166

tgtgtttagg tttgtcacgc acattctttg catctgtatt gtaccagctt tatagcactg   3226

tttcatgcca aagttctgat gacgtaacca gttgaccctt cacacagagt gccctttccc   3286

cccctccccc ctccccatgc ttctgtgatt gctctgtagc catgtgaagc ttgctagccg   3346

cggctgtaca tcctgtgact tccaccttgg gtttagtaat gggagcttga gattggagag   3406

ctgagtcctc tgtgggttct gtatttatcc atttggcttg aagctttgtt tatatatcgg   3466

ctgctttttt ttttttaaat gctcagacca ttatttattt cttgagtgta tataagtata   3526

aagacaaatc tatggttagt ttttacttta agattaaccg atttcaagat ttacaaaaaa   3586

aaacaacaaa aaaaaaaaaa aaaa                                           3610
```

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12

```
gctgaatgcc acaaacacct t                                               21
```

<210> SEQ ID NO 13
<211> LENGTH: 24
<212> TYPE: DNA
<213> ORGANISM: Artificial Sequence
<220> FEATURE:
<223> OTHER INFORMATION: PCR Primer

<400> SEQUENCE: 13

```
caggtaagtc gcatcttcaa gaga                                            24
```

-continued

<210> SEQ ID NO 14
<211> LENGTH: 28
<212> TYPE: DNA
<213> ORGANISM: Artificial Sequence
<220> FEATURE:
<223> OTHER INFORMATION: PCR Probe

<400> SEQUENCE: 14
cttgtctaca ctgaggagga cttgggcg 28

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt 20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat 20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc 27

<210> SEQ ID NO 18
<211> LENGTH: 75033
<212> TYPE: DNA
<213> ORGANISM: Homo sapiens
<220> FEATURE:
<221> NAME/KEY: misc_feature
<222> LOCATION: 870-969, 6868-6967, 11680-11779, 14719-14818,
18148-18247, 21488-21587, 24421-24520, 45266-45365,
52072-52171, 55444-55543, 58798-58897, 60802-60901,
63660-63759, 65249-65348, 66731-66830, 67994
<223> OTHER INFORMATION: n = A,T,C or G

<400> SEQUENCE: 18
agagagtgtg gctttgagcc ttggagagga tgctctcctt ctccagggat cgcctcccca 60
gcggacgcag agtttcaggg aaatgtccgc ctccgccact tgggatggca gtggggagag 120
gaggatctgg gtgtccggag gagggcagtg ggagaaagct ggagctgctg gagtcgcagc 180
tgcctgcgga gcgggcccgg gaggaagcgg ggccgagcgt gcggcgtcca cgcggtgagt 240
gtgcagcgct ttcattcaaa ctttctccag tctcggttcc ggcgtcagca aggtgtgacc 300
aatcagagcc cagagacggg aataaattat gcaaatcacc atctggcgat gggtcagatg 360
actcccatac ttttaaaaac tacctctata ggagcgtgac agcagcgagt ccttgcctcc 420
cggcggctca ggacgagggc agatctcgtt ctggggcaag ccgttgacac tcgctccctg 480
ccaccgcccg ggctccgtgc cgccaagttt tcattttcca ccttctctgc ctccagtccc 540

-continued

```
ccagcccctg gccgagagaa gggtcttacc ggccgggatt gctggaaaca ccaagaggtg    600
gtttttgttt tttaaaactt ctgtttcttg ggagggggtg tggcggggca ggatgagcaa    660
ctccgttcct ctgctctgtt tctggagcct ctgctattgc tttgctgcgg ggagccccgt    720
acctttttggt ccagagggac ggctggaagg taacgtgaat ttgtttttat tccccccagc    780
cacttctctg tgctgggtcc cctctgtctt gctgattctt caaaccctcc ttgttcctat    840
gaaattcttc ctttcccact gcgctgcccn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnng gccgcagtgc gctgtgaatg agccactgca ctccagcctg ggcaacagag   1020
agattccatc taagaaaaaa gttcatttaa gttttatagg aaaatcactg aaggttcaaa   1080
agacaaacta ttcactcaaa aggaaatgat ctcacaaggc ttaaatgtct tctaatctaa   1140
cccaatgctg gctgacagac tcaaatgtgg tgtgactgtt tttaattata ggcttgattt   1200
ctccctaaaa tcagagaaaa tatggttgga gtccataggg gatggagaaa gaagggataa   1260
aagatgagga aggcaaaggc cagatcatgg aaggctctta tatcatcccc aaatatttgg   1320
aacaggggcc acaggaaaaa aaaaacccaa aaaatgacat gatcattctg acagccattt   1380
tagaaaaatg actctgtcag ggccaggcgt ggtggctcac gtctgtaatc ccagcacttt   1440
gggaggctga ggtgggcgga tcacatgagg tcaggagttc aagaccagcc tggccaacat   1500
gacaaaatcc tatctctatt aaaaatacaa aaattagctg ggcatcgtgg tgggtgcctg   1560
taatcccagc tgcttgggag gctgaggcag gagaatcgct tgaacctgga ggcagaggtt   1620
gcagtgagct gagatcacac cactgcactc cagcctgggg ccacagagtg agaccttgtc   1680
tcaaaaaaaa aaaaaaaaag aaagaaagaa agaaagaaaa agaaaagaaa agaaaaatga   1740
ctgtcaggaa tatggaggat atattaaagt gcagaaataa ttagggcaag aagaccactt   1800
aaaagaataa tccagatttt gttaaataat tgtatgtgca aagacaagaa gaggggagtc   1860
tctcatcttt ctggtttaag atcctaggtg tatggggaag tcgccaaaca aggaagggag   1920
aaaggcaggg tcgcctaggg atgcagagct tggtcacaga aggctgcctt ggatcccagg   1980
gctgccactc ccagctgccg gaccttggat ttgccgggga gttccttttt tttcttcttc   2040
tttttaacac attgtagcag ccagatcaac ttcatcattt acaaatagtt gtcctaagga   2100
ttacttgagg aaatgcatgt aaaaacactg aaaatactgc ctagaatcta gtaagcttat   2160
agaatcattg tctgttactc ttgtcaccat gcaacataaa agaggaaccc ggaggagaag   2220
acaaagagtt ctgtttaagg gcatgttagg tttcaaataa cctcaggtct tcagggacct   2280
cccagaaagg atgtccaggg agtagtttgc tatcagggtc tagctcagga gacagatgtg   2340
gcgctggggt attaatctgg gagttagcat gcagttgaaa gctcatgtga ggggagggaa   2400
ttaccgagga aacaccatgg aatccagcat cagcaatgga agtggagtcg aggggagaga   2460
cttagggctg aggtctccta cactgaggtc aaggaagcaa gtgagcctag cctggagtct   2520
actctcctag agtttgagct gcctagaagg gtggtgccat gaaatagaag ccctaacaaa   2580
agctaagtgc atcactgact atgagggaat aaccagagag atgacctggg gaaggaaaaa   2640
agggaagaaa atgccaaaag gttttctcct ccagatgaag atctagaagc agcggggaaa   2700
acgaggatat tgaaccagac ccttcagtta gcgcattttt cacacaggtt ataatacaat   2760
tgattggatg acattcccat cctgagaatt tcctgattac cataattacg tctcatcctt   2820
tcatcttttt aattggccat ttacaaacca ctttcaggag tacagggcca cataatcaaa   2880
```

-continued

```
cctaactaat gtgacgaata aataaaatgt ttctttcata tctaataata cgtagcctgt   2940
cctagaacta caaacctgtt tttaattgac tgacatttaa aaccctgaat ttttatttct   3000
gtatacaaaa aagagaactt tgagacagtc cctaagtagg caattcgttt tcacacgttc   3060
ttaaaacata ttccacactc ccttcgcttt ccgccttcct gcctcctcag atctcgtttc   3120
ttcggctacg aatctcgcga gaagtcaagt tctcatgagt tctcccaaaa tccaccgctc   3180
ttcctctttc cctaagcagc ctgaggtgag tgtttctcct gcgttgctcc gagggcccaa   3240
tcctcctgcc atcgccgcca tcctggcttc gggggcgccg gcctccaggc ccccgggagg   3300
agaactccta gggctactaa atcctcgctg gaggcggtgg cttcttatgc gggaggacgt   3360
ggcggagggc ctgactttgg gagccggggt cagtcggcct ctgaggtccg cagagggacg   3420
tgatgggcgg gaatggggac taccgggctc ctccactggt gggggcgccg gcccgccgtg   3480
gggtgcgggc cgcctggggt ccgtgcggac tccggaggtc cggtgtctag tggtgagtgg   3540
tggccgcaac gaggaaaaag ttttggggga aagaaaagtc gggtggaggc gtaacacgtt   3600
actacaagag tgttgcgtac aggagggctc ttaaagtggg tcatagcccg aaggtgttga   3660
gagagacggc actcactacc tgcagccctg acagcaaagg ggtttctgta gagcgggagg   3720
gaggaggtgt agagggttac ggttgagttg tgccctgcgg atgcgtcgag tcattttacg   3780
cctggaagat ccagcattgg attgaaacag gctgtatttt cttccaaagg gttgactgga   3840
ttggtgaggc ccgtgtggct acttctgtgg aagcagtgct gtagttactg gaagataaaa   3900
gggaaagcaa gcccttggtg ggggaaagta tggctgcgat gatggcattt cttaggacac   3960
ctttggatta ataatgaaaa caactactct ctgagcagct gttcgaatca tctgatattt   4020
atactgaatg agttactgta agtacgtatt gacagaatta cactgtactt tcctctaggt   4080
gatctgtgaa aatggttcgc tattcacttg acccggagaa ccccacgaaa tgtaagtgga   4140
caggaggtag atacccattt cctacttggg gcttggcata agataccaaa aattaaccaa   4200
aacgttttat ttcctagcat gcaaatcaag aggttccaat cttcgtgttc actttaaggt   4260
atgcgattca tagttgtgat ccaacagttc ctcatgttcc actcaaaaaa ggtagctgca   4320
gtgatgactt tcttaggaca cctttggatt taccgtgaaa attaataaat tctgagcagc   4380
caccttatat ttaggcattg atgatcaggg tgtaaggatg tagcgtttgt gaaattgaga   4440
agtagtacca gaaaaccatt tgaaaaccta gtgtgcagat caagatgggg cattttaatt   4500
gtaattacat gatgatggaa tttaaacgtt ttatagtgaa taaatggagt tttggagttt   4560
tctctagctt caacgaagtt tacctggctt ttagtcacaa gtttttttaa ttgccttgcc   4620
cccaaagaat agaaataact cgacattttg aaaagctgaa aattgaaaat ttaacgttta   4680
ctttaaaaat taaagctttg atctagttaa ccaacacttt attcttcata cttagaacac   4740
tcgtgaaact gctcaggcca tcaagggtat gcatatacga aaagccacga agtatctgaa   4800
agatgtcact ttacagaaac agtgtgtacc attccgacgt tacaatggtg gagttggcag   4860
gtgtgcgcag gtgagaattc ttagttgcca tttgaaaaga cagattttaa tggaaaagtg   4920
atgggatagg ataagaatgg ctaagatctg tgctgatgaa cctatttctg gttgctgtaa   4980
tgacaggaca ccttggattg atggtgaaat aaaccatatc ctaagaaacc gtgatatcag   5040
ataaattcat cttggctgta atgttaattt aaatcaagga aaatgactca tcatctccat   5100
tttctttcag gcaagcaatg gggctggaca caaggtcggt ggcccaaaaa gagtgctgaa   5160
ttattgctgc acatgcttaa aaacgcagag agtaatgctg aacttaaggt acccaaacca   5220
ctaacatcct gtgcaacttg ggtggttgtt taattaatgt tggctgttca gatttatgtc   5280
```

-continued

```
cttgatttc ttgttttcag taattaactc atttaggatt ttttaaattt ctacctgcag   5340
tttccacaga atgaaactat ttccttttat tttttttgag tccctttatg gcaaaattct   5400
gtgaagatcc agaagcgtgc tctgtggtct ctttaagcct aacacttagt atttctagtt   5460
ttctgctgtc tttttacact ggaggtactt taccaggggc ttttacccct ttttgtgaca   5520
tacacctttg gtagtatgat taattatcaa aatgattgcc ttagcagtga ttaatgtggt   5580
ttgtggccta ccttcataat ggagagtcat gttgcatttc agaaagaaat tgtttaaaat   5640
ttcaaaaagt ttaaacaatg acaaacttgt gttgacaaaa cacaaatttc tccattttgt   5700
atattaccca ttagcctttt gcatttgaag gtctgggcca gaactggaat tagtttaggt   5760
ctgtatggct ccaaaccttc taagccatgc tgagaaattt tatcatcaag acttcaaatt   5820
gggttcttcc ttacccctca gctctccacc cgtctaagga tctttgggaa ggccactcat   5880
agacaaaatg tatagcacac tgagtttggt ggcaatttag acatgtaaag gtgaaggcag   5940
acaactggtt aaaaaaatgc tatttgcaga ataaaaggat tgcctttcaa aaatgatttc   6000
attgaggcag gactctggag caagcctggg aattcatatt tagcaatgat agtttgtggt   6060
gttttactaa ttaaggatgt tcctggtttc attctccttc ctttcttccc cagggtttag   6120
atgtagattc tctggtcatt gagcatatcc aagtgaacaa agcacctaag atgcgccgcc   6180
ggacctacag agctcatggt cggattaacc catacatgag ctctccctgc cacattgaga   6240
tgatccttac ggaaaaggaa cagattgttc ctaaaccaga agaggaggtt gcccagaaga   6300
aaaaggtaaa taagtagttg ctcggttttg tttgtgatag tagaaagatt tgtggttgct   6360
gtgatgacta tcttaggaca cctttggaat aactatgaaa gaaaactatt ctgagcaacc   6420
cttttcacct gtcttatttt ggcttttgta agtttgtttc ttgactaata ataaatggta   6480
agttttctgt aatcccagca ctttgggagg ctgaggtggg tggatcacaa ggtcaggaga   6540
tcgagaccat cctggctaac acagtgaaac cccgtctcta ctaaaaatgc aaaaaaaaat   6600
tagctgggcg tggtggcggg tatctgtagt cccagctact caggaggctg aggcaggaga   6660
atggcatgaa cccgggagga ggaactagga gtgagccgag atcgcgccac tgcactccag   6720
cctgggtgac agagcgagac gctgtctcaa aaaaaaaaaa aactggtagt tttatattca   6780
gtacctcagg cccgtatgat tatctgctga tggccccact tagatgtact tagccacttc   6840
aaaatgggcc ctctccccaa atctaagnnn nnnnnnnnnn nnnnnnnnnn nnnnnnnnnn   6900
nnnnnnnnnn nnnnnnnnnn nnnnnnnnnn nnnnnnnnnn nnnnnnnnnn nnnnnnnnnn   6960
nnnnnnnata atatatagtc actttactcc taaatatata ttatatagca tatataatat   7020
gctatattat atatcatata taatatgcta tattatatat catatactat attatatatc   7080
atatataata gtatatgtat atttaggagg aaagcgattc tggaatagag tgtagaattt   7140
gtggattatc agcctgagaa gggacaaagg gcattagggc atcatttaca cattatgagg   7200
gtgttagaac agaatatggt tatcatggat tttcagatcc actaatgttt actttccatt   7260
taaggcacat caaatcaaga gatagtcagt acacataaaa gaggagattg actttatgta   7320
tttatcaaat atttcacaaa tataaaatat tgagcatatc atgttttatt tatttattta   7380
tttatttatt tatttattta tttattggtg acagagtctc cctctgttgc ccaggctgaa   7440
gtacagtgac atgattgtat aatagctcac tgcaacttca aaatcctgga tttcaggtga   7500
tcctcctgcc tcagccttct gagtagctgg gactacaggc ttattagcta gtagtagcct   7560
ggctaatttg taaatttttg tagagacaga gttttgcttt gttgtcaagg ctggtcttga   7620
```

-continued

```
actcagcttc tggaaatcct tgtaccttag cctcccaaag tgctggaatt acaggcatga   7680
gccacagttc ctggcctgtt accaagtatt ttttaatgtt tactagtttg atgggtaaaa   7740
atgatatatt attgttttaa ttagcatatt gtactcagaa tttagtctga agatcttttc   7800
atatatttat tagctgtgag accttggcta tttcagcaag tattttttga gtaatttctc   7860
tttagcagta tgctggagat tgattaggga taaggaagaa gtgtaaggcc tgattcatgc   7920
ctctcaggaa taatctacct ggggagatat gttatatgta ctacagcaaa ataacatttc   7980
aaggcagctt ttacgtaatt gcagctttag gggagtagtg gagagtttta aggggtaaca   8040
gggaggaatg atagaatcag ttttgcacat gttaagattg agttcttgac tacattgcat   8100
tgaagatagg tcctttgaaa ggtttactac taaaagcatc agcaatagcc tacttctcat   8160
ttctagcata gagttacata aggatcattg ttaccaacaa acttactgat tatattatat   8220
atattaccct tgagttaaaa aaagtctgaa atattttaga gatatcaaca gaactggctt   8280
cctggccaga ggttgggtct agaaggagaa atttgaaagt agtatcatgg aagccactag   8340
aaaagccagg agatgggatc agttactgac agatttagag aaagaagagc tggaagccaa   8400
gggagtctaa tgatgcccag tgagggcaaa ggcagtagga ctctttggag attatccaat   8460
agtgttttct actttactct agttttcatt gataagggtc ttgagagttc caaataaatt   8520
gggagccgac gattgtgcgt gtgtgtttgg aatccttggc aggaatcatt gcagaagaga   8580
tgccattggg gctcagtttt ctactttgct ttttgtgggg gagcaggtgg atctttctgg   8640
caagagtgcc tcagtggcta ctggtcttac tatgtctgaa cttattcctc ctgtatactc   8700
caggtgccca gggtgttgcc ttcactctgt tcctagcagg tagcaccctg ttgttgcttc   8760
ctgtgggagt gagggcttag gcaggggtgt ctgctcaggt gcactagcca agcttctgtt   8820
agttgcttgt gggccttttt ctggcctttc tgcttttgtg ccggagttcc tgttcacact   8880
ctttgggatg gtgcccttga aggcccttga gcctgctctg ggatgctatt tcccttttta   8940
gcccatctcc agctgttttc tactttatgg ggattcttca cagcttctgg ccgcctgtta   9000
tttttttagc atggctgtgt aatcactggc tatttaaaaa aatatgattt atattatttc   9060
tagggtttgg tgagaaaaaa cggggaagga ggcactgtac tctttactca attggctgtc   9120
tcgatttttt ttgttaacat tctgttcagt gtctctcctg atatgcttgt aggctttatt   9180
catactgttt tagaaagatt tcatagtgtt cttggactga gcagttattt tgatttatta   9240
attttatttt tgatacaaag tcttgctctg ttgcacagtg cagtggtgta gacgtggctc   9300
actgcagcgt cgaactcctg ggctcaagcg atccttctga gtagctggga ccacaggctt   9360
gtgccaccac gcccagctag tttttaaatt ttttgtatag atggggtctt gcccaggctg   9420
gcctcgtact cctgggctca agcaatcctc ctgctctgtc tcccaaagtg ctgggattac   9480
aggtgtacag gtgtttgatt taagacttaa ttttgtggtc tatcctagcc tctttgaaaa   9540
taaagtttat ttcctataaa ccaatagaaa acagtcatag gatatgagca ggtaatggtc   9600
ttattcacgg caagagagat gcaaaataaa attgtattga aaaactgctt tttaaaaaaa   9660
atctaagttg gcaaggatca gaaagtttga ttaaacaatg gtggctgtgg agtagagaaa   9720
taggcgttgc tggtgagaat ccaagttggt acaacctctg tagaaggcag ccaggcagta   9780
tctatcaaaa ttacagatgc atataccctt tgacccagca attctatttc tctggattta   9840
tcatatctgt ctactcatac atgtgtgaaa tattttatat gcttatgtaa gtgatagtat   9900
aagatataag taatgtatat atcttattgg agaatgacat ttattttta ttacttggag   9960
aatgatttgt aatagcaaaa gatgtagact acctaaagtc catcaatatg gtatttgaga  10020
```

-continued

```
aattataaaa tggaatgtta cacaattgta aaaaggaatg aagtgcttca tatatggata  10080
tataatgact tcctatatat tgatgagtgg gaatagcaga gtagagagga atatgtcata  10140
tgctatggtt tgtttaaaaa ggggttgaac atatgtttgt atatacacag aatgtctgtg  10200
gaatgatgcc caagaaactg tgaatgtttt ctctgagttg agaaggtggt tagaagatgg  10260
gatgggaagg agattttcac tgtctatcct ttgaagcttt tgtattttgt accatgaata  10320
ttactgatac aaaaagaaca taaaataaac agaaacatct gacaaatttt gttagtagac  10380
tctttgatag tattgtttct cgttgttgct tcacctggtg ggaggaggag gttgattcca  10440
aaatcaaatt ttgttctttt gaaaattcag cattcatgta cttaaactcc tagagtaaaa  10500
ttgcttgctt ttaagttacc acacaaaaaa agtaagatac tggtctattt aactgagaac  10560
aaattgttat gattttcatt tcttttgatc tggtgtcatt tttttcctgt taattttaat  10620
gaagcacaga gaaggaaaat tgagtacatg gtagagccag gaggacccat atttaaattg  10680
ctgtcagcaa accaacactc tttgaactaa cccactttca tccatacagt tagaggtact  10740
tattcagtac actaatatta gacctacaat cctaactgct aattagcatg agtcccctga  10800
taaatagcac actgtaaaca agtagtcaag gtctttttta ctcgtttgtt taaacatatg  10860
gtttattgag gcatattcag ggtcacaggg attattggac aaataaaaat aatttgaaag  10920
ctttggctaa aaaggaacta gcaatatcct taaggaggtg gtggaagaca aaatctgttg  10980
tatactcctc agagttaatg aaattaatgc agaatcccag aggacccaag aacattactt  11040
attttgcttt tattgaaaaa gttcaatttt gaataaaatc tgaaagaaat aatttattgg  11100
gtagctggga gaggtggctc atacctctaa ttccagtgct ttgggaagcc taggcaagag  11160
ggtctcttga ggccaggaga ttgagattag cctcagcaac atagcaagac gcccatctct  11220
ataaaaaatt taaaaaagtt agcagggtgt gatggcatgt atctgtaatc ccacctactc  11280
agaaggctaa ggcggaagga ttgcttgaat tcaggagttt gaagctacag tgaattatgt  11340
tcatgccact gcactctagt gtgggtgaca gagtgagacc ctatctctaa aataagtaaa  11400
taaatttatt ttggaaaact agtctaagtg aaagaacatt ctgtaatagg acaccgagta  11460
actagaatat gagatcctaa tatctcatca tgtttaatat ggacgatgaa gtaacaatat  11520
gtaaaaacaa tcctagtggt tgtgaaagaa agtacctatt agtctgattt gttggcacct  11580
ctctgggaca tgtagattct tttttgtttg tttgtttttg tttttttga gatggagtgt  11640
tgttcttgtt gcccaggctg gagtgcaatg cacgatctcn nnnnnnnnnn nnnnnnnnnn  11700
nnnnnnnnnn nnnnnnnnnn nnnnnnnnnn nnnnnnnnnn nnnnnnnnnn nnnnnnnnnn  11760
nnnnnnnnnn nnnnnnnnnt ggattccaca tgtttaggtg tgtccttcaa ccccatcacc  11820
ttttcaccac tgcctgggct tgatgtgttc tctgtagaag attttttaaa atacagatag  11880
tataaaaatc cttcctgacc cctcatttgg atatttttta atggtgcctt ttttttaatt  11940
gttgacgttc aagatagact ttaaacaatc tgaaggaaaa taaatcaata tcaatgacag  12000
tcatgcacac tcaagcaatc tgtttcaaag cctaatcatt tgtcatctat tctcagtgtt  12060
tctattataa tttttattat aataatagta caggctgaat ccccagcacc tatagcagtg  12120
cctggttcag agtcgatact taaatattta tggaatgaac actaaatgtt ctctcaaaaa  12180
atgataattc agaaatatct gtatattgca aaaagtaaaa ggtcttcctt accctcccct  12240
gctccattct gatgattatg tgaaaggaaa agcctctatc cttggtgaat ctctcattta  12300
gcttttcttt tttaagaagt tgtgtattct ggtggtcttt aacagaagag ggctatgtgt  12360
```

-continued

```
tattgggggt tcattgccac ctgtaggagg caaaataacc tgtgatgagt tggccccatt  12420
gaagtaccac acctctagga agccttccct tcctcccctt ctcttgccct tgtttctgca  12480
agctctgtac aacacttctt atccgggtga ccttgcccta caggtagctg gctacctgct  12540
gtgtctttca caggatggtg agctccttgt agacagtgct gtctttatct tgccacctcc  12600
cacagtgcct tggagggtac agttgctaaa cgttttggaa ctaaacagaa aaaaacacag  12660
tacaataaga aattaccata atgctaaatc aacaaattac tcgaatctct tcccctgaca  12720
ctttagtagc tcttgaaagg gcaatttcag tgatcttgtc aaacagctaa gtcacatggt  12780
gacctagaag agggcttgga agtttgagtc attgccgttc aatactcttt cctctagaca  12840
tcctgacccc catcctctgc aaaaccatgg gcagtgcaga gtaggtcaca agtattgtgt  12900
ttttatttgt ttgtttgttt ttagagacgg gatcttgctg tgttgcccag gctggtcttg  12960
aactcctggg ctcaagtgat ccccccaccc tggcctccca aagtcctggg attataggtg  13020
tgagccaaca tgcctggcct gagttgtaaa tcttccaggc tcgtgccact ggcttctggg  13080
agactataag atatgaccta gtgtaaatgg aaataatttt tacctatttg ggttcaaaga  13140
caccaataaa tctgttcttg gccaccgagg tcagttctat ttcttcaaat cttgcctaga  13200
gtagtgtttg cacctcatgt tatgggttga attgtgtccc tccaaaattc atttgttcaa  13260
gtcctaaccc ccagtacctc agaatttgat ctttcaaaag acaaaattag gattgggtgt  13320
ggtagctcat gcctgtaatc ccagctactc aggaggctga ggcatgagaa ctgattgaac  13380
ctgggaggtg gaggttgcag taagcccaga tcgcaccact gcactccagc ttgggcaaca  13440
gagcgagaaa aaaaaaacaa aacaaaatta caacaaattt aaatatctta actgctttta  13500
tttacaattc tagaatcaag caacacctca tcctataaaa taaaacgggt gttcccaaga  13560
gctgagcaga ggagtttggt ccaatggaga gaaaaaggct aaggaaagcg gaaacagaaa  13620
acaaaaagtg gattggttgt ttcagagtta ctttcttgtt aaggctgaag cagaggggat  13680
ttccttatca tgccggctaa aactggcttc tttggggatt tggctattat ccctcactct  13740
cttcatttct cagatggtca gataaacaaa ttagtttcaa tttggtgaca tggaacctta  13800
gcatgaatga ctccattttg gttgggccta gtgcaggagc tcagtccaag ccaatggccg  13860
cctataaatt ttatttaaca ggctttattt ggaaataggt acattgtaga tagaattagg  13920
ttataatgaa gtcaccaggg tgggccctaa cccaatatga ctggcgtcct tatataaaga  13980
ggaaatttct atgtaaacac acacacagag gaacatgtga agatgaaggt ggatataagg  14040
gtgttccttc tacaagccaa ggaatgccaa gaattgtcag tagaccagca gaaagtaggg  14100
gagagcatga aacagtttct tcctcgcagc cctcagaagg aaccaactct gacaatgcct  14160
tgattttgga cttttggcct ccaggcctat gagacaataa atgtccactg tttgtggtac  14220
tttggtatgg caccctagta aaccaatata cccaggtatt acagtcagat attacagtcc  14280
atgttagctg gaaacacaag ctaactctga ggaagccaag tgtgagtctt ccaacactgg  14340
cagtgttggc aaaaggagct ctgggacagc cttttccagt gagtgacagt gtgggctgtg  14400
cagctagact gctggtgtgt gagcctccac tggctagctt tgcaatgttg ggaattgtat  14460
ttaacttgtt gcggctgtac aatgggggac aataaataag taccttgtct tagtcctttt  14520
gagctgctat aacaaaatac cacagactgg gtaatttaca aagagcaaaa attggacagg  14580
cacagtggct catgcctgta atcccagcat tttggggtgc cgaggcaggc ggttcacgag  14640
gacaggagtt ccagaccagc ctggccaaaa aactccgcct taaaaaaaaa aaaaaaaaaa  14700
aagcaaaatt tttttcccnn nnnnnnnnnn nnnnnnnnnn nnnnnnnnnn nnnnnnnnnn  14760
```

-continued

```
nnnnnnnnnn nnnnnnnnnn nnnnnnnnnn nnnnnnnnnn nnnnnnnnnn nnnnnnnnga  14820
attgtttata tgaatcattg attatgaaat agtaaagctc attctctctt atttattttg  14880
atatttttc tacttaaagt aatacttgta tattgttaga aaaggtaaat aataataaag  14940
gcaggttata aaaaatcagc agtatcctta cccatcccca ctttttaatc tcattttcag  15000
aggcagttac ttttaagaac tctgtctctc tctctctctt tttcttttgg tagagatggg  15060
gtctcactgt gttgcccagg ccgttcttga actcctagcc tcaaatggtc ctcctgcctg  15120
ggcctcccaa agtgctggga ttacaggcct gagccactgc acctggccct aaaaattctt  15180
ttaagctttt tcttttgatt cttacctctg cgtttataaa tctgcctaaa ttgctatttc  15240
gtgatttatc aattttagat aatacatatt aacttcttgt tatggtaggt ggggtattct  15300
tccctttcct tcccctattt ctaaaagcac ttccagtata ggtatataag aattcttggt  15360
taatatagtg tttagctttt atattattat gactacataa atattgttca ctgctggtga  15420
gtacttcacc atgtttcccc ttccctcccc ctagtttgct tagttttcca tggatatatt  15480
attaattttt accaaatact ttgaacggcc tgtgggattt agtgcctaag aaattgatgc  15540
aaggtgttac tctggctact gctattgcag ttgttttgtg tccctgttcc agaggtttca  15600
tgccttttc agctttgtca gtaaagtaaa atctcagatc cccaccatgc ctgacttgac  15660
agtgtaacat cccccatttt gtttgtgctt tctttttgga actgttacta ttaatatatt  15720
aaaatcttct aaattgttct ttaaattttc tattttttct cctcctgttt ttcacttatt  15780
tgtcctcttg ttctttatta tgggagttcc cttaactttt atcttttctc cgttcttttg  15840
ttttaaattt caggtgtcct ttcttgttct ttatttcctt ttttatgaca tcctactctt  15900
gcttcatgaa gcaatatgaa acggttaaaa gagaatggtt tctgtaccta tcctacctgg  15960
gtttaaaacc tgatgtgcca ctttctagct ctataatctt gggcaagtta cttaaccttt  16020
ctttgcttta gtttattcat gtaggttagg agttggtaga catttcatct aaaggaccaa  16080
atcataaata tttcaggctt tatcagccaa gaggcaaaat gaaggatatt ttaaattatt  16140
taattatttc attatgtaag tacttacata acaagagaga aaacatttct acaagttttt  16200
tattaataaa gctcaaaatg cgatactaat aatgattgag aacaattttt gcaataaagg  16260
tttgctaatg agaagaatga atgttttttt ggaggagagg ggataacatt tggcttaatt  16320
ggagtttaaa gttagtgttc tctatcatca aaattgatta tagatgcagc attaaccacc  16380
tattaatgct gatttgtaat gagatttcat gtatttcatc tttgaaaatg tcttcttaga  16440
tactgccaaa tactgctaat agtctgtgaa catatggttt taatagagca tattcattgc  16500
ttggacgaca tttacagaat tcttttagac tcttttcttg atacttaacg tttagcaaat  16560
cattacactg cagactaatc acttccaatt gaggattagg tagaagctcc tcattgcaca  16620
gttaaatgat ttttgaaatg tggaatgttc gtttctactt gcattgaggt atgaaaaaat  16680
actgctggaa atatttgatt ttggaaaata tgtctgctgc atatttgtgt ggcagtagag  16740
atcttcttat tttaattttt gacagcatag gaagtacatg aagcatcttg acatgacttg  16800
tgacttaggc aatgttagtt gtccttgaaa tgactgtctc aatataggtt ttgcacgtag  16860
accctgttgt ccttctaact ttaggctgaa ttcattaaca gatatatcaa gtctgcagca  16920
acaatagtag ttgagggtca ttcttttcat tcagaaaaat ttgtctcagc ctggagcttg  16980
aaacatttca gtaaaactct gccattgtta agccattgta ttgtttcgtg gcaggacgcg  17040
tcaggatatt tagcttctat ttctgacaaa aatgtcatga gaacaaatga aatttacctg  17100
```

-continued

```
tgacattacg gttcaataac acatgataga ttcagatgtt ttctgcagag tacctgctga  17160
ttgagaatat gattaatagc cataagcttt aaacacctta catttcacaa ggcttgtaaa  17220
ttttgtccag ctaagccttt ttctgcttca tacatatttt taccaccatc agttgttaca  17280
catcttagca gattctactt cagattgtgc tgaattagta tttccttgat tttttggaaa  17340
atattcatag ctgtaattgt ttcatacata ctgtacttcg agccactgtt ttcatggaaa  17400
gagtaggatg ttaaagatat ttattttctc tggacacaat tctttggctg ctgtaatcaa  17460
acacaattta attaactcac cattggcaaa tactttcctt gcttgcttaa caaatgagcc  17520
atttggaaat ttacttcggt tgcagcccta tttccatttt taatttttgg caagacattc  17580
tgctctgagg aggtatatct tgttttacat ttgcccattt tcctgctcat tgctctcatg  17640
agttgggagt gaatgctgtg tggcagggca tatcgggata ttgtgatgag tgcttagtct  17700
agtaatactt cctatattgt attttgctgg cacagcttcg tgatgctttt acataataaa  17760
gtactttgac atctaactag atttaaacaa tctacagtcc actgtgactt acaagtgtga  17820
catcagagta cttctgtttt tttgacgtga tagtcactgg taaaatagtt atagtatggc  17880
aatactcatg acacttgaaa tgctgttgag taaaccgtgt cattgagatt tgtggtgcac  17940
tgagagtata aagggatgag ggcaccaaat atgatctctg tagcaactac ccaagtctgc  18000
tgttgtatca ggaaaacagc tatagaccat gtgtaaacaa atgagcatgg ctgtattcta  18060
ataagacttt attgacactg aaattttctt ttcatataat ttacacatgt cacaaaatat  18120
tcttttgatt tttttcaacg atttaaannn nnnnnnnnnn nnnnnnnnnn nnnnnnnnnn  18180
nnnnnnnnnn nnnnnnnnnn nnnnnnnnnn nnnnnnnnnn nnnnnnnnnn nnnnnnnnnn  18240
nnnnnnntga gcttgaagac ccctgagccc agatgagaac cgcggacctg cctgcatcct  18300
gattttagcc atggtgaaac cctgagcaga gaatccaact agaccatacc aggacatctg  18360
acccccttaaa ctgggaggta atagatttgg gttgctttaa gcccctacat ttgtggcaat  18420
ttgttatgca tggagaacct ttatgtctag ctaagggatt gcagatacac caatcagcac  18480
tctgtgtcta gctcaaggtt tgtgaacaga ccaatcagca ccctgtgtct aggctcaggg  18540
tttgaggatg caccaatcgg cactctgtat ctagctaatc tggtggggac ttggagaatc  18600
tttatgtcta gctaagggat tgtaaataca ccaatcagca ctctgtgtct agctcaaggt  18660
ttgtaaatgt accaatccac accctgtgtc tagctcaagg tttgtaaatg caccaatcag  18720
cactctgtat ctagctcagg gtttgtaaat ataccaatca gtactctgta tctagctaat  18780
ctaggggggga cttggagaac ttttgtgtcg agctcaggga ttgtacacgc accaatcagc  18840
accctgtaaa atggaccaat cagcaggatg tgggtggggc cagataaggg aataaaagca  18900
ggctgcccca accagcagtg gcaaccggct caggtcccct tccacactgc gggagctttg  18960
ttctttcgct ctttgcaata aatcttgttg ctgctcactc tttgggtcca cactgccttt  19020
atgagctgta acactcactg cgaaggtctg cagcttcact cctgaagcca gcgagagcac  19080
gaacccacca gaaggaagaa actccgaaca catccgaaat cagaaggaca aactccacac  19140
acgccgcctt taagaactgt aacactcacc gtgagggtcc gtggcttcat tcttgaagtc  19200
aatgagacca agaacccacc aattctggac acaatagcac cttctaactg aaatactgga  19260
aagagagttt tcattgttgt agaatttgct taattattat cctgatagca gggataatta  19320
ccaacaaaaa ggaagcacga aagttttact aacaccgagt ttgctagaac ttcttattgg  19380
gtttggtaat atgtcacacc ctggctatgc aaagaaggtt ataaaggaaa gagattttct  19440
gtggaagtca tgaagggatt gataactgca ggaaagatct agccaaggtt aacactaaag  19500
```

-continued

```
ttactccagc cacccaaatc caatgccact tatcctaaaa ggaatgttac ttttatatta  19560
acatttcaac aacatctggt ggaggcaaac cagtgttaca acccatcaga atagcaacag  19620
aatcaaactc caaatgatgc tgcagacaga accacacacg gacatgcctt tcttccaagg  19680
acccttagat tgaccccagg aggagcccta gctgctgatc cccacatgat gcccctttc  19740
agcaggaagt agccagaaag agtcatcacc caacaccccc taacagcagt tagggttgcc  19800
actccagagc agggaatgat gatataggag ttaacaagga attacttagg cagatagcaa  19860
gggcatggga gtcctcagta aggctgttct ttttaatgaa aagcagcccc aaatcatttt  19920
ctaacaaaga gcagcctgca agctgggagc ttgcacacga taatgcctgc agaaactaag  19980
gactagacat tttcaaaatg gcggctccat cttcccttct ctgccagcca catgtactgt  20040
aaaggagcag acaggatggt gccaatcaac tggaaagccc atttgcataa gattaggttg  20100
aggcaaccag ccttccccac acactctgta gacgtcatgc atgatcgaac caatctgtga  20160
gccctatgta aatcagacac tgccttctcc atataaaaat ctgctgcagg ccgggtgcag  20220
tggctctcgc ctgtaatctc agcactttgg gaggccgagg cgggcagatc acgaggtcag  20280
gagatcaaga ccatcctggc caacatggtg aaaccccgtc tctactaaaa tacaaaaaaa  20340
aattagccag gtgtggtggc acacgcctgt agtcccagct actagggaga ctgaggcagg  20400
gggatcacct gaacctggga ggtggaggtt gtcagtgagc tgagattttg ccactacaat  20460
ccaacctggg caacagggcc agactccatt tctaaaaaaa aaaaaaatac aaaaattagc  20520
tgggcatggt ggcaggtacc tgtaatccca gctacttggg aggctgagac aggagaatca  20580
cttgaacctg ggaggcggag gttgcagtga gccaagactg caccattgca ttccagcctg  20640
ggcaataaga gctaaactcc atctcaaaaa aacaaaacaa aaaagaaaaa gaaagtggcc  20700
acccctgtgg aaaaggactc tggagtgggg agggtggtag agcagttttt tatattaagt  20760
ttgtcatatt agttgacttt tcaaaatcac atccatatac tactttgatt aaaaataaaa  20820
tattttctgg ccaggcacag tggatcacgc ctgtaatcac agcaactcgg gaggctgagg  20880
caggaggatc acttgaggac aggggttaga taccagcctg ggcaatatag caataccctg  20940
tctctaaaaa aaatttttta attagccagg tgtggtggtg catggagatt tcaacaacaa  21000
caacaaaaaa agcacaaccc ataaaagaaa aaaatttata aactgagctt catcaaatta  21060
aaaactttg ggccaggtgt ggtagctcat gcctataatc ccagcacttt aggaagccaa  21120
ggcaggcgga tcacttgagg tcaggagttc aagaccaggc tggccaacgt ggtaaaacct  21180
catctctact aaaaatacaa aaattagcac agcatggtgg tgtgcgccta taatcccagc  21240
ttctagggag actaaggcac gagaatcact tgaacccagg aggcagaggt ttcagtgagc  21300
caagatcatg ccactgcact tcagtctggg gaacagacca tgactccatc tcaaaaaaaa  21360
aaaaaaaaaa aagaagtgaa atgaaggaca gcaatgtata tgtgaactga aaatgcaaca  21420
gacaggcaga aagaattagg aatgcttgtt attataaggt attgtgcaaa ctgtgaagtg  21480
gtgatgtnnn nnnnnnnnnn nnnnnnnnnn nnnnnnnnnn nnnnnnnnnn nnnnnnnnnn  21540
nnnnnnnnnn nnnnnnnnnn nnnnnnnnnn nnnnnnnnnn nnnnnnntgt gtgtgtgtgg  21600
gtattttttt tttttttct ttttttgaga caaagtgtct ctgtgtcatc caggctggag  21660
agcagtggca tgaacacggc tcactgcagc ctcaacctcc tgggctctag tgatcctctt  21720
gtcccagcca cttatgtagc tgggaccaca ggagtatgcc accatgccca gctaattttt  21780
tgatcttgta gagacaaggt ctcactttgt tgtgcaagtt ggtttcaaac tcctgggctc  21840
```

-continued

```
aagctatcct cttgcctccc aaagtgctgg gattacaggc gtgagccacc acatctatcc  21900
cctttcagat atcttaatct tggtaaattc tttcagttac taatctgtga tgaactaatt  21960
tttttcttca catatatcaa cagttgagga gctcaagctt gggaaaatgg tgtgcattcc  22020
ttgtatcgtc attccagttc tgctctggat ctacaaaaaa ttcctggagc catatatata  22080
ccctctggtt tccccccttcg ttagtcgtat atggcctaag aaagcaatac aagaatccaa  22140
tgatacaaac aaaggcaaag taaactttaa ggtaagaaca ttcacatgcc ttgaataaga  22200
gcagtgaaag ggggtggtac ttgggtgaaa cactagattt tggaaggaca agttttagaa  22260
ccagaagctt caatagtttg tgtaacattt ggcttaaatt aaagttttaa agtaggcctc  22320
tgattaatgc atttgtcctt tggccaaaat gataaccata ttttctgact ggtaagtgca  22380
atggtaaata gctaatggat gaggagagat tatgctgata caaaccagtt tcactgattg  22440
atgactttga taagagattt aattagaagg atcatagaga tttaaaaaaa aaacaatttt  22500
tttaaaaatg agtggacaac tctgttgtct ttagaattgg tgcttttta gattcagctt  22560
tgtactcagc tgcactaatt tagccatccg gcccgtttct ggaagcaaaa tgttttcact  22620
ctggagcttg tctgttttta aagagaatgt ttcttgagct gggcgcggta gctcacgcct  22680
gtaatcccag cacttgggga ggtcaagatg ggttgatcac ctgaggtcag gagtttgaga  22740
ccagcctgac caacatggtg aaacctggta attcccatat tagcccggca ctggtggggc  22800
aagcccgtag tccccactac taggggagct gagatgagag gattgcttga acccgggggg  22860
caaaaggttg cagtgagctg aggagaaact tccctgcaat cccccctggg ggacacgagc  22920
cagaccccgt ttggaaaaaa aaaaaaaagt aggaatcatt cttcaggcag cacatagggt  22980
ttagcccttg ggctgtaatt tgccaattta tgatttaggc aatgagaaaa aaaagtacca  23040
cgccatagtt tgtggtgagt gtaaaatcag ttagtatatg tgaaacagtt aagatggtga  23100
ctggggacat agtaggtgct aaatacatgt ttggtattat tgttactgtt ttcattatta  23160
tctatctaaa gatattttag tttttaattt tttcttagaa tcatctgttt tctatgattc  23220
ctttctttag tttgtttcag tttctttttt ttatttttga gacaggatct ccctctgttg  23280
cccaggctgg agtgtggtgg cacgatcaca gctcattgca gccttgacct ctcaggctca  23340
ggcaatcctc tcacctcagc ctcccaagta gcaggaacta taggcgtgca ccaccatgtc  23400
tggctaattt gtttattttt ttgtagaggc attaaaaatg tctctgtgtt gcccaggttg  23460
atctccaagt cctgggctca agtgattctt ttgtcttggc ttcccaaagc gctgggattc  23520
taggagtcag tcaccatgcc cgggctgctt tggtttctat atttcatgct ggagacttta  23580
ctcacaagtc taatcatttt tgactgtcca ttcttattta aagttgagac tacccaaaaa  23640
ctgattggaa gctctttgtg taagtagatt ttgttgagtg gtgggcattg ctgtgaggtg  23700
acgatctatt ttttaaattg gcctggcagt tcctaaattt ctgtatcttt tccctaggtt  23760
cctattcagt ttctcttgag aggaatcctt cagtctcctg ccttggaggc agggaaactc  23820
actgtggagc tgtagcaagt tgactttatc ttcattctct tgttttcttc attttccacc  23880
ttattaccct ccccaacctt ggcattggtc tctctagttg tatttctctg ggaagcacgc  23940
ataatagtct cttcctgggg agagagaccc ccaggcttta gtcctgcacc ttgccccgtc  24000
ttccccagtg ccctgtctct cgctctttag ccttcccacg gctccatggg gtgaattgcc  24060
ttccttcttg ttggtgtccc ccttggcagg aactcctttt ggggcttcct caggtcggct  24120
ggttcaggta cactcctctg tcaccttccc atcttccaca cttcccttga tctgatcttt  24180
gtgggtttat atctttcttt ccattgcttt cgtttcattg ggcggggaat acccaactgt  24240
```

-continued

```
acttaatata gcacttggag cctagttgcc tttcagagaa tgttctatta cttgtggact  24300
catggcacct gtggcattta ctctgtcctt tggctggtga ttattgccca ttatttctct  24360
gatctcctgt ttcagctttc tccttaaagt ctctgaggta caagtggggc aatatgtgtg  24420
nnnnnnnnnn nnnnnnnnnn nnnnnnnnnn nnnnnnnnnn nnnnnnnnnn nnnnnnnnnn  24480
nnnnnnnnnn nnnnnnnnnn nnnnnnnnnn nnnnnnnnnn ggcatcccgg caagtcatgc  24540
aaaaggcaaa ggctggcagg ttgcgctggc tcttgccagc cctcccaccc ccacctcctt  24600
cccttatacg gctccctaag ccagtgctgg tgctgtccag ccagccgagc ggcctggcag  24660
cagctctgaa accttgtcct catgcctgaa cctggaggtt tgagaggcaa gaaggctgtc  24720
agagctgtgt ctcctggagc tgccttttaa tcttggtgta ggtgtcttga aagttcaggt  24780
ggcagggtag ctggctttgg tttgattcgt gcttgcaggg agcgtctggt gggtcgcttg  24840
tgcttagaag ctgccgggcc tattccccca ggttgccagc cttttcctct tcaacactct  24900
tgtgctcccc cgactcttcc tcttcccact cctcctccct ttcctcctcc tggcttttag  24960
cttctcttcc tcttgggttc tgtatggcag cctttgccag tggaggcagc ttgccctggg  25020
ggagccagag tcagtcagct ctgggggagt cagaatcaga gtgagaacta agtcagctga  25080
taagcagtgg agggctgggg agcctctaaa ctgaacccca tcatctcatc ttctagtctg  25140
ctgaggttgt gccaaatggt ctgtgtgggc ttgtgtatgt gtgggagggt tactgtgaat  25200
gaatggaaag ccttgcttta ctcaacatgt ttccaactct ggtgctaact agaagcattg  25260
cctagggcag gtctcatctc tggctcctca cctgtaaaat gctaaagttc cttctaactt  25320
ctgtgttctg ggcctctgag tatgtgtgag tcatttcctt cattgcaaaa agtatttact  25380
gcatacctac ttagtgtcag acactattct gggagcaggg gagagagcag tggacaaaat  25440
agatggcaat ctgtgccctt gtgacactta catttcagtg gtgggaagac agacagtgca  25500
ctgattaaag tatcagtggt gctcagtatt atggagaaaa atcaagcaga ggaggaaggt  25560
ggggcatgtt ggtgggggaa ggtggtgcga ttttatgatg tggtcaggga aggcctttct  25620
ggagaagttg accattgagc aaagagctga agggggtgag agaaggagcc atgaggacat  25680
ctgggtgagg aacaatcaga aagtcccaga ggctgaagtg acccaggcca aaagtagtag  25740
gaatgtacct agagaacttt ggggtcagag caggtcagac tctaagagga agagtctttg  25800
tccatatgtg ggtttatccg cagatctgtc tcaggaatcc aggagacttc ttttctccta  25860
ggtttcccca tctggcctct gcatgagtgg ctatctgggt agaaggtggg gagttgtcga  25920
actcattatg tccgtggttc aaatttctgc tggttggggc ttttgttcat tactttcatg  25980
acggttaacc tgacttccgc tcatgtgcat tcagcagcat tttctggaac cttatccctc  26040
ttacatctgc tgcattcttc cccctctctc cctcctttcc cctccgccct ctccaccact  26100
atatctcttt ccttttggta tcttcttcct tttgcttctt aactctgaga taaattaact  26160
ccaagatggt catttggcat ctttccctgc tgggtgatag gagagtttga tactctcact  26220
ttctagccag ttatccagtg atgcatccca ggatggctga aagagtgctg ggtggggtcc  26280
atttatgact ttctgaaacg gtgtcatgat gacagcacct acttagtgtt aagccacagt  26340
ggccatcagt gacatgagct gcactttggg agcagggccg tctcctaggt ggcactgtgc  26400
atgagcagtg aagctggaag gggggatttt tgttgctttt aggagtttct ccatggcttt  26460
agtcatttac ttaacaaacc agatgaatgc ctggcacatg ccatcactag aaagggcact  26520
gaggatgcct gagtttccct agatgggaac actaggggaa gcctattttc cagcaggtca  26580
```

-continued

```
acagcctctt gcctccaatt ccaaaatcca caaactctca aaattggaaa atgtgtttgg  26640
taacttgttt ggcagcaaga cctggcctta cctgatctga acttatttgg cagcaaaaac  26700
ctggcctgag ataacaggag gctattggtt atctttatat ttgccctcaa atgtgagtgg  26760
ttatgtattc tctgcagaaa tattaggatg tttgatccag ggggaatagc ccaggcccca  26820
ctggcagcat tatataatat atggtgtatg ctccatgatg cctttctaaa atctgaaaac  26880
ttctaaattc tgaaactcac ctggtcccaa gcatttcaga aaaagaactg agaacctgta  26940
ctctaaaagt aggaaggaag tagaactcct tttgatagga aagaagaggg aaatgcaaga  27000
gagagatcta tttatttcag agtgacagta attaatacta gtgactaatt aatactcttt  27060
aagtataaat gagatgtcct tttttataaa atgttcacag tttttctggg aggtgaaaag  27120
ggaacattca gcagatgtaa aaaccgaaac ccagatggct taagcaaatt gctcacgatt  27180
gaactagaat cagaccccag gtctctcact ccgcaagtct gctagatgca cccacgctct  27240
gttctgtctc cccagataag ctccacaaac ccaaagctac acagactgag gtcaaaccat  27300
ctgtgaggtt taacctccgc acctccaagg acccagagca tgaaggatgc tacctctccg  27360
tcggccacag ccagccctta gaagactgca gtttcaacat gacagctaaa accttttca  27420
tcattcacgg atggacggtg agcccgggga gggagctctg cggctttata taagatttga  27480
ttccctttgt tttggtcaat tagaaagaat tctggtgttt ccagattcca aaccctcttc  27540
ccccctttcc ttgtgggctg cttgtatttc agacagctgt gaagaatgta acgggcattc  27600
actaaggggc aatctggact ccagcagggt ggtattaatg atggcataca acgggctttc  27660
agaaagtggc tctcctgagg gcagcagccc agctccactg gctcttaagg acccctctaa  27720
ttacacttaa ttacgctggt caaccactgc ctggaggggg ctgtcctgcc gtgagagctg  27780
agcttaacta aagcaacttg actggctctg agaacctatg agtagccagc tggcctggat  27840
tgctgactgc ccttggcata gtgccctcct gtttgcatag agatagcccc gtttaaaggc  27900
actggggctc tttatgtgcc ctagctgagc aattcacatt gaaaagccca tgacaaactt  27960
caacaaaaaa gggctttagt gctcagcttc agaagctttt gaccagccag gaatttattc  28020
attcatataa tgacagtctg tagggaaatg gcactattaa gtgagcagat ttctgcctgg  28080
gctaattgga aggggacagt cctcctctta atgatgagaa attcatatct gttacatgct  28140
tttggggtct ttaaatctgt catccatggt tgaggtcagg ggcaggagag ggtaggtgcc  28200
tgcctaccta gttgaatgaa gagatgatta agagcctgtc taaccctgct catcacacaa  28260
cctacaatca gaatcatatg tgtgaatctt tttaaggccc cctgtcaaaa tgcaaataca  28320
agctgcctgc gacttacaag taggttgcat tccagaaagt tcttttgtaa tctgtttgga  28380
acttggaaca gcagtttccc acagaagcaa gattgtaaat ggtgtttggg ttcccaggct  28440
aggcacagaa aatctatcta tttgataatg tgcttgtgga taggtttaca actggaccta  28500
gtcaccattt ataactttgt ttctgtggaa aaatacattc tgagttgtaa tttgggattc  28560
cggggacaga ttttccctac tctggggtca agagggatgg cagagatggg ttgtgggaag  28620
gggtcatttg ttaactctgc attcacctag gagacagcat ctccctgcgt ctctaagaga  28680
gaagcaattt tccagggcaa ccctccctag ctgcctttga aggatggacc aggccacttg  28740
cctgcctgta acagggactc agaccagcct catgccagta tcacccttaa cacgtatctc  28800
atagtggccc taacagacag tggggcaaca gtataggaca ttagctagga aagttttgat  28860
gggaaatact ggggatgtaa ggagcaatgg aagacaaata cctgcgtagt gattctgcct  28920
gtgctggtcc tgctcatgtg caaatgtttg gtccctgagc agccaatgtg cagattctaa  28980
```

-continued

```
aattgtctgg gggcactggg catggtggct cacgcctata atcccagcac tctggaaggc  29040
ctaggtggga agatcgcttg agcccaggag ttcaagacca gcctgggcaa catagtgaga  29100
ccctgttgct gcaaaaagtt taaaaattac ccaggcatgg tggcatatgc ctgtaaccca  29160
gtcactctgg aggctgaggt gggaggatca cctcagctca ggagttggag gctatcatga  29220
gctgagattg ttgtcagtgc actccagcct gggcaacaga gtgagaacct gagtcaaaaa  29280
aaaaaaatta attgggaaga gggtcatata gaaaggaatt ccatattttt taggatttct  29340
gaaaccaaga ataaaaaaca acttccactt ttctctgcag atgagcggta tctttgaaaa  29400
ctggctgcac aaactcgtgt cagccctgca cacaagagag aaagacgcca atgtagttgt  29460
ggttgactgg ctcccccctgg cccaccagct ttacacggat gcggtcaata ataccagggt  29520
ggtgggacac agcattgcca ggatgctcga ctggctgcag gtactggggg atgagaggga  29580
gtctcctgtc accagcagga tctcaaaccc aatcttctta agaaatgcag gtcatgcatc  29640
tgttgccatg aacttctgga gtctgataaa aatctttgag attaaaagtt ttattgaatt  29700
aagtattgtt tggaatactt gaaagctggg actttttgag agccttttaa ttattgatag  29760
atctctggat ttttcctgtt acttaatttg ctgaaaattg gccttatggg ttgtttcttc  29820
ctgatcttag aaacagatgc ccttaggttg gttggggatg gccaggaacc aggccaggct  29880
tgtgatctga aattcctaca aagactgctc ttgtctctga agcatggctg tgctgagggt  29940
ggggaggggg ttatttcaaa aatgcagcct aatatctctt ttctttgaga tggagtcttg  30000
ttttgttgcc caggctggag tacagtggtg tgatcttggt tcactgcaac ctccacctcc  30060
caggttcaag cgattctcct gcctcagcct cccgagtaac tgaaactaca ggcctgtgtc  30120
accatgccca gctaattttt ttgtattttt agtagagatg ggatttcgct gtgttagcca  30180
ggatggtctt gatctcctga cctcatgatc tgcctgccta ggcctcccaa agtactggga  30240
ttacaggcat gagccaccgt gcccagcctg cctgatacct cttttataat atgaagtgtg  30300
gaaaacagat cttgaagtct tatatttact tttttttttg agacagagtc tcgctgtcac  30360
ccaggctgga gtgcagtgcc atgatcttgg ctcactgcaa cctctacctc ctgggttcaa  30420
gcaattctcc tgccttagac tcccaagtag ctggttttac aggtgtgagc caccatgccc  30480
aattaatttt tgtattttta gtagagatgg ggtttcacca tgttggccag actagtttct  30540
aactcctgac ctcaggtgat ctgcctgcct cggcctccca aagtgctggg attagagacg  30600
tgagccaccg cacccagcct atttactttt aataggttaa taatctgcct gagatcagtg  30660
gatttagctg ggagaaggca gggcagggta cactgtcaaa gcggcaccat tatctgggca  30720
attccggcct ggccttcctt gttcccatgg aatgggatga attctggcag aattctggtc  30780
aggattctcg agcagtccct ctgtcctcta cctaagctct tctatagagt ttggtttccg  30840
agccatgggg ttacctcctt accccccaga tgagtgctct gacaggggac aatgcgtcaa  30900
gtctggggtc ccacatgggc ttgtgaggag gaggttggca gctcctgggg ctgggtggag  30960
gtcaggcctt agagggcagg cagagggcat tctgctgagg gctgtggttg gcactgcagt  31020
ctccagtgag tacggcagct ttgacctcct caccatcacc ctcccctctc ttagatactg  31080
ccagaaagaa caggaaatgt gtagggaaca gccacatatg cagcctccag tcataccctc  31140
caccctgtcc ccacacttgg catttgcagt gccaccaagt ccttttggcc tcccctaagc  31200
tggctgtgac ccacacatgt agcatcacca gcaaagccag tggggccctg gggagtctct  31260
gtgcccacgg cccctgcatc tcctcctgct ccgtgactga gttgttgaac tgctggtgat  31320
```

-continued

```
tctgggggct ctggaccctg ctcttctgct cacatacttt ggtgactttc tataggagaa  31380
ggacgatttt tctctcggga atgtccactt gatcggctac agcctcggag cgcacgtggc  31440
cgggtatgca ggcaacttcg tgaaaggaac ggtgggccga atcacaggtg agctccactt  31500
ccatcactaa agggctccct cagctgcgct aagccggaat gctccccaat gaggcagcag  31560
agtgagtcat agaaagttag ctttggaagg aacctggaaa gcatctaatt caaaacttcc  31620
caagcgtttt tagtcacaag gaactttttt ttttttttcc aaattgaact cgcataggcc  31680
cgcagtatat gagacacaga aagggggggtg ctgtgggtga agtggggtgg gtatatggcg  31740
gcttgtgtta gccttgccag tgtgggcgtt ccccttccct ataggcatct cagagtctca  31800
gagcaccagg gaacacagtt tgaaaaccat aggcctggtc caataggtga ggaaacaaac  31860
acggagaggt gagacaactt gcccaggggc aaacagctaa taactcaaga gcggaagctg  31920
gatagagccc tggccccaaa gcttttgggt gttcccttca ggtctccacc caaggactca  31980
ggggaaaaga atgaatagta gattttagtt tgaattctgc ctctgatttc tatcttgtct  32040
cccaatagcc tctttcccat gttaaggtag catatttatg aatgagagct accaatttgg  32100
aaagggtggt tcaactttgt aataaaagga acctttctga tattggtccc caggggggtca  32160
acagaaaatt gaattttcca tgttgaaaac tgcatcttag tgagctttta acatgagagt  32220
ttggattaaa tcatttaatg attgtgaaaa gtgtaaaagg ttttctttct catttttggg  32280
cccctcaagt atatacacag agattcctct atgctacaat taatggtaaa tttgttgccc  32340
tgaacttcta tccttcttcc agcattattt tatttaaaat taccccctagc ttcccccctta  32400
ctcccaagat tctaagggtg atcacctaga aggatagatc tgaacaattc ctttccctgc  32460
agtgttttca ttttaaaaca aaactcaggc tgggtgtggt ggctcacacc tataatccca  32520
gcactttggg aggccgaggt gggtggatca cgaggtcagg agttcaagac cagcctggcc  32580
aacatgatga aacactgtct ctactaaaaa tacaaaaatt agccagctgt ggtggcgggt  32640
gcctgtaatc ccagctactt gggaggctga ggcaggagaa tcgcttgaac caaggaggta  32700
gaggttgcag tgagccgaga ttgtgccact gcactccagc ctgggtgaca gagcaagact  32760
ccgtctcaaa aaacaaaaca aaactcaggt agaagagagt ccttagctaa ataacgattt  32820
ggtaaaggta gaatttcaga tttcagtgac aagctgatat ggtagaattt taaaaagaat  32880
atttgtgaag ttttcctggc tctcctgaat cctgtccctg ggcttgagtc tagtatgtgc  32940
gtgcacacac atgagcatgc atgcacacac atgcctgttg atccaatgac ttgattcatc  33000
ccagcttgag agctttattt ttgatttcca agactgtggg gcttgagctg cccaaagcgg  33060
gctatgattg tgtggccacc catgactgct cattaacccc ttgctggtgc aaagcagttt  33120
gactggaagc cactcgggtt ccattgtctg agcgcctctt cctagcccct gaatgagagg  33180
tgtgatgttt cagatccagg cacctgagtt caaattgtag cacacaccac agtccaggcc  33240
cagaatgtca gtaacgatga caaactgcac atcttgcctt tctctatttc taaatctgaa  33300
atgagatggg gctagggagg gaactttcca gttctttccc cctgcctgtt tgagtggcat  33360
ctgctggggt gagggctttt ctcctgaggg tggcaggaga gccaggcaga atgctaatta  33420
gtgctctggg atgtttgcat ggagcatgat gcccacatgc cctgagcatg gtcccttccc  33480
tctggccttt ctctgtagag aaggggcctg gcctctgtcc agttgccaag cagcacccct  33540
gacacacgct gttgtgtatg tctgatgggg gaggctgcgt cctctccttt ccccttggta  33600
gacttctcat ggacctgtgg acaaggtgat cgcaactggt aagaggacag attgagactt  33660
gcatggggtc ctgcgtccag tgatgccact atgctaaggc caccaggcag tccttagcct  33720
```

-continued

```
gggccttgca agggtatatc tgaaccccaa tcttgcttgg accagagggt gtggatgggg  33780
gtttgctaga gttttacttt cttaggcttc tgagagaagc ctgtgatact aggaaagagg  33840
tcatatattt atagttgaac ctgtgccttg tttgctataa tcaggtaagc aagcagatga  33900
atttattcaa gaaatgtgtc catatgtgca ggctagatgc tagctaatgt caaatacctc  33960
atgtgtggcc gggcgtggcc gggcgcagtg gctcacgcct gtaaccccag cactttggga  34020
ggccgaggtg ggtggatcac ctgaggtcag gagttcaaga ccagcctggc caacatgatg  34080
aaaccccatg tctactaaaa gtacaaaaat tagccgggca tggtggtggg tgcctgtaat  34140
cccagctact caggaggctg aagcaggaga atctcttgaa cccaggatgc ggaggttgca  34200
gtgggctgag attgcgccac tgcactccag gctgggtgac aagagtgaga ctctgtctca  34260
aaaataaaaa ataaaaaata aaaaacaaac aaacaaaaaa cacctcatat atgacagcta  34320
ctctatgcta tctctgaacc acatagcaac cctgaacatt ctacggaggg ggaaactagg  34380
actcagtgat taagtaaagg gcccaatatc ctgggcccta taagtagcag agctgggact  34440
caaacccatg ctgtcagatt ccagatccca tgcacctcac tgctgtgcca tgctgcctct  34500
cttctgtgga cagagataaa gtagccaggc atggtagtgc atgcctgtaa tcctagctac  34560
tcgggatgct gaggtgggag aatcacctga gcccaggagg tggaggttgc agagagccga  34620
gactgggcca ctgcactcca gcctgggcaa cagagtgaga ccctgtctta aaaaaaaaaa  34680
aaaaaaaaaa agtagccgtt gaactacagc aggccctgcc ctgccgggcc agaatgcaca  34740
gccctggaag ttttacatgt gtgcatgtgt gtgtgctcca tttgctggac aaagcaactt  34800
tggaggagtc tatgactgaa tggaagaagc ggcggaggtt ctctatctcc tctttattta  34860
aggaggcagt tctccctgtc attcatccct agttaaaaaa gttaaatgtg ccactgtacc  34920
cctgaatctg tgggccacag atatgtgtca gggacagtca gagcagggca ggcaggctct  34980
ggctgggtag gtgaaggccc agccttgcct gccagccagc ctgtgaaacc ccatcagctg  35040
cctgcattcc tccagcacag cctggtttcc atggcactga ccgtctggtg gggacctttg  35100
ttcacaccaa gtaaagagcc tctctcttgt attgattgca aagcagaatg ttgctctctt  35160
tctctttcct ccaggggaca tggtgagagg cagggagagg ccgctgtgtc agtactgcgg  35220
tccttgcggc ctctgaaatg ggttgtcgtg ggctgttctg ggagcacact gcttttgtgc  35280
catctttctt ttgggtcctg ggctagggat aaactctcaa gcagcctggg ctccctttct  35340
gtcttggttg cacataaagt tatctaaatt tggctgggtg cagtggctta tgcctgtaat  35400
cccagctact caggaggctg aggcaggaga atcgcttgaa cccaggaggc ggaggctgca  35460
gtgagccgag atcgtgccac tgcactccag cctgggtgac agagcaagat tccaactcaa  35520
aaaaaaaaaa gaaaaaaaag ttatctaaat ttttggaaac tatttagcgt ttcagcctct  35580
accagttctc atatgagtaa tgagttctgc aagttgaccg tccactctag acggtagctc  35640
tgcctcttgt ttatcctgaa actaccatct caagtctcct gataggctcc ctggttctaa  35700
tgtgctgtgg tctggtgaac acggtcgtta accatgtcct cctttcagga ctcttgttgg  35760
tcacatctcc tcccagcctt ggtgtttcga ggccaggttt tctcagccta ggcaatattg  35820
acatttgggg ccaggtaagg ttttggtgtg gggtgtgtgt gtgttgggat tgacttgtgc  35880
actgtagaat gtttagctgt attcctggcc tggccctgct agatgctagc aactctctcc  35940
atcagaatgg gggcaataaa aaggtctcca ggaatttcca gatgtcccct ggggggcaaa  36000
gccacttgta gtggtgaacc actgttccag cggcccttcc ttcctggcac atttcatccc  36060
```

-continued

```
ttaactttct ccaggtcctt cctgtgtgtc tgtggggcaa agagctgttc tggttgggat  36120
aaatctggtt cccataatca cttgggcttg gtaatagtag ctaatactga caggcactca  36180
gtctcttaag atctcacgtg gactttgaat taaggtataa attcaggttc cattttataa  36240
atgataatga aacacaggga agtttttcaa tatttggccc acagaatacc tacttttagg  36300
atcatccggg gaataaatat ctatttctat gtgccataat tcatatctac ccactaggag  36360
ttcaggcact tgggaatctg cattttatac tttgcaagtt ctcttttgga atggttttac  36420
attaatgcag ttttcaaatc aaaagatggt gaaagtctct cttactgctc tgctacctgt  36480
ccgtttccct tacccactct ctcccccaac gcacacgcat acaggtaact agttgcttgt  36540
gtgtccttcc agattttttt gtagctgtat ggtggaattt aaatttaaca agctcccaat  36600
ttcaaatatg agaaccagtg ctctcaacag tgctgcttgc ctgctcaaca caaaatgttt  36660
ggaggcggaa aggttttctc acggtggctg caaaatagag gaattctgga ggcctgatgt  36720
atggattctc agtgtattgg gtgtcctctt ctctctcacc attccacccc tgggcctgat  36780
taaaggaaga agaataaatt cagatacaaa tagctccgtt tggggagact ggattctcct  36840
tccagaagga tgtaggcagc ttagttattc tgtaaaaatt ctgctacaat taaggacatg  36900
aaagatgctc agtggcagaa tgaatgggac aaatggctta gtttcaggca gtctgagttc  36960
tttctagaac tgcttcagtt ttaacaggag cagttccttg gagctgtgtg gcagcgaaac  37020
ttgtggctag ttgacggggt ttggctgagg tgacgggata catgaaggct tcagaagaaa  37080
gtataaattc cataacagta ggatttaatt tctgcaatga tgtcttgggg tcaactgcat  37140
atggaaatgg gtttcttatt ttcttccatg ctttccatgt cttgattctc ccagctggtc  37200
tcagaagtca tcttcattct gcacactcag acttaacttg taatcaggac tcactgacca  37260
ggtgcacctg acaccacagc tgttttgggg cctccttctg ctgcaggttt ggatcctgcc  37320
gggcccatgt ttgaaggggc cgacatccac aagaggctct ctccggacga tgcagatttt  37380
gtggatgtcc tccacaccta cacgcgttcc ttcggcttga gcattggtat tcagatgcct  37440
gtgggccaca ttgacatcta ccccaatggg ggtgacttcc agccaggctg tggactcaac  37500
gatgtcttgg gatcaattgc atatggaagt gagttccctc ttttctgctt tgtgtttgac  37560
tcagtttatt ccatctcctt ctaaatcagc cagagccttt agcactgcag gcactattta  37620
ttcattattc tcacctccca ccacagaggc ctccaatgct gtatttaata tttctcattg  37680
ttccccaaga ctaaccaacc cagtggttcc tgctttgctt tctcacgctt taaggtcaca  37740
gttgttattg attaatttct tttcttttct ttttctttct tttttttttt ttggaaaggg  37800
agtttggcct cttgttgccc aggtttagat tgcaagggtg caatcttggc tcaccacaac  37860
ttccgtctcc caggttcaaa cgattctcct gcctcagcct cctgagtagc tgggattata  37920
ggcacatgct accataccca gctaattttt gtatttttag tagggacggg gtttcaccat  37980
gtcagccagg atggtctcga tcttctgacc tcgtgatctg cctgcctcag cctcccaaag  38040
tgctgggatt acaggcataa gccaccgcac ccggcttgtt atgataattt ctaaaatgtt  38100
ttttcatttt agggtgcaga catgaatgga ttaccaacaa aaggaccaac agaaatctgt  38160
gataaaaaga aagactaaag aaattttcct aaaggacccc atcatttaaa aaatggacct  38220
gataatatga agcatcttcc ttgtaattgt ctctgacctt tttatctgag accggaattc  38280
aggataggag tctagatatt tacctgatac taatcaggaa atatatgata tccgtattta  38340
aaatgtagtt agttatattt aatgacctca ttcctaagtt cctttttcgt taatgtagct  38400
ttcatttctg ttattgctgt ttgaataata tgattaaata gaaggtttgt gccagtagac  38460
```

-continued

```
attatgttac taaatcagca ctttaaaatc tttggttctc taattcatat gaatttgctg  38520
tttgctctaa tttctttggg ctcttctaat ttgagtggag tacaattttg ttgtgaaaca  38580
gtccagtgaa actgtgcagg gaaatgaagg tagaattttg ggaggtaata atgatgtgaa  38640
acataaagat ttaataatta ctgtccaaca cagtggagca gcttgtccac aaatatagta  38700
attactattt attgctctaa ggaagattaa aaaaagatag ggaaaagggg gaaacttctt  38760
tgaaaaatga aacatctgtt acattaatgt ctaattataa aattttaatc cttactgcat  38820
ttcttctgtt cctacaaatg tattaaacat tcagtttaac tggtagttca ttttctttta  38880
aagtctattg aaatattcaa aagggaaatt tttcaccacg tcagaaggca gaatttggat  38940
gttatggcat ctgtgtagtg gtgggacaac aattactatt gttgcgtaac aagacactcc  39000
aaaatttagt ggttttcagc agcagtgact cgactgggca gttctttgct gttctgggct  39060
cactcatatg gctggctggg cctgggtctg gacctgggcc gctatgtgat ttttatcttg  39120
ggctttgaaa attcagtgta gggacctata aatattcaaa gatgatgaga tgcatcctta  39180
tatatttttt gtattcactc tgaagctggg aaagattaaa aggaactcct gcccttgggt  39240
ccctaatgaa gtctgggtcc taactcgctc tattaagttc tgtggctggt caagtcactg  39300
atctaccttg ggctttattt gatataaatc atataaatca gcaggtctca gcttttctgt  39360
ccaaagccac ctgagggata agataaattc tcattagcaa ataaactttt ttaaggtata  39420
aatactatta taaaaataac agatatttac agtacaacaa tgcaagagga tcctaaatga  39480
aaagcgaatg ttttttctca actctcattc ccttattcca gctccacaga ggtaaccaat  39540
tgtttttttt ttgttgttgt tgtatggttt gtttttgtta gacagtagtc ttttcctgaa  39600
cagtgctgct ccttgtggag caaggctaat tcataggcag tgcatccaga gtctgcccca  39660
gttgattttg tgtgtaacct tctagcaact ttttgaaaat taatttgttc ttaaatatgc  39720
acatcatttt tatttattta tgtttttgag acagggtctc actctgtcac tcaagctgga  39780
gtgcagcagc atgatcacgg ctctctatgg cctcgacctg cagtcctgaa gtgatcctct  39840
caccttagcc tctcaagtag ctgggactac aggtgcacac caccatgccc agctaatgtt  39900
ttttgtaatt ttttttatag agacagggtt tcgtcatgtt gcctgggctg atctcgatct  39960
cctgggctca agcgatcctc cactttggct tcccaaagtg ctgggattac aggcatgagc  40020
tactactgca cctggcccac acatcatctt ttaaaaatta agtaatattg caacgtttct  40080
aattgtccct acttctttgc tcctcaaagg ttttacctac tgagctgtgg gctttttaaa  40140
tttatctcca tatttataaa taaattataa aaatataaaa atataaacat tttatttttt  40200
gagacagggt ctcactgtca cccaggtgct ggagtgcagc ggcatcatca tagctcacta  40260
cagcctccaa ctcctgggct caagtgatcc tcccacctca gcctcctgaa ttgctaggac  40320
tacaggtgtg tgccaccacg cctggctaat tttttgtaga gacggggtct tgctctgttg  40380
cccaagcgag tctcaaactc ctggcctcaa agtgatcctc ttgcctcagc ctcccaaagt  40440
gtcgggatta caggcatgag ccactgcctg gctatactgt tatattttga gccatcaact  40500
tgagacattg tttcccataa tggttgagat gccgctatct tacactgcct ctgctcctcc  40560
cacacatcct cccaagtgct tttgtaaatt ttgcttacat catcagtgtt catagcatga  40620
gtgtgccagg tgtctttcat ttgcccctcc caagtctctg ctcccctcat cctgctttca  40680
gcccaaggaa gctgtataga catcaacaga cttcccatgt ctctgggttc tgctgggttt  40740
ggccaatagc gatccatagc aggagatggc tggagggagg agaatgaagg cagagtgttt  40800
```

-continued

```
attcccttgg ccctctctct gcaaggtcac ctcaggccaa ctgttcctca gccagaagtc  40860
actgtgcctc aaggaacact ccaggcagcc aactccacct gacttctttt atttttccta  40920
acctgtcctt caccctgccc ttttgggccc aggggtggtg gtatttctgt tactggctct  40980
gggctactgc ttcctctcaa gagtgctatc tggcttgctg ggacactgcc tgggagaata  41040
ctattgctca ctgcacaggt taatgcactg tgattgcctc ccttttaata tacaggtggt  41100
gtcttcctgg agtgaccagt ttaccttctc cccatacacc tctcctgcct agttgttgcc  41160
tagacctggt gcacactgca gtcctcggga ctttctgttg ccaccctcct gtattggacg  41220
tcttgtttct ggatttccta tcctcttcct tcttggttta tccctcattt tttctgtagc  41280
acagcagttt tctaattcaa tacttttagg aggttgagta tggataattt tggaaagtgt  41340
ccccgggatg attccaattt atttaagcct gttttccaga gagctgcggg tctcctaagg  41400
cctttctcat ttctaacaag tctccctctc tagaacactg gttcccagtc gttgttttca  41460
tactagcaac attttaaaag caggataggg gtggctagta tgcaattgcc aactttggat  41520
ttttccaagc aggagtatat caaaaagcta caatttatta ccagtatttc gtaaaagaca  41580
gtttgacacc agaagagtga aaaagaacat gggaatagtg gacaaaaata gccatcagtt  41640
tgaataagcg tatgaaaagt gttaatttta tgaaaaattc actattttgt tcatattttt  41700
cttattttgg aggctaattg ttaaaagctt ttatcagtta tccatgggct ggagttggta  41760
gccactgttt gataccacac aaatgtttct ttgccctaaa atatcaacat ctgtctgtgt  41820
aaaggtcagg gctgcctttt tagtaagagc taccctttgt taaacacatt gtacctgcac  41880
tgttcatggg tgtttcacac acacaaacct acctggtctg cataaacctg aaatacagtc  41940
aagaaaacag gatccaccgg aggcggtgac tcaagcctat aatcccagca ctttgggagg  42000
ccgaggtggg aggatcactt gaggccggga gttcaagacc agcctggcca acatggtgaa  42060
accctgtctc tactaaaaat acaaaaatta gtcgggcata gtggtacaca cctgtaatcc  42120
cagctactcc agaggctgag gcatgagaat cgtttgaaac caggaggcag aggttgcagt  42180
gagctgaaat tgtaccactg cactccagcc taggtgacag agcaagactg tctcaaaaga  42240
aaagaaaaag aaaaacagga tcccagcctg ggcaacatag ggagacctcg cctccaccaa  42300
aaattaaaaa tttagctagg catatggtga tgtgcacctg tggtcccagc tactctggag  42360
gctgaggtgg gaggattgct tgaacccagg aggttaaagg ctacagtgag ctgtgatcaa  42420
gccactgcac tctagcctga gcaacagagc aagaccctgt ctcaaaaaaa aaaaaatcac  42480
tattgcccca gcaatggatt taatttaatt taattttaat ttttttttt ccggaccggg  42540
attttggctc ttgtaccgca ggtgggagtg caatgggcca atcccagctc acgggaattt  42600
ccgcccccca ggtccaagca attctccttg cctcagcctc ccaagtagct gggattacag  42660
gtgcccacca tcacacctgg ctaacttttt gtatttttag tagagacagg gtttcaccac  42720
attggccagg ctggtctcaa actcctgacc tcaggtgatc cacccacctc ggcctcccaa  42780
agtgctggga ttacaggtgt gagccaccgc acctggccct aaggagtaca ttttattagc  42840
attttagttt atttaatatt cattgttcta tttaaatttt cttattctaa ttgtgacgtt  42900
ttacattttt tcagttttta tacaggtttt gaatttatat ttcataatat ctattagcat  42960
gatgactttc acatttatac cttttattca gatggaattc atttttgttt tggggggggtt  43020
gatggtttta acttctactt tagtttcagg ggtacgtatg caggtttgtt atgtagttaa  43080
atggtgtgtc acaggagttt gctgtacaga ttatttcgtc actcaggtaa taagcatagt  43140
acccaatagg tattttggaa ttcatctttg ttgcgtgtta aaataggaat ctaattttgt  43200
```

-continued

```
ttctctttgt caaatgagcc tactttctca tcatccatcc attcctttcc caaagactaa  43260
taggcccctt ttatcataca taaaatttcc gcatatatgt ggaaaggatt ttattttatt  43320
ctattctatt ttattttatt ttgagatgga gtctcactca gttgcctagg ctggagtgca  43380
gtggcgtgat ctcagctcac tgcaaactcc atctcccagg ttcgagcgat tcttctgcct  43440
cagcctccgg cgtagctggg actacaggca cgtgccacca cgcccagcta atttttgtat  43500
ttttagcaga gacgtggttt caccatattg gccaggctgg tctcgcactc ctgacctcgt  43560
gatcctccca tctcagcctc ccaaagtgct gagattacag gggtgagcca ccgtgcccac  43620
ccaggatttt atttttgtct cacactgtcc tcttatcaat tcaaatgttt acaaaacaca  43680
aatactttct tttttaccat gtacctttaa cattcacaac aaccctgagc agtattgtct  43740
ctgtttctta aatgagcaga tagagactca gaaaggctgt atttagccta aaactcacat  43800
aatgctggat gacacaccaa gaattctgat tccaaactaa ctgctctttt cccagattac  43860
ctcctgcctg tttaagcacc tagtttctta tatctaattt catctattta tttaaatatt  43920
cattgaatac ccatgatgtt ccagacacta ttctagcttc taagataacg gcagaaaaca  43980
agccagataa aaatctgtgc catcagagag cttacatggc agagggctca gggtagctct  44040
gaacacagag gtgacacctg agaaatacca tatttgatga caaagactgt tctagtacct  44100
actttgtatc catccttcca aggggtctgg ggcttcagct tgtttggaga gtcaaaggaa  44160
gtcctgtgga agttcccctg actctaacta gtaactgaac ccccaagcca aagaaggcac  44220
ttgcagtcat ccaggctatg actcttcctt tgggaaattt caacaatttt ctttactatg  44280
ccagagacac cattttctgc tttcctctga catctgaacc aagttaagaa cttatctctt  44340
attgtctaac ccaactccct acagccatta tcaagcctgg tttcagaatg tcctggtaga  44400
gatggacagt ggagtttcca ccatcactaa agccctttat aaagagcttc cttgtcattt  44460
agaaatgttt tcacacttaa gaccagaaat aaagtcaaac tgatgtaatg cattatactt  44520
catagtcata gatcaattta agattactaa aaattgacta caggatttaa tcatttaaag  44580
ggtactctgg tctatctcgc tggctttagc agagaaaaaa ctaattcctg ataaacggat  44640
ggcaagatcc aatttccctt ttaataaata gtaattggta gggggaaagg ggaaataggg  44700
acggaattgt taaaagatac aaaattacag ctagtggctg ggcccggtgg ctcacaccgg  44760
taatcccgac agtttggaag gctgaggtag gtggatcact tgaggtcagg agttcaagac  44820
cagcctggcc aacatggtga aaccttgtct ctactaaaaa tacaaaaatt agctgggtgt  44880
ggtggtgcat gcctgtaatc ccagctactt gggaggctga ggcaggagaa tcacttgaac  44940
ccaggaggcg gaggttgcag tgggccaaga tcatgcccct gcactccagc ctgggctaca  45000
gagcaagact ccatctcaaa aaaaaacaaa aaaacaaaaa acaccaaacg aaacaaacaa  45060
gattacagct agacaggagg aataaattct agtgtcctat accactgaag ggtaaaacta  45120
gagttaataa aatatggttt caagtaacta gaaggaggat attgaatgtt cccaacacaa  45180
agaaatgata catgtttgaa aggatgggta tgctaattat tccaacatga tcactatacc  45240
tgtatgtttc gaaacatcac tatttnnnnn nnnnnnnnnn nnnnnnnnnn nnnnnnnnnn  45300
nnnnnnnnnn nnnnnnnnnn nnnnnnnnnn nnnnnnnnnn nnnnnnnnnn nnnnnnnnnn  45360
nnnnnnttgct gctaaaactg aggtgtaggg cagtgaccaa ttttgggggg gtttcttatc  45420
cttttactgc cttggctgct gacagcatat cctgtcttga ccccaggcag ctctctccac  45480
tctgatgctg tgccctccac atgtcctgcc ctgatgctca gtctttccct ctcccggttt  45540
```

-continued

```
aatccaagta gctctgcagg gtttggaggt ccatgcaagg ggattttact ccctcctcag  45600
aatataggat gatggccttt ctttcctttc ctttcctttc ctttcttttc ttttcttttc  45660
ttttcttttc ttttcttttc ttttcttttc ttttctttac tttacttttg atggagtttc  45720
actcttgttc cccaggctgg agtgcaatgg tgtgatctct gctcaccgca acctccactt  45780
ccaggttcaa gtgattctcc tgcttcagcc tcccaagtag cagggactac aggtgcttac  45840
caccatgtac agttaatttt ttgtattttt agtagaggtg gagtttctcc attttggcca  45900
ggctggtctc aaactcctgt cctcaggtga tccacccacc ttggcctccc aaagtgctgg  45960
gattacaggt gtgagccact gcccggctgg atgatagcat ttcttaaggc tgctggtgcc  46020
aatgaggcag ggttggggtt ggttatgcca aatttttttgt aagatcccag aaattatttg  46080
ggccagaaaa tccaaattgt atgcctaact ttgtaaccaa ctgtctctat gaccctgagc  46140
agattacctc accccctatgg acctttgggt cataatcttt aattgaaggg attagactag  46200
aatgaggttg tcaaacatct tcttaaagca tcagctagta aatgttttag gttttgtggg  46260
ccgtattgcc tctgttccaa ctctgctgat gtagcatgaa agtagccatg acaatatata  46320
aacaaatgag ggtgactgtt ccaataaaac tttatttaca aaaacaggtg gccagcaggc  46380
atggtgtggt gcacctgtag tcccacctat ttgggaggct gaggcaggag gactgcttgg  46440
gcccaggtga ggatcacttg agcccaggag tttgaggcca gcccaggcaa cataatgaga  46500
cactgtctat aaaacaaaaa caaaacaaag caaagaaaaa aaaaagaggt agcaaacctg  46560
caagccatat tttgctgagc cctgcgtgag atgatgttta ggatctgatc catttgcagc  46620
attctgtggc tgtatagccc tattaggagg tagtgactcc tgctgcacag ctggtctgca  46680
tcaccctact tagcacttat tatatgggcg ttcttgctct ttattgcttt gtgtgtattc  46740
gtgctgtctt cccatcaaga gagtgaacag ttaggcagca tgaatggcct taaattcctc  46800
tacatcttaa tgggaaccta gcaccttgct ggacattaat gaagcattac acaggtcggg  46860
tgcagcggct cacatctgta atcccagcac tttaggaggc gaaggtggga agattgcttg  46920
aacccaggag ttcaagacca gcctgggcaa tgtggtgaaa ccctgtatct acaaaaaacta  46980
caaaaattag ccaggtgtgg tggtcatgtg cctgtcgtcc cagatactgg ggaggctgag  47040
gtgagaggat cacctgaatc tcggaagttg aggctgctgt gagcgggggg tcgtgattgt  47100
cccactgcac tctaacctgg gcaagagtga gaccttgtct caacacaaat aaacaagcaa  47160
aagaattaca tgaaaatact aacagcaaca ataaacagct atcactgttg aggagtacag  47220
tatttattat ttgagtgtct aatcatcaag aagggctcat cctgcatgct ttttatctct  47280
cccaccccca gcaatcacag aggtggtaaa atgtgagcat gagcgagccg tccacctctt  47340
tgttgactct ctggtgaatc aggacaagcc gagttttgcc ttccagtgca ctgactccaa  47400
tcgcttcaaa aaggggatct gtctgagctg ccgcaagaac cgttgtaata gcattggcta  47460
caatgccaag aaaatgagga acaagaggaa cagcaaaatg tacctaaaaa cccgggcagg  47520
catgcctttc agaggtaacc ttcagtccct ggagtgtccc tgaggaaggc ccttaatacc  47580
tccttcttaa taccatgctg cagagcaggg cacatcctag cccaggagaa gtggccagca  47640
caatccaatc aaatcgttgc aaatcagatt acactgtgca tgtcctagga aagggaatct  47700
ttacaaaata aacagtgtgg accccttttg tgatgtggct atcagtccat gatcacaata  47760
tcaatatctt aaatttctat cttgcattta actttcaaag ctgtttcata tttgttttct  47820
catttgatca tcacaagaaa cctgaggcag atgaacaggg gaccaaaatg acatgttaca  47880
tttttataat gtgctgtaaa atcacaaggt tttctgggta ctgtgggtat tattttacat  47940
```

-continued

```
atgaggaagt tgaggctcag agaggttaat accttggtcc ttaatccagg ggcacgtagt  48000
tagaaagtag ctaagtgaaa atcctcaaaa gatctaactc ccaagtgcag ggctccttcc  48060
atactgcagt ggcctcttat ggcattggac agaacaagag cagatggggg ctgcaggctg  48120
ggctcaacca aaagaacacc agccctaaaa tctctgtgct ggtgactcag tttgggtcag  48180
gggtctcctg tgatgacaag caagggttac aagcatcttt gttctgctgt cactgcagtt  48240
taccattatc agatgaaaat ccatgtcttc agttacaaga acatgggaga aattgagccc  48300
accttttacg tcacccttta tggcactaat gcagattccc agactctgcc actggaaatg  48360
taagtcatcc gtttcccttg ctgggttcgg gacagagaac aggttggttt gagaatgaga  48420
gagcacaagg gagcgtgtga acgagtacag cacgcaggag agtgcagtcc gactgctcag  48480
ggaggagcca ggtggtctag ctggcctctg cagtcctctc tcccactgca ccttctctac  48540
caagccctga ctcagcgttt cggggagaaa agttcctggg atgaatcggc atcatgagaa  48600
gctgctgggt cagcagctgg atcagctggg cagaaactgc tgtttcattt caggcaatgc  48660
ctgacgatgc ttcaggcaat ctgtaacttc gtaaacgtca tcctggacct ctcctaatga  48720
tgtggctatg ggaggggtgc atagcgatct gtatatgttt gttgagtatc caccagggac  48780
aaagcatcat gccaagtaat gttgggattg tgatgaaaca tcatcaaagt agctcacttc  48840
tcagggctca cagtctagct gggagaccag gtttgtacac gcacgtgcac acttacacac  48900
aggtagggca aggcagatga ggccaagcca aatgagaggg acagacagga agaggctagg  48960
agtttggggg agacagatgc ctgtctgtgg gatggatgag gtctgtgggg ggagctggtt  49020
ttccccagca tctgattttc agagcatcat taactctttc cttcagaggt tctaaggctg  49080
agcggaacag cgcacttgag tggggatgtg acttctttgt gttttcttat tgtgttcttt  49140
cttggttctg tcttttcagg aagtagcata agtggggtgg agggggtgcc caggaatcgt  49200
tttgataaga agctggggtg ctgagggcaa agttagtttg gcccatatgg agtacacctg  49260
agcttccatc ttggtcctgt tgataggaag tagagggata gaggtgggga aagcactcac  49320
actgtctctc tcctgtctgt gtggggttgt tactgccact gtgtcacccc acacagtgtg  49380
gcagttttcc agctgttagg ggagtgagat cagcttctct cccacttgta gagtggagcg  49440
gatcgagcag aatgccacca acaccttcct ggtctacacc gaggaggact tgggagacct  49500
cttgaagatc cagctcacct gggagggggc ctctcagtct tggtacaacc tgtggaagga  49560
gtttcgcagc tacctgtctc aaccccgcaa ccccggacgg gagctgaata tcaggcgcat  49620
ccgggtgaag tctggggaaa cccagcggaa gtaagtgcct cctgctcctt cttctgcctg  49680
gtgtaggtgg ggaacagaag gctgtgcctg tgacatttcc tttcctttgc tgcatctacc  49740
ctcaatcctt ccctccagca tgcaggtaaa acttcaaaca cctttgcaag gacaagtgac  49800
ttccagatca aggcttctat caaaactgtt acgcatctca tgccctgaac atgggccctc  49860
agggagacgg gtgggccagt ggaggcagta attcagccct ggctctgttt gccaggcctt  49920
gtgtcagcct ggaggagggg gacttctcct ggactgggct ttttaggagt gctgccttgt  49980
cgatgtgttt actgtggggt ccatgcagac aaaaggcttt gcttgcttct gagcaaagca  50040
gactggagta tcacttccag agagccccca tggatgaggt ctgtgggagg aactggtttt  50100
ccccagcatc tgattttcag agcattattc tctctccttc agaggttcta agtcaaggat  50160
gtggggctgt ggtcctaact gcaagtaaca gagaatcctc tgtgccacac tagctggcag  50220
tttcccattt cttttaaccc caagcctagc ataaaagatc cagatctttc tatcagctcc  50280
```

-continued

```
taacaccgtg cctggactcc ctgagcaggc tttttctaa acagaagcca gggaagcctg  50340
cgagaccttt gtcaagaagg gagagtttcc ttaaccaagt ccttcagctg acctctacag  50400
aggtcactgc cagccttggc atgggaggag gcagctgcct ccctctttgt ccctcctctg  50460
gcattttctc cattataatt cctgccatgt ctggtttaca ttcgtcatct atgacacagc  50520
ttggcagcag agggaagtga agtggaggct tggagccctc agctgaatga ttctagtcta  50580
gaaacctgtg aactgggggt gctggcctgt ggtctagact gtgtatgttt ttacttctct  50640
gggcccttgc aggtacaaac tatacctatg gatgtgagag cagaaagatg atcatttata  50700
aataaaatat ttcaaagaaa ataaacacct attaaatcac cattgagact cacaaatgta  50760
aatagtttc catttgggtt tagatatcag atttttaaaa agtaaaacat tatagataca  50820
gttgaagccc ctgtgtcctt ctctgctcta cccttcttct ttcaaaccaa atataactaa  50880
tatttcaatg ttaacaaatg ttagtgtgtt tccttccatc atgtttttat acactttgta  50940
cttactgttt tttttgagac tgagtctctc tctttcatcc aggctggagt gcagtggcac  51000
aatcttggct cactgcaaac tccgcctccc ggattcaagt gattctcctg actcagcctt  51060
ctgagtaact gggattacag gtgtgttgcc accatgccca gctaattttt gtatttttat  51120
tacagacggg gtttcgccat gttggccagg ctggtttcag actcctgatc tcaggtgatc  51180
tgcctgcctc agcctcccaa agtgctgaga ttacaggtgt gagccaccat gcccagccgc  51240
cttagtactt ctgtctgtgt acataaacaa tgtatagaat tttggatgct tctgaatttt  51300
acatgagtgg acataatatt ttacaatttg attttttcat tctaatattg tttgtgaaat  51360
ttatccaaaa cataaagatc taatctattc ttgtttaact cctgtatgta aatcaccatt  51420
gcacaaatag ttttgccatt gttctgctga atagttgagt tgttgctttt ttgtagttac  51480
aaatggtgct gagatgaaca tcctctgcat tttccttgtg cacatgtgtg taagggctgt  51540
ttctcagcat gtgttctaaa aagtggaatt gctgggttgt agtatatgca ttctccagct  51600
tgaacagata ttgttaaatc tgtctccaaa gtggttgaac taattttcca tcttaactat  51660
ggatgaagag ttccctttc cctcctttc acccaggtct ggtgggacat tcttgtcatt  51720
ttgttaggtg tgaatgggcc ccctgctgtt gtttgaattt gcatttcctg attgtgcgtg  51780
agataggtca tgtttttata tgtgtataaa catataggtc ctaaggtcct tagggcttcc  51840
tgggaaaggt tcttaagctc ttctgaatgg ggcttttgtc ctgcctcagc tccagggtca  51900
ggtgccccac acccttaagg attacgtggt cacgctaatc acacgcccct gaggctgcgt  51960
ggggcagcca taagttacat ggaaatggtt attaggccct gattctttct tgtggtcttg  52020
gctgtccatt tgctgaatct ttggttttga cttgcagctg agttgcagtt gnnnnnnnnn  52080
nnnnnnnnnn nnnnnnnnnn nnnnnnnnnn nnnnnnnnnn nnnnnnnnnn nnnnnnnnnn  52140
nnnnnnnnnn nnnnnnnnnn nnnnnnnnnn nccagcagca gcggaaagaa atatcctgga  52200
ggaagttgaa ctttaccctg cttgggaatc tatccaggtc tgaagcccct ctaccgaggt  52260
ccccagaatg ttccccgctt tccccactga gtctgctggg gagtaaagtc caagatgaca  52320
gctcagttgt tcccacgtgg cagtgtcctc tgagggatcc aaataaacct ggagttttat  52380
tatcctgact gtgccgataa ggagactggc cgacctaggc agagaaagtg gaggccactg  52440
tccggtatct cttggcaggt cacactcatt cctttctgt tcacatcagc tgggcttgta  52500
acagctccca gtgatagcgt atccaggctg gtcacccgac ggtggagtct tgtccatttg  52560
gaaggcccag accaatgact gaagtaaact actcacccca caatttactg ctcctagaac  52620
aaattgcttg tcttggtgat aattctcttg tgtatggctg aaactatcag ctctgggata  52680
```

-continued atgtgcataa ctttgcatgg attgataaag ctccatttat ttatttggct aaacagagtt 52740
attacactat tacttcttct atgagtttct gacataaagt cagacaaact caaatgcaag 52800
cttatttatt tatttattta tttatttatt tatttattta tttatttatt tttgagactg 52860
agtcttgctc tgttgcccag gctggagtac agtggcgcaa tctcggctca ctgcaagctc 52920
cacctcccaa gttcaagtga ttctcctgcc tcagcctccc gcatagctgg gattacagat 52980
gggcaccacc acgctcggct aatttttgta ttttttagta gagacagggc ttcgccatgt 53040
tggccaggct ggtctcgaac tcctgacctc aagcgatttg cccaatttgg tctcccaaag 53100
tgctgggatt atgggcatga gccaccatgc ccggcctcaa atgcaagctt ttctatcatc 53160
atactaatcc tgctgaatga atttggagct caattcctat ggggggggcaa gagcctagag 53220 gtcaaagctg tcctcttgaa tcctggtgtc gttgatgcgt gcataaggct ttgcttgttc 53280
atactctctc aggcagaagt gtaatttgag gaaaatgtag tgtgcatgtg tgtgtgtgca 53340
catgcacatg tgtgcataca tgtcctataa gaatgagaat gggtgcccac ttttcttggc 53400
tcctctccct tgtgcctctg ggcctttctg cctgaatgca cttgcctgga aatccttgtc 53460
gatctctctc attcaatgac cagagcacca actatggagt ttggaaacct ggctccagcc 53520
ctgattctgg cattgacatg ctgcataaca ttggtgaaag caactggcct ctttgaacat 53580
cccttcctgg tgtgtggcag gaaacatttg gtttccttga actgaacccg cctgacaatg 53640
ggaagatttg cctgaaccac ctcccctgct gggtagctat agggattaaa tgatgtaaca 53700
gaaggtaaag caggattatt ttttaaactt ttatctattt ttaatgccct cctatgtatc 53760
ttcaaggcca gagccttctg agacactcca gcccacggtg actgctctcc tcttatctgt 53820
cacttcttta gccttatact gctttgctta ttatgatcta tttatgtgtt gcgctttatc 53880
cacttgtctt gtccataagc tctttttctg cccttttgaa tcttttcagt ggctagtgtg 53940
ctgccttcat cataactgat ttcagtatgt ctttccagat tgactactta attgaatttg 54000
gaatatgggg aaggagactt agtgtaaagg gaccacccaa tacaaggtct gagattattt 54060
tatgccatat ttcatggtgg aataaggaat gaataacaca atctgaatga ataatgcagt 54120
gtatcatgag ttgggaaggg agaaaaaaaa gagtatttgt acatgtcatt ttttctttct 54180
ttcttttttt gttttttttga gatggagtct tgctctgtta cccaggctgc agtgtagtgg 54240
cgtgatctcg gctcactgca acctctccct cctggggtca agcgattctt ctgcctcagc 54300
cacgcaagta gctgggatta taggagcacg ccaccgcacc tggctaaatt tttgtatttt 54360
tagtagagat ggggtttcac cgtggtggcc aggctggttt caaactcctg acctcaaatg 54420
atccgcctgc ctcagcctcc caaagtgctg ggaatacagg catgagccac tgcgcccggt 54480
atatacatgt cattttcaat cattttgacc tgaatcacct ggttttatct ggtcaatgaa 54540
agcagaggac aatggtcaaa cttactattt gggtcttttg agacaaagta accagctgat 54600
cgactgtctt ttctgctcag cagaacttgc tggccctgga agccatgagg agtaactgaa 54660
ctgaggcgaa taggctcata gctggggagg aaacagcaac atagcaacat ttttactttt 54720
gccttattgg tgtaaccttg ttcacaagga agacatggaa gggaaaggac ttggagagtg 54780
agagaggaaa cagaaaagaa agattgtgag gaagggccag gaggaagcaa atagagcttc 54840
cagttcatgc ttggggagta ctcaaagtgt ccatgggaga gctacgggtg gttgcttcat 54900
atgcagggag aggcctggcc agacccacct tcctcccagc tctgacccca gagtgaggtc 54960
agtgtccagt ttccacgtga acgatttgca gaccccaccc tttccccagc aggtagcaaa 55020

-continued

```
ggccacctca cttgtgtcta tgcacaagcc tgggctcaga gattctctca agccctagtg  55080
tcagtgctct ccagatcaag aggaccaaca gagtatatat ctatagagaa gtttatttta  55140
aggcattggc tcacgtgatg atggaggctg gcaagtccaa aatctgcagg gtaggcctgc  55200
agcctggaaa cccagtgaag aattgcagtt tgagtccaaa ggcagtctgc tggcagaatt  55260
ccttcttgcc cctgagcaag aaggaattat tttctatgca ggccttccac tgattggatg  55320
aggcccaccc attcaatgga gggtcatcta atttactcaa agcctattga tttaaattta  55380
atctcattcc agcactttgg gaggtggagg tgggtggatc acttgaggtc agggagtcga  55440
gacnnnnnnn nnnnnnnnnn nnnnnnnnnn nnnnnnnnnn nnnnnnnnnn nnnnnnnnnn  55500
nnnnnnnnnn nnnnnnnnnn nnnnnnnnnn nnnnnnnnnn nnnttttcaa aaaaaaaaaa  55560
aaaaaaaaaa aagaaccatg tcttcatgaa gcttacattt tttgaaaagg agatagaaat  55620
ttaagaagaa aactaataaa tgtgataatt tcattcagtg agatatgttg tgaagacaat  55680
aaaacaagat tatgtcagag aggagctcca tagactgagt gtcagggaag gagttaaggc  55740
ttcagtgact ggaagaagcc aacacgtgaa gacctagttg taaatcattg gaaggaaggg  55800
caaaagcaaa ggcatcaaga caggaatgag ttgactgtat ccctgaagca gcaaggagcc  55860
aatgtggctg gagcaaagtc agtgcagagg aaaagtatag gaaatgaggg cctggagcta  55920
gatcagcctg cacagcacag taagcagttt ggactttatt gggtgtgaaa tgtgaagtct  55980
ttcaagggtt ttaacctggg aagtgctttg gagagaagtg gggagtgtta tattatatag  56040
tttatatttt ttaaagatta cattttctgg ttatagttat catagttcta gaaactgtat  56100
tttaggacaa ccaaatcacc ccagttaata agagaaagct ctttttacaa agaatgccaa  56160
gctattcaga ttaaagaaaa ataaagagac atggcaacca aacacaatgc cttattctga  56220
atttggctct tcgtccaaaa aaaattctat aaaagatatt gttgggaaaa ttggcggcaa  56280
ttaaatatgg tctctaggtt agataatatt attatagtaa atgttaaatt ttctgattct  56340
aaaactgatt atgaaagaga acaacctggc caggcacggt ggctcatgcc tgtaatccca  56400
acactttgga aagccgagac gggcagatca cctgaggtca ggagttcaag accaacctgg  56460
ccaacatagt gaaacccagt ctgtactaaa aatacaaaaa ttagccaggc gtgatggtgg  56520
gcgactgtaa tcccagctac tcaggaggct gaggcaggag aatcacttga accccggagg  56580
cagaggttgc agtgagccga gattcgcgcc aataccactc tagcttgggt gacagcaagc  56640
ctcctgtctc aaaaataaaa ttataagaaa caacaaccag atgtcatgtg ggacctagat  56700
tgggtcttgc tttgtttctg gttttttgt gtgtgtgtgg ctgctttggt tggttggttt  56760
gtttgtttgt ttgtttgttt gagacagagc cttgctctgt cacccaggct ggagtgtagt  56820
gacatgatct caactcactg caacctctgt ctcccagctt caagcaattc acatgcctca  56880
gcctccagag tagctgggac tacaggtgtg tgccaccaca ccctgctaat tttttctatt  56940
tttagtagag acagggattc accatgttgg ccaagctggt ttcgaactcc tggcctcaag  57000
tgatctgcct gcctcagctt cccaaagtgc tgggattaca ggtgtgagtc agtgtgcctg  57060
gcgggtcttg ctttgaacaa accaactgga aaggacattt ggggaacaac tgggataact  57120
gaaattgagg ttaggtatta gaagagatga aaatgtatca acatggtaaa attgagatta  57180
actggaaaaa aatctgatta tgaaatagca tgtacagtat aatttcacct ggtaagtata  57240
tatgtatata catacacaca tgaagtatat atctcacact atactagaag gatatattaa  57300
agcttaatct tttggaaata taaggatttt attttcttaa tctgcttacc tgctatatct  57360
gactttctat aaaacacata taaataatct taaatttttg aataatttta aaattttact  57420
```

-continued

```
tattatttat ttatttattg agatggagtc actctgtcac ccaggctgga gtgcaatggt  57480
gcgatcttgg ctcactgcaa catctgcctc ccgggttcaa gagattctcc tgcctcagcc  57540
tcccgagtac ctgggattac aggcacgcac caccatgccc ggctaatttt ttcttttctt  57600
ttcttttttc tttttctttt ttttttttga gacagagact cgctctgtca cccagactgg  57660
agtgcagtgg tgcgatctcg gctcactgca acctccgcct cccaggttca agccatgctc  57720
ctgcctcagc ctcccaagta gctgggacta caggcgtgtg ccaccatgcc cggctaattt  57780
tttgtatttt tagtagagag agatggggtt tcaccgtgtt agccaagata atctccatct  57840
cctgacctcg tgatccacct gccttggcct cccaaagtgc tgggattaca ggcgtaaggc  57900
atcttgcctg gcaacttttt ctatttttag taaagacagg gtttcaccat gttggccggg  57960
ctgatcttaa ctcctggcct caagtgatct gccaccccgg cctcccaaag tgctggggat  58020
acaagcgtga gccaccgcac ctggccaatt ttaaattttt taataaataa attgctctgg  58080
ctgttctaga tggattacag gggcaatcaa gagtggaagt aggttgtcta gttgatcagc  58140
aatatgcttt tcagtatctg tttcccaagt ctaggtggaa gccagattct tgctggaaat  58200
gaagcttctc cttcatggga atcccacata catggccaaa gagatcttac gtctgggagc  58260
acaaactggg tatgttaaag ggcttgatat tctccagggt attttgttgt ccaacaaagc  58320
tgggtagaga tttgcacagg tccacggagc tgctcagcaa agggagggtc tggaggagtg  58380
ctatccagca gactaaaggc aaggcaccag ccctctttga agttatacac tggtccagcc  58440
agggaaatca caagcacaca cacataccca acatcagtta atgacaagat aagaaagaaa  58500
atgtactttt aaatttgatc ttaaaacaat tcacaactct taaaaattat gcagaataag  58560
ccaggcgtga tccaccaagc ctggtccatg attaatagta aatgtgaagc atccggccac  58620
aacacgtggt ataggctgaa tatccctaac ccgaatatct gaaatccgac atgttccaaa  58680
atcgaaaact ttttgagaac caacataaca ccacaagtgg aaaattccac acctgacttc  58740
acatgacagg tcacagtgaa actgcaggtg cacaagccag tttatttaac atacccannn  58800
nnnnnnnnnn nnnnnnnnnn nnnnnnnnnn nnnnnnnnnn nnnnnnnnnn nnnnnnnnnn  58860
nnnnnnnnnn nnnnnnnnnn nnnnnnnnnn nnnnnnngcc tctgttattg cagctgaata  58920
accatcccaa agtcaagcaa tattgtgtgg gattctggag aattgagaaa tagcaaaata  58980
atttttgatg gaggcagctg gcagggctag ccctgcctgc aaagttgtcg gaaaggacag  59040
gtcccacggg aaagagtagc aatatgagat agtgccaaaa ctatggaatt tgaagtcaaa  59100
tgagctgagg tttccacact gacgtctttg agcaattact tcacctctct cagccagttt  59160
cctcacctaa aatatatgca tgatgatgat tctgccatta caggaaatgt tgacatgact  59220
gtagtaataa caattcacat tatggattat tttctatttg ccatgcacta ttatttcgca  59280
aaatgaccct atggaacaga tagcaccgtt attcccatta tatagtcaat atgtgccagt  59340
gtactctgta aagtactata caaatattag gtattctttt ctagcataga ctgccagtaa  59400
attcactgag cttgcagaat tatgacagga aaacatatta aaacccaaag tagactgggc  59460
cctgtggctt atgcctgtaa tcccaatact ttgggaggct aaggtgggag gatcacttga  59520
gcccaggagt tcggaaggac cagcctgagc aacatagcga tacactgtct caacaaaaaa  59580
tacaaaaatt agctgggagt ggttggcaca ccctcggtcc cggctactcg ggaggctgat  59640
gtgggaaaat cgcttgagcc cgggaggttg aggcttcagg gagccataat ctcaccattg  59700
cactctaccc tgggcaacag aacgagacac tgtctcaaaa aaaaaaaaaa cccccaaact  59760
```

-continued

```
acctaactaa aaagccatag acactactat gcagtcattg taaagaatgc tatggatgca  59820
tatttatttg aaaacatttt catgatacac tgagtggaaa catatatagt atcaaatttt  59880
cataagtgaa ttatattagg ttggtgcaaa actaattgtg gttttgccac ttaatataat  59940
atttatatta atatattaaa tgatatatta atataacata tgtaatatat gtttactata  60000
atatttataa tacctatgta tatgtgctgt tggaaaaaag acaaataata ttaacaatat  60060
tgcaactttg ggtaatgaga tcctgtgtgg ttaaaattag tttttcccta tgttttctaa  60120
tttttctgca aggaatatga agtacatgta caattttatt ttaaaattac agcaaaaaga  60180
gactcagggc tgggcgtggt gactcatgcc tgtgatccca acactttggg aggccgaagc  60240
aggcagatca cctgaggtca gcagtttgag accagcctgc ccatcatggc gaaaccccgt  60300
ctctacgaaa aatacaaaat tagccaggca tgcgcctgta gccccaacta ctcaggaggc  60360
tgatgcagga gaatcacttg aacccagacg gtggaggttg ccacgagccg agatcatacc  60420
cctgtactcc agcctgggtg acagagccag actctgtctc aaaaaaataa aaaataaaaa  60480
aagagactca ggcatgaaaa cctaactcaa aatatttttt aatattgcct ggcacacagt  60540
ctactttccc cagactgact cagcaacagt tgtgagcatc tcctcaaaac tggctttata  60600
gacctaagaa gcaaaatatt ttatttcaag gggatcctat tagtgaaatt ttacatcgtc  60660
tccctttggt catttttgga tgacttgaaa taaacagtct tgcctgtgtt cctaggcaaa  60720
tgttataatg ttgctaggca aatatcataa atcggaagat aagattagga atattttta  60780
ctacgtagga agtgttgagt tnnnnnnnnn nnnnnnnnnn nnnnnnnnnn nnnnnnnnnn  60840
nnnnnnnnnn nnnnnnnnnn nnnnnnnnnn nnnnnnnnnn nnnnnnnnnn nnnnnnnnnn  60900
nttacctccc ccaagacctc acccttttt tttttttttt gagacagagt ttcactcttg  60960
ttgtccaatc tggagtgcaa tggcactatc tcagctcaca gcaatctctg tttcccgggt  61020
tcaagcgatt ctcctgcctc agcctcctga gtagctggga ctacaggcgc acgccaccac  61080
gcccagctaa tttttgtatt tttagtagag acggggtttc accatgttgg ccaggatggt  61140
ctcggtctct tgaccttgtg atctgcctgc ctcggcctcc caaagtgctg ggattacggg  61200
cgtgagccac cgcgcctagc cctggtttgg tttttttttt tagagacagg gtctcgctca  61260
gttgcccaga ttggagtgca gtggcatgat catggctcac tgcagctgcg atctcttggg  61320
ctcaagcaat cctcctgctc cagactccca agtagctagg actacagctg tgcaccatta  61380
cgcccagcta tttttttggt agagatgggg gtctcactat gttgcttagg ctgagctgga  61440
actcctgacc tcaagtattc ctcccttctc agcctccaaa actattggaa ttgcaggcat  61500
gagccactgc acctagcccc catgttaact attattagtt tgtgactttt cctaatttgt  61560
cccagacagg aaggagacag tgacagctgc actgtgcccc ctccctaagt tctgccatca  61620
gaactgctcc tctgacatct tttctgatgg ccagaaggcc accaggaccc atagtgatca  61680
ggctgtctca acctctttcc ccaggctagg ctaagggctc aggaaaagga agaatgaatg  61740
ggggctctgt agagtgcatc taagctctcc tgcatgcagg agggactgga gaacgaactg  61800
tgtagcttct taccttatca ggcaggcaat acccaggaat gctggagtca ctgcttttgg  61860
agcattcaaa ctctctgcag cactttctga gtcttgctgc taacagctgg ccttgcaagg  61920
aattcattac catagcacca caggaggcct tagaggacgc cggttcagga gcttgctcag  61980
tcatttgtgc agctcactgg ctgtgcatct ctgtcggaat cctctcatgt ccctagaact  62040
caaatcacta acattcccta cgctgttgta actttatttt actacctgtt cagccagcct  62100
ctgcttgaac acatgcagtg attgggatct catttctctt ccacatagac catttcacta  62160
```

-continued

```
ctagtaagct taatttcact gaaccaccta tggtgaagtg attcctgagt cattaaataa  62220
ctttctactg caccctttct catagggtta tttggagact taaataagat aacagtgcct  62280
tgctcacaga aaacagcctg taatgtgaat tgacaattat tgctgctgat attgttttca  62340
gaaagttctt atatggagct gaaatctgca ttctgtaact tcgaaaactt ggtcttaatt  62400
tggctcattg gcataacaga aaataagtct aatcatgccc gcctgaggat ggttctactt  62460
atcacaagtc tcctcttagt ctagttcttc atactcagtt ccttcagccc ttccacatgg  62520
gacgtaattt ccagatctct caccatcctg actgcccttc cctggacagg ttctgtttga  62580
ccttcatccc tccttggagg agtggccagg tgctggcaac taagacatgc gagctgtcca  62640
ccatctggat tatgcagatg aactaacatt gaaaatgaca cgctacatgc attacttaat  62700
ttcgttctca cagcaccttc atgaggagaa aactgaggct cagagatgtt aagtagcttt  62760
ccccaaatcg tttagctcag aaattgtgga accagaattc aacccagatc tgtctgactc  62820
caaagtctgc tcttctttct tggggaagtg gaagcctgag tgctgttctt ggaacagcct  62880
caagacaata atctggggac tgtcttggtc ctgcttgcag agggtccttc tgttacgtat  62940
gggtcctttc tggcccttta gcttctacaa agaaagtcag tccccctcca gctctaaaga  63000
cacatgaagt ctgtttgcag tccagacctt gcaaacttgt agttatagaa acctcagagg  63060
cctaccaggg cttgaaggat atttggctcc actttacatc tccattcttc ttttcctcct  63120
gtttttaatg taacctgtaa tcctagcaat ttgggaggct gaggcaggtg gatcacctga  63180
ggtcaggagt tcaagatcag cctggccaac atggtgaaac tccgtctcta ctaaaaatat  63240
aaaaattagc tgggctaatt tttaattagt gtggtggccc gcgcctttat tcccagctac  63300
tcaggaggct gaggcaggag aattgcttga acctggaagg cggagattgc agtgagctga  63360
gattgtgcca ttgcactcca gccttggcaa caagagtgaa actccgtctc aaaaaaaaaa  63420
agtattctgt ccaccacgtg gaataatgta atatttagta ataagaacag ctgcaaggtg  63480
tagagagtta ccgtatatcc atcacccagc tttccttaac gttaacattt tatataacca  63540
cagcatcatt ttgtcaaaac tagataatca gcattggtac aatactgtta actaaactct  63600
aaacttcatt taggtttcat caggctttcc actattgcct ttttcaattc caggatgcan  63660
nnnnnnnnnn nnnnnnnnnn nnnnnnnnnn nnnnnnnnnn nnnnnnnnnn nnnnnnnnnn  63720
nnnnnnnnnn nnnnnnnnnn nnnnnnnnnn nnnnnnnnnt ttataagatt ttaaaactgg  63780
caaaaaatat tatggattta ttcatagcta gtaccagcat taaaattttt tttttttttt  63840
ttttttttaa gaaacagggc ctcactctgt tgctgagtac aatgctggag tacagtggcg  63900
tgattatagc tcattgtaac ctcaaactcc tgggctcaag ggagcctcat tgcctcagcc  63960
tcctaagtag ctggaactac aggtacatgc caccaaagcc cagctaatat tctgttattt  64020
ggtaaagatg gggtctcact gtgttgccca ggctggtctc gaactctttc tgccttggct  64080
tcaaccacag tgctgacatt acaagcatga gctactgagc ctggccaaga ggaattaatt  64140
taactagaaa tctatagctt ttcaagctac caattaagtt tgaaagtaga ataaaaacat  64200
tttctgattt gccaagattc aaaagacctc ccaggaacct acaaggaagc tacaagatgt  64260
actccttcca catgagggaa caagccaaga aaaaggaaga aattcaagaa acaggggatc  64320
caacacaggg cagtggtata gagaatcaca gccatgcagc aggctgggac aagagtcaaa  64380
acagctcccg gatcaaccag gagaagaaag catagaactg acggttcact tgatgcgtct  64440
aaccttattc tgtggaatgt tacaatactg taggagaatt tggaagcaat gaataatagt  64500
```

-continued

```
tatatggaga ataaagtaaa taatttcgta tagactacaa actttgggaa aaacaagtta  64560
ttcaagaaag gtcatgtaat catagtatac gactaaattc aacagtaatc aacatttata  64620
taatcactat gatataaata ctaaatattt aaccaaaaat tgtgagttaa ctctactgag  64680
aagattccag aagcagcagc aggattggtg gtctacgagt gctaaacctt catcttccat  64740
aataggtagt gctcaataga aaatatgtaa agttagtaaa tcaaaaaaca gtaaaaattt  64800
attagttata aataaggaag tagggccagg tgtggtatta tcccaacatt ttgggaggcc  64860
gaggcaggtg gatcacttaa ggccagaagt tcgagactaa cctggtcaac atagtgaaaa  64920
cccgtctcta ctaaaaatac aaaaattagc taggcatgtt ggagcatgcc cataatccca  64980
gctcctcagg aggctaaggc acgagaatca cctgaacctg ggaagtggag attgcagtga  65040
gccgagattg tgccactgca atccagcctg ggcgacagag tgaaactctg tctcaaatta  65100
aataaataag gaggtaaata gcaaaaagca acagcttata gatttttaaa tggtggccag  65160
gcgcggtcgc tcacacctgt aattccagca ccctgagagg ccaggcggat gggtcacctg  65220
agacaggagt tgagaccagc ctgaccaann nnnnnnnnnn nnnnnnnnnn nnnnnnnnnn  65280
nnnnnnnnnn nnnnnnnnnn nnnnnnnnnn nnnnnnnnnn nnnnnnnnnn nnnnnnnnnn  65340
nnnnnnnngc ggttcacgcc tgatatccca gcattttggg aggccaaggc aggcgaatca  65400
tgaggttaag agatcaagac catcctggcc aacatggtga aacctgtctc ccgttaaaat  65460
accaaaatta gcccggcatg gtggcaggta taatcccagc ttacttggga gactgaggca  65520
ggagaatcac ttggacccac ggaggcggag gttgcactga gctgagattg caccccttgca  65580
atgcagcctg ggcaaccatt gccaaactcc atttccaaaa aaaaaaaata ttcttagggt  65640
ttggggcttt tttgggggggg gttggggtgt aactatggta aatgggatta ccttttaaat  65700
tttttttctt ttttttgaga tgggagtctt gctatgttgc ccaagctggt ctgaactact  65760
gggctcaagc aatctgcctg cctcagcctc ccgagtagct gggattacag acgtacacca  65820
ttgtgccatc ttgatttctt ttcttgtttg tgtctagaaa tgctacttgt ttttgaatac  65880
tgattttgta tcctgcaact ttactaaatt cacttattag ttctgagact tattgagtag  65940
agtctttata tttttctcgt tttttgagac agagtcttgc tctgttgccc aggctggagt  66000
gtggtggtgt gatctcggct ctctgcaacc cccacctccc aggttcaagt gatttcccta  66060
cctcagcctc ctgagtaact gggattacag gcatgcacca ccacgcccag ctaatttttt  66120
tgtattttta gtagagacag ggtttcgcga tgttgaccag tctagtctca aactcctgac  66180
ctcaagtgat ccaccatcct ctaccaccca aagtgctggg attacaggca tgagccactg  66240
cgtccggcct gatttttcta tatataaaat catgtcatct gtaaacaggg actattttac  66300
ttccttcttt tcaaattgaa tgtccttttt tctttctttt gcctaattgc tctggctagg  66360
acttccagta ttatgttgta attcaagaaa tatttgttga gaacttatca taaacaaaaa  66420
aattattcta ggcactagag gaaaataata cagacaagaa ctatgtcttc tgccaggcac  66480
agttgctcat gcctgtaatc ccagcacttt ggaaggtcga ggtgggcgga tcacctgagc  66540
tcaggagttc gagaccagcc tggccaaaat ggcgaaaccc cctctctact aaaaatacaa  66600
aaattagccg tggtggcatg cgccggtaat cccagctact ggggaacctg aggcaggaga  66660
atcatcgaaa cccgggagtc ggaggttgca gtgggcacaa gatcacgcca ctatactcca  66720
gcctgggcga nnnnnnnnnn nnnnnnnnnn nnnnnnnnnn nnnnnnnnnn nnnnnnnnnn  66780
nnnnnnnnnn nnnnnnnnnn nnnnnnnnnn nnnnnnnnnn nnnnnnnnnn cttttttttg  66840
ggggtttccc cggccccccc cttttttttt tttttttttt tttttttttt tgtgagaccg  66900
```

-continued

```
agtcttgctc tgttgcccag gatggagtac aatggtgcaa tctctgctca ctgcaacctc  66960
cgcctcctgg gctcgagcag ttctcctgct ttagcttcct gagtagctgg gattacaggt  67020
acccaccacc atgcttggct aatttttagt agagatgggg tttcaccatg ctggccaggc  67080
tggtttcaaa ctcctgaccg taaatgatct gcctgccttg gcctcccaaa gtgctgggat  67140
tacaggcatg agtcaccatg tctggcctcc ccatttaaaa tggcaacccc tgccctgcct  67200
cctagcacct ctgtctcctt cctctgcttt attttctcta gaacacttac caccacctga  67260
catattatat atcttaacta tttctttgtt tacagtctgc cttccctgct aagatgaaag  67320
gcattcttgt ctattttgat cattgctgta tttccagtgc cagtacttaa taaatacttg  67380
ttgaataaat gcatgataaa ttctgaagct atttaaactt tttcaattgt actgagcacg  67440
ggctcagtac aaggaaatct acacacatag tttaccacat ttacacatca aaggtggatc  67500
aaaaattttt tcaataggca tttgaaaaac attagaaatg aaatacttta ataacaaggg  67560
tgattatata cttaatatac aaatgtctct actttttaa ctcagtggta agaatttact  67620
ttttcaatct cataaagaag ggctctctaa gcaagatata aacacagaaa ataaaaggga  67680
aacataataa acttggctat acacattttt tttttgaaa cagtcttgtt ctgtcaccca  67740
ggctagagtg cagtggtgca acctcagctc actgcaacct ccacctccca ggttcaagca  67800
attctcatgc ctcagtctga gtcatgtgcc acccgcccca acccacccca ccccaccccc  67860
agctaattgt tctattttta gtagagacag ggtttcacca tgttggccaa atttgttttt  67920
aactctgatg aaaatgagtt aaacaaagtc aaagataatt taaactaagt cacaaaatat  67980
tgcaacatat aagannnnnn nnnnnnnnnn nnnnnnnnnn nnnnnnnnnn nnnnnnnnnn  68040
nnnnnnnnnn nnnnnnnnnn nnnnnnnnnn nnnnnnnnnn nnnnnnnnnn nnnnaccaca  68100
gaatcagcaa cagttcacat agggcaaatg ttttaaataa acattttta aactccatgt  68160
tgcaagaagt agcaacacta acaaaagcaa tatttatata aggacatact ttgtaaccag  68220
tttaaaggcc aagggagggt taggttaatg agggctcagg cagtcaggaa ggcttctgag  68280
aggctatggc cttgagaggc aggtggcctt ttggatagac agaaggaagc aggtggcaga  68340
ggtctggcag aggctgcatg aggccgaatc atggaagcct caaagtgaga cacaggttag  68400
agtccctgca gtagtgatgg ggaattctga aggcttttga gtcggggcat ggcatgaaaa  68460
tttcacccct gcctcctcac ccatctgcct tgaatctaga aagcacagct ggattccccc  68520
taaagttctg cctacatcag tggtttcttt tccctcctag actgacattt tgtacagaag  68580
accctgagaa caccagcata tccccaggcc gggagctctg gtttcgcaag tgtcgggatg  68640
gctggaggat gaaaaacgaa accaggtaac caggactttc tcacacgttc cacccaggac  68700
acgttgacat gatgatctcc tagcatgtgc tggggatgga tctgggtgcc agggacatag  68760
catgaacaaa acagataaaa atctcttcct ttaagaagtt gggccgggcg tggtggctca  68820
agcctgtaat cccagcactt tgggaggcca aggcaggcag atcacctgag gtcaggagtt  68880
tgagaccagc ctggctaaca tagtgaaacc ccatctctac taaaaaaaaa aaaaaaaaga  68940
atgccgggca tggtggtgtg tgcctgtaat cccagctact tgggaggttg aggcaggaaa  69000
atcacttgaa cctgaaaggt ggaggctgca gtgagctgaa accgcaatgt tgcactccag  69060
cctaggtgac agaaatgaag ctctgtctca aaaagaaaga aagggccagg catggaggct  69120
cacgcctgta atcccagcac tttgggaggc tgaggcaggc ggatcacgag gtcaggagat  69180
cgacacaatc ctggctaaca cagtgaaacc tcatctctct aaaaatataa aaaattagac  69240
```

-continued

```
gggcatggtg acgggtgcct gtagtcccag ctactcggga ggctgaggca ggagaatggt  69300
atgaacctgg gaggaagagc ttgcagtgag ctgagattgc accactgcac tccagcctgg  69360
ggtgacagag tgagactccg tctcaaaaaa ataaaaaaaa aaaaaaaaaa nnnnnnnnnn  69420
nnnnnnnnnn nnnnnnnnnn nnnnnnnnnn nnnnnnnnnn nnnnnnnnnn nnnnnnnnnn  69480
nnnnnnnnnn nnnnnnnnnn nnnnnnnnnn aaaaaaaaaa aaaaaaaaaa aaaagaagct  69540
gaccttctgc taggagataa agaagcaagt gaaatactgt agataggatg ttggaagtgt  69600
taatgtctct tctgctcttt gtcctgcctc aacctgtagg ggttcattgt acatgaccct  69660
actggcatga gatcttctct gtaactaagt ccccaggttg gtgcccattc ctgccatctt  69720
tgaagtatct tttttttttt cctttgagac atggtcttac tctgttaccc aggctggagc  69780
gcagtggcat gatcctggct cactgcagcc tcgacctccc caggcttggg tgatccttcc  69840
gcctttgcct cctgtatagc tgggaccaca ggcacttgcc accacgctga gctaatttgt  69900
gtattttttt gcagagacgg ggtttcacca tgttgcccag tctggtcttg aactccatgg  69960
ctcaagtgat ccgcctgcct tggcctccca gagtgctggg attacaggtg tgagccactg  70020
tgcctggccc ctgccatctt tgattgacat cttctctgta ataactagag ctgtgggaac  70080
gtgcctaagg gctcctagct tccttctggc caccaggtca ggtttgggaa tggggtggga  70140
gataaagaga agcacaaagc atgttctcct ttcttaggtt ttctagaatg caggtaagtg  70200
tgggcctaat tctcccacac actttttttt tttttttttt gagacaaagt ctcactctat  70260
cgctcaggct ggagtgcagt ggagtgatct tggcttacta aaacctccgc ctcccgggtc  70320
caagtgattc tccttcctca accttccgag tagctgggat tacaagtgcc tgctaccacg  70380
cctggctaat ttttgtattt ttagttgaga tgggttttcg ccatgttggc caagttacca  70440
tgttggccaa gttggtctca aactcttgat ctcaagtgat ctgcccacct tggcctccaa  70500
aagtgctggc attacaggtt tgagccacgg tgcccaaccc caatccttcc cctttttggg  70560
aaacagaaat gcccatgtat gtggagctaa gtgagacaga ggggttgtca tgcttcacta  70620
tccccttgtc ccatgctgca atccgttatt tcagacgtga ggaaggccca tcttgtggtg  70680
tgaggcagtg ggctcatcct ggggaacagc cacacgccct ctaagccaaa acacctgcta  70740
aggaggaagg agactgtctc ctcacaccat gcctgtcgcc accctttgct ctaacaaggg  70800
tactagataa taatactgct gtggtacacc tagcacttag cttgggccca gcctgcaccc  70860
agggacttac ataatgatgt ttgtcatcaa cccactaggc aggggttgtt agccctgtgt  70920
acagatgagg aaccgaggct cagggagatg aagtttctct cccaaggccc ccagcaatgg  70980
cagagggagt tgaagcaggt cggtctaccc caaagcctgt gttgttgagc accgaggctc  71040
caagtgctca gatgatcacc tcgcgtctgt ctgggtatca attatcaggc agctgtgccc  71100
gtgctccggg gtcgcctgtg attaaccatt tgccaccccc aaggctgcgc tgcatcccag  71160
ctgctctgtc tcctggttag gagctcaaca caaccacaag caccatcatc acaggactcg  71220
tgccatctaa ttaagggact cagtctagcg taggctcgta tgattttcta ctactataac  71280
gattgtaaat ctttatgtat ttaaatgtgt acatttcaaa gtgtttccac atatattaac  71340
ttcattgatc ctccagacaa ccatgtagat tggacacacc caggaaagat gactaaggaa  71400
ggctattctt tttttattga gacagggtct tgctctgtca cccaggctgg agtacagtgg  71460
catgatcaca gctcattgca gcctcgacct ccctgggctc agatgatctt cctacctcag  71520
cctcctgagt agcttggatt acaggaatgt gccactatgc ctggctaatt tttgtagaga  71580
tgaggtttca ccatgttgcc caggctggtc tctatctcct gagctcaagt gatctgcctg  71640
```

-continued

```
cctcggcctc ccagtgctgg gtttgcaggc atgagccact gtgcccagtc aggatggcta  71700
ttcttatgat aaaggctaag atatttattc ttctttcccg ctttggaatt catatacctg  71760
agaactctat gattcaccct ctcactacta attttagaaa acaagctgtc cttttccatt  71820
ccctcaaaaa caataggagt ccaagtaata aatgaacact aggaagtcat agcatcatat  71880
gtaacatgtt tagcatcctc cctcctgaca tggatgctgt tcacatgttc actgataagg  71940
agcctgagat tcagagaggt tcagtggtgt gttcacatag ctgagactag aatccaggtc  72000
tcctaactct cagtcttgcc ccctttctgc caatacagtg tctctcttgt atttctagat  72060
caaggcaaag aggacacttt gatagttctc cccacacttg tgtgtccatg attgtgtgtg  72120
tgtgtgtgtg tgtgtgtgtg tgtgtgtatg ttgtgggtgg ataatatgta aatgcaagaa  72180
ctgtgatgta ctcaactcag ggtccagagg gtgctgcagt gtggtgtttc tcaaagtgta  72240
tctatggctt gtcaggttag ggagagaagg cagcactcgg gaccttgtcc atttattctg  72300
aaaggaatac atgtaaaata gtcccatagg ggtgtcagaa agcttggcct taaggtcaaa  72360
agagcacacc ctgaatacag gtttgcgcgt ttgctggtgt gtgagctaac aaatgccact  72420
ctcacacggt ttctttcagt cccactgtgg agcttccctg agggtgcccg ggcaagtctt  72480
gccagcaagg cagcaagact tcctgctatc caagcccatg gaggaaagtt actgctgagg  72540
acccacccaa tggaaggatt cttctcagcc ttgaacctgg agcactggga acaactggtc  72600
tcctgtgatg gctgggactc ctcgcgggag gggactgcgc tgctatagct cttgctgcct  72660
ctcttgaata gctctaactc caaacctctg tccacacctc cagagcacca agtccagatt  72720
tgtgtgtaag cagctgggtg cctggggcct ctcgtgcaca ctggattggt ttctcagttg  72780
ctgggcgagc ctgtactctg cctgacgagg aacgctggct ccgaagaggc cctgtgtaga  72840
aggctgtcag ctgctcagcc tgctttgagc ctcagtgaga agtccttccg acaggagctg  72900
actcatgtca ggatggcagg cctggtatct tgctcgggcc ctagctgttg gggttctcat  72960
gggttgcact gaccatactg cttacgtctt agccattccg tcctgctccc cagctcactc  73020
tctgaagcac acatcattgg ctttcctatt tttctgttca ttttttaatt gagcaaatgt  73080
ctattgaaca cttaaaatta attagaatgt ggtaatggac atattactga gcctctccat  73140
ttggaaccca gtggagttgg gatttctaga ccctctttct gtttggatgg tgtatgtgta  73200
tatgcatggg gaaaggcacc tggggcctgg gggaggctat aggatataag cattagggac  73260
cctgaggctt taagtggttt ctatttcttc ttagttatta tgtgccacct tcttagttat  73320
tatgtgccac ctcccctatg agtgacgtgt ttgatcacta gcagaatagc aagcagagta  73380
tcattcatgc tggggccaga atgatggccg gttgccagat ataactgctt tggagcaaat  73440
ctcttctgtt tagagagata gaagttatga catatgtaat acacatctgt gtacacagaa  73500
accggcacct gccagacaga gctggttcta agatttaata cagtgctttt tttcctcttt  73560
gaaatatttt actttaatac cagtgccttt tcttgttgaa cttcttggaa aagccaccaa  73620
ttctagatct tgatttgaat taatacacac aatatctgag acacttacac ttttcaaaag  73680
atttgtgtat gcattgccta attagagtag ggggagaagg gcaactatta ttatccctat  73740
tttacaaaac tgaggcttag tgaggttcag ccacatgcct agacttatat actagttagt  73800
ggtgcagcca gggagaggac tcagatttcc tggaggcaaa gtctatctct gaaactccat  73860
gaagactttt gcagccagtt cccaccaata tgccccagac gtgagacaaa caaggacttt  73920
tttttttata tagagccatc cataaaatcc taagcccttt tattaatgta taaccaggag  73980
```

-continued

```
aacatctgtg ccaacggttg gactttttat ggctgagatt cgggaggaag tgtgacacca  74040

agcaggagag gaagaatgat tttctttgta cttaggtttt ctaaggacat tgttttaatc  74100

tgtatcgtgc caaagttgta tcactgttaa acttctgaag acataaccag ttgagtctta  74160

tttcaagata tgttctcaag ccaattgtgt gcttctcttg tttctgtgat tgctttctag  74220

ccaaagcgaa gcttgtacag gttgagtatc ccttatccaa aatgcttgga accagaagtg  74280

tttcaaattt tagattattt tcagattttg gaatgtttgc atatacataa tgagatattt  74340

tgggaatagg acccgagcct aaacacaaaa ttcattgatg tgtcagttac accttatcca  74400

catagcctga gggtaatttt atacgatatt ttaaatagtt gtgtacatga agcatggttt  74460

gtggtaactt atgtgagggg ttttcccatt ttttgtcttg ttggtgctca aaaagttttg  74520

gattttggag catttcggat tttggatttt tggattaggg ttgctcaacc catattattg  74580

gctgtacatc ctggtcactt ctgacttctg tttttactaa tggaagcttt gcaaattgaa  74640

ttctcagtga gttgtatatt tatacacctg gcttgaagcc ttaattgtat ataatgatgc  74700

tttttaaaaa atgctatttg gaagactatt tatttctcgt gtatataatg tatataaaaa  74760

aatatggtta gtgtttacct aaggttaacc aatttcaaga ttaaaatttt taaatagtaa  74820

aataataaaa aattataaag ttcttaatgg tctgacaact caattttttt tttttttttt  74880

tttttttttg agacagagcc tctctctgtc acccaggctg gagtgcagtg gcaatcttgg  74940

ctcactacaa cctctgcctc ctgggctcag gtggtcctcc cacctcagcc ttctgagtag  75000

ctgggattac agagatgcgt caccatgtct ggc                               75033
```

```
<210> SEQ ID NO 19
<220> FEATURE:

<400> SEQUENCE: 19

000


<210> SEQ ID NO 20
<211> LENGTH: 289
<212> TYPE: DNA
<213> ORGANISM: homo sapiens
<220> FEATURE:

<400> SEQUENCE: 20

cccatattat tggctgtaca tcctggtcac ttctgacttc tgtttttact aatggaagct     60

ttgcaaattg aattctcagt gagttgtata tttatacacc tggcttgaag ccttaattgt    120

atataatgat actttttaaa aaatgctatt tggaagacta tttatttctc gtgtatataa    180

tgtatataaa aaaatatggt tagtgtttac ctaaggttaa ccaatttcaa gattaaaatt    240

tttaaatagt aaaataataa aaaattataa aaaaaaaaaa aaaaaaaaa                289


<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21

tcaacggctt gccccagaac                                                  20


<210> SEQ ID NO 22
<211> LENGTH: 20
<212> TYPE: DNA
```

-continued

<213> ORGANISM: Artificial Sequence
<220> FEATURE:
<223> OTHER INFORMATION: Antisense Oligonucleotide

<400> SEQUENCE: 22
ggtggaaaat gaaaacttgg 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
cccctcccaa gaaacagaag 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ggagttgctc atcctgcccc 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ctctggacca aaaggtacgg 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tgtggagctt atcttccagc 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ctcacagatg gtttgacctc 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
gacggagagg tagcatcctt 20

-continued

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cagggctgac acgagtttgt 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
attgaccgca tccgtgtaaa 20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tccttctcct gcagccagtc 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
cgtccttctc ctgcagccag 20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gtggacattc ccgagagaaa 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ctccgaggct gtagccgatc 20

<210> SEQ ID NO 35
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 35
aaacatgggc ccggcaggat 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
cagcctggct ggaagtcacc 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tcctgattca ccagagagtc 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gcttgtcctg attcaccaga 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
aaaactcggc ttgtcctgat 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gcactggaag gcaaaactcg 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gaagcgattg gagtcagtgc 20

-continued

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tgaaaggcat gcctgcccgg 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ctgataatgg taaactctga 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ttcttgtaac tgaagacatg 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gacgtaaaag gtgggctcaa 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gctccactat ttccagtggc 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gaaggtgttg gtggcattct 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 48
aggtctccca agtcctcctc 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
aggccccctc ccaggtgagc 20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gtagctgcga aactccttcc 20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gatattcagc tcccgtccgg 20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
aaatgtcagt ttccgctggg 20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tgttctcagg gtcttctgta 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
cacagtggga ctggtttcgt 20

<210> SEQ ID NO 55
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 55
ggcaccctca gggaagctcc 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ttgctgcctt gctggcaaga 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gtcctcagca gtaactttcc 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
acagaggttt ggagttagag 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ccaatccagt gtgcacgaga 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gggcctcttc ggagccagcg 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61

-continued

```
caacccatga gaaccccaac                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62

aggacggaat ggctaagacg                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63

caatagacat ttgctcaatt                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64

atcccaactc cactgggttc                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65

aggtgccttt ccccatgcat                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66

tgcttatatc ctatagcctc                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67

ccacttaaag cctcagggtc                                               20

<210> SEQ ID NO 68
<211> LENGTH: 20
<212> TYPE: DNA
<213> ORGANISM: Artificial Sequence
```

-continued

<220> FEATURE:
<223> OTHER INFORMATION: Antisense Oligonucleotide

<400> SEQUENCE: 68
tagtgatcaa acacgtcact 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
acatatgtca taacttctat 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
caacaagaaa aggcactggt 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ttaattcaaa tcaagatcta 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ctaattaggc aatgcataca 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ctcactaagc ctcagttttg 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tggctgcacc actaactagt 20

-continued

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gactttgcct ccaggaaatc 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ggctgcaaaa gtcttcatgg 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
atggatggct ctatataaaa 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
taaaagggct taggatttta 20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
acagatgttc tcctggttat 20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ataaaaagtc caaccgttgg 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 81
ctcccgaatc tcagccataa 20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ctctcctgct tggtgtcaca 20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
atcattcttc ctctcctgct 20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ggcacgatac agattaaaac 20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gaagtttaac agtgatacaa 20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ttgaaataag actcaactgg 20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ccaaaacttt ttgagcacca 20

<210> SEQ ID NO 88

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
agacctttta ctttttgcaa 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
cctagcctgg gaacccaaac 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ggatccaaac ctgcagcaga 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
tgaaggttac ctctgaaagg 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
taatggtaaa ctgcagtgac 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
aggcacttac ttccgctggg 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94

-continued

```
gtcatagatg acgaatgtaa                                                  20


<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95

gaattctgcc agcagactgc                                                  20


<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96

ttcttaagaa gattgggttt                                                  20


<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97

atatacaatt aaggcttcaa                                                  20


<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98

agtatcatta tatacaatta                                                  20


<210> SEQ ID NO 99
<211> LENGTH: 2227
<212> TYPE: DNA
<213> ORGANISM: Mus musculus
<220> FEATURE:
<221> NAME/KEY: CDS
<222> LOCATION: (275)...(1777)

<400> SEQUENCE: 99

cggcccgact tcgcagcggc tctgggaaag gacaggtcgg gctgggcagc gtgtccctcc      60

acacgctcgc tttcccggtc accgctcgca gcgctaccaa ccttccaggt tctgccagct     120

gtccacccca tcaccttctg gccgacaccc ggcctgtcca cttctagtct ctggaggttt     180

tagtggtttc aaaccaaacc aacccaaacc aacccaacaa caaaaaagcc caaaccaaaa     240

acctgcttga gaggaggggg cgtggcgggg aagg atg cga aac acg gtt ttc ctg     295
                                      Met Arg Asn Thr Val Phe Leu
                                       1               5

ctc ggc ttt tgg agc gtc tat tgt tac ttc ccg gcg gga agt atc aca       343
Leu Gly Phe Trp Ser Val Tyr Cys Tyr Phe Pro Ala Gly Ser Ile Thr
        10                  15                  20

acc ttg cgt ccc cag ggg tcg ctg cga gat gag cat cat aaa ccc act       391
```

-continued

```
Thr Leu Arg Pro Gln Gly Ser Leu Arg Asp Glu His His Lys Pro Thr
     25                  30                  35

gga gta cca gct acc gcc aga ccc tct gtg gct ttt aac atc cgc act      439
Gly Val Pro Ala Thr Ala Arg Pro Ser Val Ala Phe Asn Ile Arg Thr
 40                  45                  50                  55

tct aag gac cca gag cag gaa ggg tgt aat ctc tcc ctt ggt gac agc      487
Ser Lys Asp Pro Glu Gln Glu Gly Cys Asn Leu Ser Leu Gly Asp Ser
                 60                  65                  70

aaa ctc tta gaa aac tgt ggc ttc aac atg aca gcc aaa acc ttc ttc      535
Lys Leu Leu Glu Asn Cys Gly Phe Asn Met Thr Ala Lys Thr Phe Phe
             75                  80                  85

atc att cat gga tgg acg atg agt ggc atg ttt gag agc tgg ctg cat      583
Ile Ile His Gly Trp Thr Met Ser Gly Met Phe Glu Ser Trp Leu His
         90                  95                  100

aaa ctt gta tca gcc ctg cag atg aga gag aaa gat gct aac gtc gtg      631
Lys Leu Val Ser Ala Leu Gln Met Arg Glu Lys Asp Ala Asn Val Val
    105                 110                 115

gtg gtt gac tgg ctg ccc ctg gct cat cag ctg tac acg gat gca gtc      679
Val Val Asp Trp Leu Pro Leu Ala His Gln Leu Tyr Thr Asp Ala Val
120                 125                 130                 135

aat aac acc agg gtg gtg gga cag aga gta gct ggg atg ctt gac tgg      727
Asn Asn Thr Arg Val Val Gly Gln Arg Val Ala Gly Met Leu Asp Trp
                140                 145                 150

ctg cag gag aag gaa gag ttc tct ctt ggg aac gtt cac ttg att ggc      775
Leu Gln Glu Lys Glu Glu Phe Ser Leu Gly Asn Val His Leu Ile Gly
            155                 160                 165

tac agc ctt gga gca cac gtg gct gga tac gct ggc aac ttt gtg aaa      823
Tyr Ser Leu Gly Ala His Val Ala Gly Tyr Ala Gly Asn Phe Val Lys
        170                 175                 180

gga aca gtg ggc agg atc act ggt ctg gat ccc gcg ggt ccc atg ttt      871
Gly Thr Val Gly Arg Ile Thr Gly Leu Asp Pro Ala Gly Pro Met Phe
    185                 190                 195

gaa ggg gtg gac atc aac aga agg ctg tcc ccg gac gat gca gac ttt      919
Glu Gly Val Asp Ile Asn Arg Arg Leu Ser Pro Asp Asp Ala Asp Phe
200                 205                 210                 215

gtg gat gtc ctg cat acc tac acg ctg tcc ttt ggc ttg agc att ggg      967
Val Asp Val Leu His Thr Tyr Thr Leu Ser Phe Gly Leu Ser Ile Gly
                220                 225                 230

att cgg atg cct gtg ggt cac att gac atc tat ccc aat ggc ggt gac     1015
Ile Arg Met Pro Val Gly His Ile Asp Ile Tyr Pro Asn Gly Gly Asp
            235                 240                 245

ttc cag cca ggc tgt gga ttc aat gat gtc atc gga tct ttt gca tat     1063
Phe Gln Pro Gly Cys Gly Phe Asn Asp Val Ile Gly Ser Phe Ala Tyr
        250                 255                 260

gga aca atc tca gag atg gtg aaa tgc gag cac gag cga gcc gta cac     1111
Gly Thr Ile Ser Glu Met Val Lys Cys Glu His Glu Arg Ala Val His
    265                 270                 275

ctc ttt gtc gac tct ctg gtg aat cag gac aag ccc agc ttt gcc ttc     1159
Leu Phe Val Asp Ser Leu Val Asn Gln Asp Lys Pro Ser Phe Ala Phe
280                 285                 290                 295

cag tgc aca gac tcc agc cgc ttc aaa agg gga atc tgc ctc agc tgc     1207
Gln Cys Thr Asp Ser Ser Arg Phe Lys Arg Gly Ile Cys Leu Ser Cys
                300                 305                 310

cgg aag aac cgt tgt aat aac att ggc tac aac gcc aag aaa atg aga     1255
Arg Lys Asn Arg Cys Asn Asn Ile Gly Tyr Asn Ala Lys Lys Met Arg
            315                 320                 325

aag aag agg aat agc aaa atg tat tta aaa acc cgg gct ggc atg cct     1303
Lys Lys Arg Asn Ser Lys Met Tyr Leu Lys Thr Arg Ala Gly Met Pro
        330                 335                 340
```

-continued

```
ttc aaa gtt tac cat tac cag ctg aaa gtt cac atg ttc tct tac aat     1351
Phe Lys Val Tyr His Tyr Gln Leu Lys Val His Met Phe Ser Tyr Asn
    345                 350                 355

aac agt ggg gac acc cag ccc acc ctc tac att acc ctg tat ggt agc     1399
Asn Ser Gly Asp Thr Gln Pro Thr Leu Tyr Ile Thr Leu Tyr Gly Ser
360                 365                 370                 375

aac gca gac tcc cag aac ctg ccc ttg gaa ata gtg gag aag att gag     1447
Asn Ala Asp Ser Gln Asn Leu Pro Leu Glu Ile Val Glu Lys Ile Glu
                380                 385                 390

ctg aat gcc aca aac acc ttc ctt gtc tac act gag gag gac ttg ggc     1495
Leu Asn Ala Thr Asn Thr Phe Leu Val Tyr Thr Glu Glu Asp Leu Gly
            395                 400                 405

gat ctc ttg aag atg cga ctt acc tgg gag ggg gta gcc cat tcc tgg     1543
Asp Leu Leu Lys Met Arg Leu Thr Trp Glu Gly Val Ala His Ser Trp
        410                 415                 420

tgc aac ctg tgg aat gag ttt cgc aac tac ctg tct caa ccc agc aac     1591
Cys Asn Leu Trp Asn Glu Phe Arg Asn Tyr Leu Ser Gln Pro Ser Asn
    425                 430                 435

ccc tcg agg gag ctg tac atc cgg cga att cgt gtc aaa tct ggg gaa     1639
Pro Ser Arg Glu Leu Tyr Ile Arg Arg Ile Arg Val Lys Ser Gly Glu
440                 445                 450                 455

acc cag cgc aaa gtg aca ttt tgc act caa gac cca acg aag agt agc     1687
Thr Gln Arg Lys Val Thr Phe Cys Thr Gln Asp Pro Thr Lys Ser Ser
                460                 465                 470

atc tcc cct ggc cag gag ctg tgg ttt cac aag tgt cag gat ggc tgg     1735
Ile Ser Pro Gly Gln Glu Leu Trp Phe His Lys Cys Gln Asp Gly Trp
            475                 480                 485

aaa atg aaa aac aaa acc agt ccc ttt gtg aac ttg gcc tga             1777
Lys Met Lys Asn Lys Thr Ser Pro Phe Val Asn Leu Ala  *
        490                 495                 500

gggcccaaga agtcctggcg tccacaccca caccccactg tccacgcaca tggaggaaaa   1837

gttactgctg aagacccact cgatggacga tctcagcctt gagccccacg aggagcttgc   1897

ttgctgggct catcctgtct cccctgacaa ctgtgacttc tcctggagag gcctgtgcac   1957

tgctgaagtt cttgctgatg attctagctg taaacctttg ttgccgccgc aggaagctga   2017

ggccagcttg tgtgtgagca ctggagtgtc cagagccctg cacactcggg gtggggggcg   2077

gggtactctc cctgtcgcta ggtgagcact ggctttgtcc aacatcaggg aacacaaggc   2137

tctgaagtgg ccctgtgtgg aaggttggca gctgcctggc ctcactgaac cttagtgaca   2197

agtctttgcc tcaggagctg actcatgccg                                    2227


<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100

ttcccagagc cgctgcgaag                                                 20


<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101

gaacctggaa ggttggtagc                                                 20
```

-continued

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
cctccagaga ctagaagtgg 20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
actaaaacct ccagagacta 20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
cgtgtttcgc atccttcccc 20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
aggttgtgat acttcccgcc 20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
tcatctcgca gcgacccctg 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tggtactcca gtgggtttat 20

<210> SEQ ID NO 108
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 108
tgcggatgtt aaaagccaca 20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
gtcaccaagg gagagattac 20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
gccacagttt tctaagagtt 20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
gttattgact gcatccgtgt 20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
accctggtgt tattgactgc 20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
ccagtcaagc atcccagcta 20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gttcccaaga gagaactctt 20

-continued

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
cacgtgtgct ccaaggctgt 20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
catccacaaa gtctgcatcg 20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
caggacatcc acaaagtctg 20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
gtatgcagga catccacaaa 20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
tgtaggtatg caggacatcc 20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
cagcgtgtag gtatgcagga 20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 121
aaggacagcg tgtaggtatg 20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
agccaaagga cagcgtgtag 20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
gctcaagcca aaggacagcg 20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
ccaatgctca agccaaagga 20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
gaatcccaat gctcaagcca 20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
catccgaatc ccaatgctca 20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
tagatgtcaa tgtgacccac 20

<210> SEQ ID NO 128
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 128
tgggatagat gtcaatgtga 20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
cgccattggg atagatgtca 20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tttcaccatc tctgagattg 20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
aaagaggtgt acggctcgct 20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
tcgacaaaga ggtgtacggc 20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
gagagtcgac aaagaggtgt 20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134

-continued caccagagag tcgacaaaga 20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
cagattcccc ttttgaagcg 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ccaatgttat tacaacggtt 20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tgtgaacttt cagctggtaa 20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
taagagaaca tgtgaacttt 20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
cccactgtta ttgtaagaga 20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
atttccaagg gcaggttctg 20

<210> SEQ ID NO 141
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 141
gtgtagacaa ggaaggtgtt 20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
gagatcgccc aagtcctcct 20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
gtaagtcgca tcttcaagag 20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
taccccctcc caggtaagtc 20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
ggaatgggct accccctccc 20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ctcattccac aggttgcacc 20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
gggtttcccc agatttgaca 20

-continued

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
cacttgtgaa accacagctc 20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
aaagggactg gttttgtttt 20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
ttgggccctc aggccaagtt 20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
ccagcaagca agctcctcgt 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
tcagcaagaa cttcagcagt 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
caaaggttta cagctagaat 20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 154
cttcctgcgg cggcaacaaa 20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
gctcacacac aagctggcct 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
gggctctgga cactccagtg 20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
gctcacctag cgacagggag 20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gccttgtgtt ccctgatgtt 20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
acacagggcc acttcagagc 20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
cttccacaca gggccacttc 20

<210> SEQ ID NO 161

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
ttcagtgagg ccaggcagct 20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
taaggttcag tgaggccagg 20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
gacttgtcac taaggttcag 20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
aatagaacca ggatccatca 20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
tctgctagag atcaagggtg 20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
gcgcagcagg tatgtagaac 20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
tcaaactact aaagggtgtc 20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
ccaggaaacc ttgctgggtc 20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
atggagttac agaaaggatt 20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
acagatgcaa agaatgtgcg 20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
tataaagctg gtacaataca 20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
aaaactaacc atagatttgt 20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
aaatcttgaa atcggttaat 20

<210> SEQ ID NO 174
<211> LENGTH: 20
<212> TYPE: DNA

-continued

<213> ORGANISM: H. sapiens
<220> FEATURE:

<400> SEQUENCE: 174
gttctggggc aagccgttga 20

<210> SEQ ID NO 175
<211> LENGTH: 20
<212> TYPE: DNA
<213> ORGANISM: H. sapiens
<220> FEATURE:

<400> SEQUENCE: 175
gctggaagat aagctccaca 20

<210> SEQ ID NO 176
<211> LENGTH: 20
<212> TYPE: DNA
<213> ORGANISM: H. sapiens
<220> FEATURE:

<400> SEQUENCE: 176
gaggtcaaac catctgtgag 20

<210> SEQ ID NO 177
<211> LENGTH: 20
<212> TYPE: DNA
<213> ORGANISM: H. sapiens
<220> FEATURE:

<400> SEQUENCE: 177
aaggatgcta cctctccgtc 20

<210> SEQ ID NO 178
<211> LENGTH: 20
<212> TYPE: DNA
<213> ORGANISM: H. sapiens
<220> FEATURE:

<400> SEQUENCE: 178
acaaactcgt gtcagccctg 20

<210> SEQ ID NO 179
<211> LENGTH: 20
<212> TYPE: DNA
<213> ORGANISM: H. sapiens
<220> FEATURE:

<400> SEQUENCE: 179
tttacacgga tgcggtcaat 20

<210> SEQ ID NO 180
<211> LENGTH: 20
<212> TYPE: DNA
<213> ORGANISM: H. sapiens
<220> FEATURE:

<400> SEQUENCE: 180
gactggctgc aggagaagga 20

<210> SEQ ID NO 181
<211> LENGTH: 20
<212> TYPE: DNA
<213> ORGANISM: H. sapiens
<220> FEATURE:

-continued

<400> SEQUENCE: 181
ctggctgcag gagaaggacg 20

<210> SEQ ID NO 182
<211> LENGTH: 20
<212> TYPE: DNA
<213> ORGANISM: H. sapiens
<220> FEATURE:

<400> SEQUENCE: 182
tttctctcgg gaatgtccac 20

<210> SEQ ID NO 183
<211> LENGTH: 20
<212> TYPE: DNA
<213> ORGANISM: H. sapiens
<220> FEATURE:

<400> SEQUENCE: 183
gatcggctac agcctcggag 20

<210> SEQ ID NO 184
<211> LENGTH: 20
<212> TYPE: DNA
<213> ORGANISM: H. sapiens
<220> FEATURE:

<400> SEQUENCE: 184
atcctgccgg gcccatgttt 20

<210> SEQ ID NO 185
<211> LENGTH: 20
<212> TYPE: DNA
<213> ORGANISM: H. sapiens
<220> FEATURE:

<400> SEQUENCE: 185
ggtgacttcc agccaggctg 20

<210> SEQ ID NO 186
<211> LENGTH: 20
<212> TYPE: DNA
<213> ORGANISM: H. sapiens
<220> FEATURE:

<400> SEQUENCE: 186
gactctctgg tgaatcagga 20

<210> SEQ ID NO 187
<211> LENGTH: 20
<212> TYPE: DNA
<213> ORGANISM: H. sapiens
<220> FEATURE:

<400> SEQUENCE: 187
tctggtgaat caggacaagc 20

<210> SEQ ID NO 188
<211> LENGTH: 20
<212> TYPE: DNA
<213> ORGANISM: H. sapiens
<220> FEATURE:

<400> SEQUENCE: 188

-continued atcaggacaa gccgagtttt 20

<210> SEQ ID NO 189
<211> LENGTH: 20
<212> TYPE: DNA
<213> ORGANISM: H. sapiens
<220> FEATURE:

<400> SEQUENCE: 189
cgagttttgc cttccagtgc 20

<210> SEQ ID NO 190
<211> LENGTH: 20
<212> TYPE: DNA
<213> ORGANISM: H. sapiens
<220> FEATURE:

<400> SEQUENCE: 190
gcactgactc caatcgcttc 20

<210> SEQ ID NO 191
<211> LENGTH: 20
<212> TYPE: DNA
<213> ORGANISM: H. sapiens
<220> FEATURE:

<400> SEQUENCE: 191
ccgggcaggc atgcctttca 20

<210> SEQ ID NO 192
<211> LENGTH: 20
<212> TYPE: DNA
<213> ORGANISM: H. sapiens
<220> FEATURE:

<400> SEQUENCE: 192
tcagagttta ccattatcag 20

<210> SEQ ID NO 193
<211> LENGTH: 20
<212> TYPE: DNA
<213> ORGANISM: H. sapiens
<220> FEATURE:

<400> SEQUENCE: 193
catgtcttca gttacaagaa 20

<210> SEQ ID NO 194
<211> LENGTH: 20
<212> TYPE: DNA
<213> ORGANISM: H. sapiens
<220> FEATURE:

<400> SEQUENCE: 194
ttgagcccac cttttacgtc 20

<210> SEQ ID NO 195
<211> LENGTH: 20
<212> TYPE: DNA
<213> ORGANISM: H. sapiens
<220> FEATURE:

<400> SEQUENCE: 195
gccactggaa atagtggagc 20

-continued

<210> SEQ ID NO 196
<211> LENGTH: 20
<212> TYPE: DNA
<213> ORGANISM: H. sapiens
<220> FEATURE:

<400> SEQUENCE: 196
agaatgccac caacaccttc 20

<210> SEQ ID NO 197
<211> LENGTH: 20
<212> TYPE: DNA
<213> ORGANISM: H. sapiens
<220> FEATURE:

<400> SEQUENCE: 197
gaggaggact tgggagacct 20

<210> SEQ ID NO 198
<211> LENGTH: 20
<212> TYPE: DNA
<213> ORGANISM: H. sapiens
<220> FEATURE:

<400> SEQUENCE: 198
ccggacggga gctgaatatc 20

<210> SEQ ID NO 199
<211> LENGTH: 20
<212> TYPE: DNA
<213> ORGANISM: H. sapiens
<220> FEATURE:

<400> SEQUENCE: 199
cccagcggaa actgacattt 20

<210> SEQ ID NO 200
<211> LENGTH: 20
<212> TYPE: DNA
<213> ORGANISM: H. sapiens
<220> FEATURE:

<400> SEQUENCE: 200
tacagaagac cctgagaaca 20

<210> SEQ ID NO 201
<211> LENGTH: 20
<212> TYPE: DNA
<213> ORGANISM: H. sapiens
<220> FEATURE:

<400> SEQUENCE: 201
acgaaaccag tcccactgtg 20

<210> SEQ ID NO 202
<211> LENGTH: 20
<212> TYPE: DNA
<213> ORGANISM: H. sapiens
<220> FEATURE:

<400> SEQUENCE: 202
ggagcttccc tgagggtgcc 20

-continued

<210> SEQ ID NO 203
<211> LENGTH: 20
<212> TYPE: DNA
<213> ORGANISM: H. sapiens
<220> FEATURE:

<400> SEQUENCE: 203
tcttgccagc aaggcagcaa 20

<210> SEQ ID NO 204
<211> LENGTH: 20
<212> TYPE: DNA
<213> ORGANISM: H. sapiens
<220> FEATURE:

<400> SEQUENCE: 204
ggaaagttac tgctgaggac 20

<210> SEQ ID NO 205
<211> LENGTH: 20
<212> TYPE: DNA
<213> ORGANISM: H. sapiens
<220> FEATURE:

<400> SEQUENCE: 205
ctctaactcc aaacctctgt 20

<210> SEQ ID NO 206
<211> LENGTH: 20
<212> TYPE: DNA
<213> ORGANISM: H. sapiens
<220> FEATURE:

<400> SEQUENCE: 206
tctcgtgcac actggattgg 20

<210> SEQ ID NO 207
<211> LENGTH: 20
<212> TYPE: DNA
<213> ORGANISM: H. sapiens
<220> FEATURE:

<400> SEQUENCE: 207
cgctggctcc gaagaggccc 20

<210> SEQ ID NO 208
<211> LENGTH: 20
<212> TYPE: DNA
<213> ORGANISM: H. sapiens
<220> FEATURE:

<400> SEQUENCE: 208
cgtcttagcc attccgtcct 20

<210> SEQ ID NO 209
<211> LENGTH: 20
<212> TYPE: DNA
<213> ORGANISM: H. sapiens
<220> FEATURE:

<400> SEQUENCE: 209
aattgagcaa atgtctattg 20

<210> SEQ ID NO 210
<211> LENGTH: 20

-continued

<212> TYPE: DNA
<213> ORGANISM: H. sapiens
<220> FEATURE:

<400> SEQUENCE: 210
atgcatgggg aaaggcacct 20

<210> SEQ ID NO 211
<211> LENGTH: 20
<212> TYPE: DNA
<213> ORGANISM: H. sapiens
<220> FEATURE:

<400> SEQUENCE: 211
gaggctatag gatataagca 20

<210> SEQ ID NO 212
<211> LENGTH: 20
<212> TYPE: DNA
<213> ORGANISM: H. sapiens
<220> FEATURE:

<400> SEQUENCE: 212
gaccctgagg ctttaagtgg 20

<210> SEQ ID NO 213
<211> LENGTH: 20
<212> TYPE: DNA
<213> ORGANISM: H. sapiens
<220> FEATURE:

<400> SEQUENCE: 213
agtgacgtgt ttgatcacta 20

<210> SEQ ID NO 214
<211> LENGTH: 20
<212> TYPE: DNA
<213> ORGANISM: H. sapiens
<220> FEATURE:

<400> SEQUENCE: 214
atagaagtta tgacatatgt 20

<210> SEQ ID NO 215
<211> LENGTH: 20
<212> TYPE: DNA
<213> ORGANISM: H. sapiens
<220> FEATURE:

<400> SEQUENCE: 215
accagtgcct tttcttgttg 20

<210> SEQ ID NO 216
<211> LENGTH: 20
<212> TYPE: DNA
<213> ORGANISM: H. sapiens
<220> FEATURE:

<400> SEQUENCE: 216
tgtatgcatt gcctaattag 20

<210> SEQ ID NO 217
<211> LENGTH: 20
<212> TYPE: DNA
<213> ORGANISM: H. sapiens

-continued

<220> FEATURE:

<400> SEQUENCE: 217
caaaactgag gcttagtgag 20

<210> SEQ ID NO 218
<211> LENGTH: 20
<212> TYPE: DNA
<213> ORGANISM: H. sapiens
<220> FEATURE:

<400> SEQUENCE: 218
actagttagt ggtgcagcca 20

<210> SEQ ID NO 219
<211> LENGTH: 20
<212> TYPE: DNA
<213> ORGANISM: H. sapiens
<220> FEATURE:

<400> SEQUENCE: 219
ccatgaagac ttttgcagcc 20

<210> SEQ ID NO 220
<211> LENGTH: 20
<212> TYPE: DNA
<213> ORGANISM: H. sapiens
<220> FEATURE:

<400> SEQUENCE: 220
taaaatccta agccctttta 20

<210> SEQ ID NO 221
<211> LENGTH: 20
<212> TYPE: DNA
<213> ORGANISM: H. sapiens
<220> FEATURE:

<400> SEQUENCE: 221
ataaccagga gaacatctgt 20

<210> SEQ ID NO 222
<211> LENGTH: 20
<212> TYPE: DNA
<213> ORGANISM: H. sapiens
<220> FEATURE:

<400> SEQUENCE: 222
ccaacggttg gactttttat 20

<210> SEQ ID NO 223
<211> LENGTH: 20
<212> TYPE: DNA
<213> ORGANISM: H. sapiens
<220> FEATURE:

<400> SEQUENCE: 223
ttatggctga gattcgggag 20

<210> SEQ ID NO 224
<211> LENGTH: 20
<212> TYPE: DNA
<213> ORGANISM: H. sapiens
<220> FEATURE:

<400> SEQUENCE: 224
tgtgacacca agcaggagag 20

<210> SEQ ID NO 225
<211> LENGTH: 20
<212> TYPE: DNA
<213> ORGANISM: H. sapiens
<220> FEATURE:

<400> SEQUENCE: 225
agcaggagag gaagaatgat 20

<210> SEQ ID NO 226
<211> LENGTH: 20
<212> TYPE: DNA
<213> ORGANISM: H. sapiens
<220> FEATURE:

<400> SEQUENCE: 226
gttttaatct gtatcgtgcc 20

<210> SEQ ID NO 227
<211> LENGTH: 20
<212> TYPE: DNA
<213> ORGANISM: H. sapiens
<220> FEATURE:

<400> SEQUENCE: 227
ttgtatcact gttaaacttc 20

<210> SEQ ID NO 228
<211> LENGTH: 20
<212> TYPE: DNA
<213> ORGANISM: H. sapiens
<220> FEATURE:

<400> SEQUENCE: 228
ccagttgagt cttatttcaa 20

<210> SEQ ID NO 229
<211> LENGTH: 20
<212> TYPE: DNA
<213> ORGANISM: H. sapiens
<220> FEATURE:

<400> SEQUENCE: 229
tggtgctcaa aaagttttgg 20

<210> SEQ ID NO 230
<211> LENGTH: 20
<212> TYPE: DNA
<213> ORGANISM: H. sapiens
<220> FEATURE:

<400> SEQUENCE: 230
gtcactgcag tttaccatta 20

<210> SEQ ID NO 231
<211> LENGTH: 20
<212> TYPE: DNA
<213> ORGANISM: H. sapiens
<220> FEATURE:

<400> SEQUENCE: 231

-continued cccagcggaa gtaagtgcct 20

<210> SEQ ID NO 232
<211> LENGTH: 20
<212> TYPE: DNA
<213> ORGANISM: H. sapiens
<220> FEATURE:

<400> SEQUENCE: 232
ttacattcgt catctatgac 20

<210> SEQ ID NO 233
<211> LENGTH: 20
<212> TYPE: DNA
<213> ORGANISM: M. musculus
<220> FEATURE:

<400> SEQUENCE: 233
cttcgcagcg gctctgggaa 20

<210> SEQ ID NO 234
<211> LENGTH: 20
<212> TYPE: DNA
<213> ORGANISM: M. musculus
<220> FEATURE:

<400> SEQUENCE: 234
gctaccaacc ttccaggttc 20

<210> SEQ ID NO 235
<211> LENGTH: 20
<212> TYPE: DNA
<213> ORGANISM: M. musculus
<220> FEATURE:

<400> SEQUENCE: 235
tagtctctgg aggttttagt 20

<210> SEQ ID NO 236
<211> LENGTH: 20
<212> TYPE: DNA
<213> ORGANISM: M. musculus
<220> FEATURE:

<400> SEQUENCE: 236
ggggaaggat gcgaaacacg 20

<210> SEQ ID NO 237
<211> LENGTH: 20
<212> TYPE: DNA
<213> ORGANISM: M. musculus
<220> FEATURE:

<400> SEQUENCE: 237
ggcgggaagt atcacaacct 20

<210> SEQ ID NO 238
<211> LENGTH: 20
<212> TYPE: DNA
<213> ORGANISM: M. musculus
<220> FEATURE:

<400> SEQUENCE: 238
ataaacccac tggagtacca 20

-continued

<210> SEQ ID NO 239
<211> LENGTH: 20
<212> TYPE: DNA
<213> ORGANISM: M. musculus
<220> FEATURE:

<400> SEQUENCE: 239
tgtggctttt aacatccgca 20

<210> SEQ ID NO 240
<211> LENGTH: 20
<212> TYPE: DNA
<213> ORGANISM: M. musculus
<220> FEATURE:

<400> SEQUENCE: 240
gtaatctctc ccttggtgac 20

<210> SEQ ID NO 241
<211> LENGTH: 20
<212> TYPE: DNA
<213> ORGANISM: M. musculus
<220> FEATURE:

<400> SEQUENCE: 241
aactcttaga aaactgtggc 20

<210> SEQ ID NO 242
<211> LENGTH: 20
<212> TYPE: DNA
<213> ORGANISM: M. musculus
<220> FEATURE:

<400> SEQUENCE: 242
acacggatgc agtcaataac 20

<210> SEQ ID NO 243
<211> LENGTH: 20
<212> TYPE: DNA
<213> ORGANISM: M. musculus
<220> FEATURE:

<400> SEQUENCE: 243
gcagtcaata acaccagggt 20

<210> SEQ ID NO 244
<211> LENGTH: 20
<212> TYPE: DNA
<213> ORGANISM: M. musculus
<220> FEATURE:

<400> SEQUENCE: 244
tagctgggat gcttgactgg 20

<210> SEQ ID NO 245
<211> LENGTH: 20
<212> TYPE: DNA
<213> ORGANISM: M. musculus
<220> FEATURE:

<400> SEQUENCE: 245
acagccttgg agcacacgtg 20

<210> SEQ ID NO 246

-continued

<211> LENGTH: 20
<212> TYPE: DNA
<213> ORGANISM: M. musculus
<220> FEATURE:

<400> SEQUENCE: 246
cgatgcagac tttgtggatg 20

<210> SEQ ID NO 247
<211> LENGTH: 20
<212> TYPE: DNA
<213> ORGANISM: M. musculus
<220> FEATURE:

<400> SEQUENCE: 247
tcctgcatac ctacacgctg 20

<210> SEQ ID NO 248
<211> LENGTH: 20
<212> TYPE: DNA
<213> ORGANISM: M. musculus
<220> FEATURE:

<400> SEQUENCE: 248
ctacacgctg tcctttggct 20

<210> SEQ ID NO 249
<211> LENGTH: 20
<212> TYPE: DNA
<213> ORGANISM: M. musculus
<220> FEATURE:

<400> SEQUENCE: 249
cgctgtcctt tggcttgagc 20

<210> SEQ ID NO 250
<211> LENGTH: 20
<212> TYPE: DNA
<213> ORGANISM: M. musculus
<220> FEATURE:

<400> SEQUENCE: 250
tcctttggct tgagcattgg 20

<210> SEQ ID NO 251
<211> LENGTH: 20
<212> TYPE: DNA
<213> ORGANISM: M. musculus
<220> FEATURE:

<400> SEQUENCE: 251
caatctcaga gatggtgaaa 20

<210> SEQ ID NO 252
<211> LENGTH: 20
<212> TYPE: DNA
<213> ORGANISM: M. musculus
<220> FEATURE:

<400> SEQUENCE: 252
agcgagccgt acacctcttt 20

<210> SEQ ID NO 253
<211> LENGTH: 20
<212> TYPE: DNA

-continued

<213> ORGANISM: M. musculus
<220> FEATURE:

<400> SEQUENCE: 253
gccgtacacc tctttgtcga 20

<210> SEQ ID NO 254
<211> LENGTH: 20
<212> TYPE: DNA
<213> ORGANISM: M. musculus
<220> FEATURE:

<400> SEQUENCE: 254
tctttgtcga ctctctggtg 20

<210> SEQ ID NO 255
<211> LENGTH: 20
<212> TYPE: DNA
<213> ORGANISM: M. musculus
<220> FEATURE:

<400> SEQUENCE: 255
cgcttcaaaa ggggaatctg 20

<210> SEQ ID NO 256
<211> LENGTH: 20
<212> TYPE: DNA
<213> ORGANISM: M. musculus
<220> FEATURE:

<400> SEQUENCE: 256
aaccgttgta ataacattgg 20

<210> SEQ ID NO 257
<211> LENGTH: 20
<212> TYPE: DNA
<213> ORGANISM: M. musculus
<220> FEATURE:

<400> SEQUENCE: 257
ttaccagctg aaagttcaca 20

<210> SEQ ID NO 258
<211> LENGTH: 20
<212> TYPE: DNA
<213> ORGANISM: M. musculus
<220> FEATURE:

<400> SEQUENCE: 258
aaagttcaca tgttctctta 20

<210> SEQ ID NO 259
<211> LENGTH: 20
<212> TYPE: DNA
<213> ORGANISM: M. musculus
<220> FEATURE:

<400> SEQUENCE: 259
tctcttacaa taacagtggg 20

<210> SEQ ID NO 260
<211> LENGTH: 20
<212> TYPE: DNA
<213> ORGANISM: M. musculus
<220> FEATURE:

-continued

<400> SEQUENCE: 260
cagaacctgc ccttggaaat 20

<210> SEQ ID NO 261
<211> LENGTH: 20
<212> TYPE: DNA
<213> ORGANISM: M. musculus
<220> FEATURE:

<400> SEQUENCE: 261
aacaccttcc ttgtctacac 20

<210> SEQ ID NO 262
<211> LENGTH: 20
<212> TYPE: DNA
<213> ORGANISM: M. musculus
<220> FEATURE:

<400> SEQUENCE: 262
aggaggactt gggcgatctc 20

<210> SEQ ID NO 263
<211> LENGTH: 20
<212> TYPE: DNA
<213> ORGANISM: M. musculus
<220> FEATURE:

<400> SEQUENCE: 263
ctcttgaaga tgcgacttac 20

<210> SEQ ID NO 264
<211> LENGTH: 20
<212> TYPE: DNA
<213> ORGANISM: M. musculus
<220> FEATURE:

<400> SEQUENCE: 264
tgtcaaatct ggggaaaccc 20

<210> SEQ ID NO 265
<211> LENGTH: 20
<212> TYPE: DNA
<213> ORGANISM: M. musculus
<220> FEATURE:

<400> SEQUENCE: 265
gagctgtggt ttcacaagtg 20

<210> SEQ ID NO 266
<211> LENGTH: 20
<212> TYPE: DNA
<213> ORGANISM: M. musculus
<220> FEATURE:

<400> SEQUENCE: 266
actgctgaag ttcttgctga 20

<210> SEQ ID NO 267
<211> LENGTH: 20
<212> TYPE: DNA
<213> ORGANISM: M. musculus
<220> FEATURE:

<400> SEQUENCE: 267

-continued tttgttgccg ccgcaggaag 20

<210> SEQ ID NO 268
<211> LENGTH: 20
<212> TYPE: DNA
<213> ORGANISM: M. musculus
<220> FEATURE:

<400> SEQUENCE: 268
ctccctgtcg ctaggtgagc 20

<210> SEQ ID NO 269
<211> LENGTH: 20
<212> TYPE: DNA
<213> ORGANISM: M. musculus
<220> FEATURE:

<400> SEQUENCE: 269
aacatcaggg aacacaaggc 20

<210> SEQ ID NO 270
<211> LENGTH: 20
<212> TYPE: DNA
<213> ORGANISM: M. musculus
<220> FEATURE:

<400> SEQUENCE: 270
gctctgaagt ggccctgtgt 20

<210> SEQ ID NO 271
<211> LENGTH: 20
<212> TYPE: DNA
<213> ORGANISM: M. musculus
<220> FEATURE:

<400> SEQUENCE: 271
agctgcctgg cctcactgaa 20

<210> SEQ ID NO 272
<211> LENGTH: 20
<212> TYPE: DNA
<213> ORGANISM: M. musculus
<220> FEATURE:

<400> SEQUENCE: 272
cctggcctca ctgaacctta 20

<210> SEQ ID NO 273
<211> LENGTH: 20
<212> TYPE: DNA
<213> ORGANISM: M. musculus
<220> FEATURE:

<400> SEQUENCE: 273
ctgaacctta gtgacaagtc 20

<210> SEQ ID NO 274
<211> LENGTH: 20
<212> TYPE: DNA
<213> ORGANISM: M. musculus
<220> FEATURE:

<400> SEQUENCE: 274 caccccttgat ctctagcaga 20

-continued

```
<210> SEQ ID NO 275
<211> LENGTH: 20
<212> TYPE: DNA
<213> ORGANISM: M. musculus
<220> FEATURE:

<400> SEQUENCE: 275

gttctacata cctgctgcgc                                              20


<210> SEQ ID NO 276
<211> LENGTH: 20
<212> TYPE: DNA
<213> ORGANISM: M. musculus
<220> FEATURE:

<400> SEQUENCE: 276

gacacccttt agtagtttga                                              20


<210> SEQ ID NO 277
<211> LENGTH: 20
<212> TYPE: DNA
<213> ORGANISM: M. musculus
<220> FEATURE:

<400> SEQUENCE: 277

gacccagcaa ggtttcctgg                                              20


<210> SEQ ID NO 278
<211> LENGTH: 20
<212> TYPE: DNA
<213> ORGANISM: M. musculus
<220> FEATURE:

<400> SEQUENCE: 278

cgcacattct ttgcatctgt                                              20


<210> SEQ ID NO 279
<211> LENGTH: 20
<212> TYPE: DNA
<213> ORGANISM: M. musculus
<220> FEATURE:

<400> SEQUENCE: 279

tgtattgtac cagctttata                                              20
```